(12) United States Patent
Oberkircher et al.

(10) Patent No.: US 11,000,410 B2
(45) Date of Patent: May 11, 2021

(54) GUIDE APPARATUS FOR TANGENTIAL ENTRY INTO SUPRACHOROIDAL SPACE

(71) Applicant: ORBIT BIOMEDICAL LIMITED, London (GB)

(72) Inventors: Brendan J. Oberkircher, Cincinnati, OH (US); Benjamin L. Ko, Cincinnati, OH (US); Robert H. Roth, Cincinnati, OH (US); Mark S. Ortiz, Milford, OH (US); Thomas E. Meyer, Cincinnati, OH (US); Franklin S. Busch, South Bend, IN (US); Isaac J. Khan, Bridgewater, NJ (US); Michael F. Keane, Downingtown, PA (US); Anna R. Raymond, Northwood, OH (US); Jacob W. Schubert, Edgewood, KY (US)

(73) Assignee: GYROSCOPE THERAPEUTICS LIMITED, Stevenage (GB)

( * ) Notice: Subject to any disclaimer, the term of this patent is extended or adjusted under 35 U.S.C. 154(b) by 0 days.

(21) Appl. No.: 15/609,419

(22) Filed: May 31, 2017

(65) Prior Publication Data
US 2017/0360605 A1    Dec. 21, 2017

Related U.S. Application Data

(60) Provisional application No. 62/351,620, filed on Jun. 17, 2016.

(51) Int. Cl.
*A61M 9/00* (2006.01)
*A61F 9/00* (2006.01)
*A61F 9/013* (2006.01)

(52) U.S. Cl.
CPC .......... *A61F 9/0026* (2013.01); *A61F 9/0017* (2013.01); *A61F 9/0008* (2013.01); *A61F 9/0136* (2013.01)

(58) Field of Classification Search
CPC .... A61F 9/0026; A61F 9/0017; A61F 9/0008; A61F 9/0136; A61F 9/00736;
(Continued)

(56) References Cited

U.S. PATENT DOCUMENTS 4,454,875 A * 6/1984 Pratt ................. F16B 15/02
606/219
4,462,395 A * 7/1984 Johnson .......... A61B 17/00234
606/100
(Continued)

FOREIGN PATENT DOCUMENTS

EP          1 806 102 A1      7/2007
JP        2003-526461 A       9/2003
(Continued)

OTHER PUBLICATIONS

International Search Report and Written Opinion dated Dec. 18, 2017 for Application No. PCT/US2017/037364, 18 pgs.
(Continued)

*Primary Examiner* — Bhisma Mehta
*Assistant Examiner* — Hong-Van N Trinh
(74) *Attorney, Agent, or Firm* — Frost Brown Todd LLC

(57) ABSTRACT

An apparatus includes a body and a pair of rigid legs extending from the body. The body includes an engagement feature configured to engage a deployment instrument. The legs are parallel with each other. Each leg has a sharp tip. The legs both extend along a plane. The body defines a guide opening. The guide opening is oriented transversely relative to the plane associated with the legs. The guide opening is sized to receive a cannula having a generally flat profile. The guide opening is configured to guide the cannula through a sclerotomy at a substantially tangential orientation.

20 Claims, 44 Drawing Sheets

(58) Field of Classification Search
CPC .............. A61B 17/064; A61B 17/0682; A61B 17/0231; A61B 17/0482; A61B 17/3403; A61B 2017/00004; A61B 2017/0412; A61B 2017/0427; A61B 2017/0445; A61B 2017/0464; A61B 2017/0641; A61B 2017/0409; A61B 17/0401; A61B 17/92

See application file for complete search history.

(56) References Cited

U.S. PATENT DOCUMENTS

| | | | |
|---|---|---|---|
| 4,880,017 A * | 11/1989 | Soll | A61F 9/007 128/898 |
| 4,903,882 A * | 2/1990 | Long | B25C 3/006 227/147 |
| 5,531,760 A * | 7/1996 | Alwafaie | A61B 17/064 606/216 |
| 6,368,315 B1 | 4/2002 | Gillis et al. | |
| 6,824,532 B2 | 11/2004 | Gillis et al. | |
| 7,189,245 B2 | 3/2007 | Kaplan | |
| 7,207,980 B2 | 4/2007 | Christian et al. | |
| 7,214,232 B2 | 5/2007 | Bowman et al. | |
| 7,413,734 B2 | 8/2008 | Mistry et al. | |
| 8,197,435 B2 | 6/2012 | Prausnitz et al. | |
| 8,308,814 B2 * | 11/2012 | Sengun | A61L 27/3654 623/23.72 |
| 8,425,473 B2 | 4/2013 | Ho et al. | |
| 2005/0143363 A1 | 6/2005 | de Juan et al. | |
| 2006/0058802 A1 * | 3/2006 | Kofoed | A61B 17/0642 606/75 |
| 2007/0162030 A1 * | 7/2007 | Aranyi | A61B 17/064 606/75 |
| 2008/0058704 A1 | 3/2008 | Hee et al. | |
| 2009/0005809 A1 * | 1/2009 | Hess | A61B 17/105 606/220 |
| 2009/0131979 A1 * | 5/2009 | Thompson | A61B 17/06066 606/224 |
| 2012/0130374 A1 * | 5/2012 | Bouduban | A61F 2/0811 606/75 |
| 2012/0191064 A1 | 7/2012 | Conston et al. | |
| 2012/0271272 A1 | 10/2012 | Hammack et al. | |
| 2013/0216623 A1 | 8/2013 | Yamamoto et al. | |
| 2013/0245600 A1 | 9/2013 | Yamamoto et al. | |
| 2015/0005794 A1 | 1/2015 | Whitehouse | |
| 2015/0133969 A1 * | 5/2015 | Gupta | A61B 17/0682 606/151 |
| 2015/0173751 A1 * | 6/2015 | Shelton, IV | A61B 17/0644 606/219 |
| 2015/0209180 A1 | 7/2015 | Prausnitz et al. | |
| 2015/0223977 A1 | 8/2015 | Oberkircher et al. | |
| 2015/0258120 A1 | 9/2015 | Zarnitsyn et al. | |
| 2015/0351958 A1 | 12/2015 | Contiliano et al. | |
| 2015/0351959 A1 | 12/2015 | Clem et al. | |
| 2016/0074211 A1 | 3/2016 | Ko et al. | |
| 2016/0074212 A1 | 3/2016 | Price et al. | |
| 2016/0074217 A1 | 3/2016 | Price et al. | |
| 2016/0081849 A1 | 3/2016 | Tsai et al. | |
| 2017/0095369 A1 | 4/2017 | Andino et al. | |
| 2017/0333416 A1 | 11/2017 | Zarnitsyn et al. | |
| 2017/0360606 A1 | 12/2017 | Price et al. | |
| 2017/0360607 A1 | 12/2017 | Price et al. | |
| 2018/0042765 A1 | 2/2018 | Noronha et al. | |

FOREIGN PATENT DOCUMENTS

| | | |
|---|---|---|
| WO | WO 2015/015467 A1 | 2/2015 |
| WO | WO 2017/042584 A1 | 3/2017 |

OTHER PUBLICATIONS

U.S. Appl. No. 62/351,620, filed Jun. 17, 2016.
First Chinese Office Action and Search Report dated Jun. 3, 2020 for Application No. 201780036922.X, 7 pages.
Extended European Search Report and Written Opinion dated Sep. 3, 2020 for Application No. 20175040.3, 6 pages.
Japanese Notification of Reasons for Refusal dated Aug. 12, 2020 for Application No. 2018-565689, 4 pages.

* cited by examiner

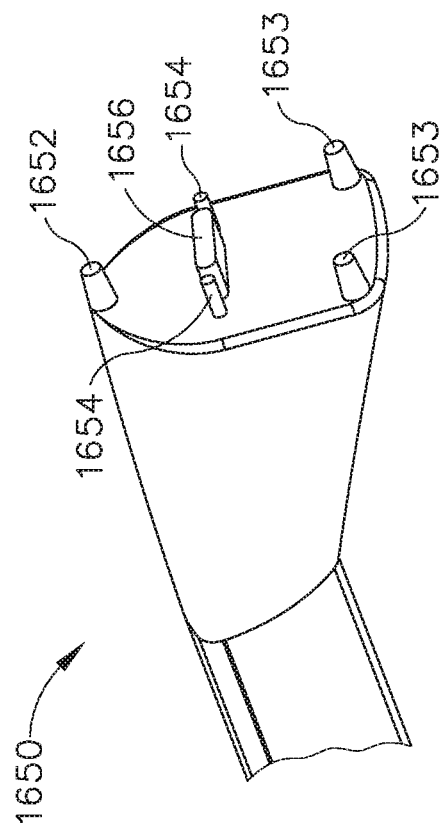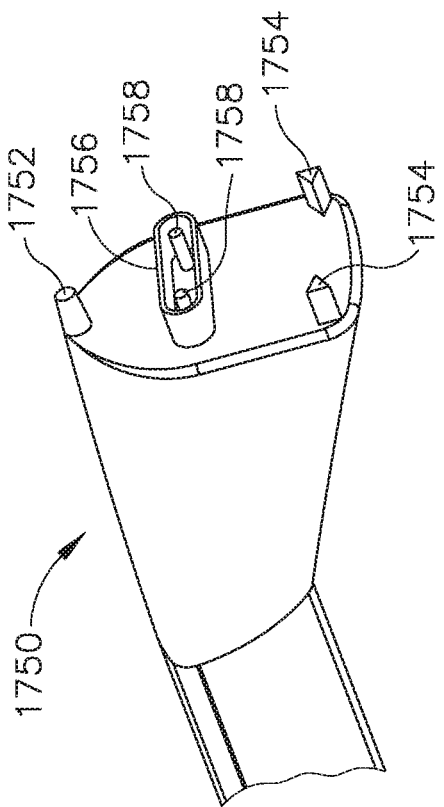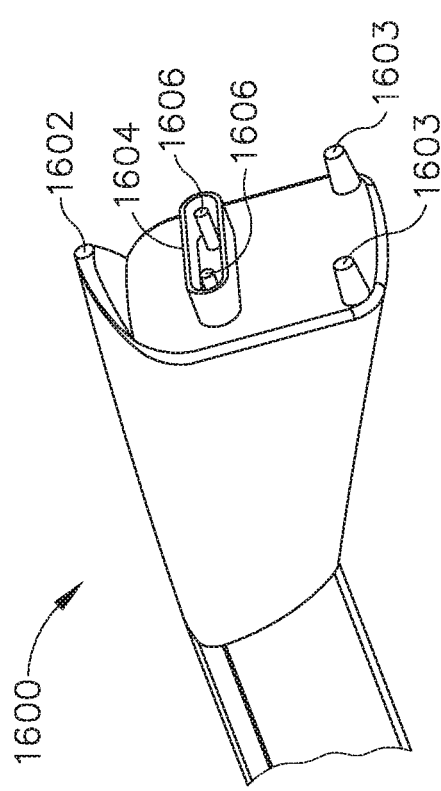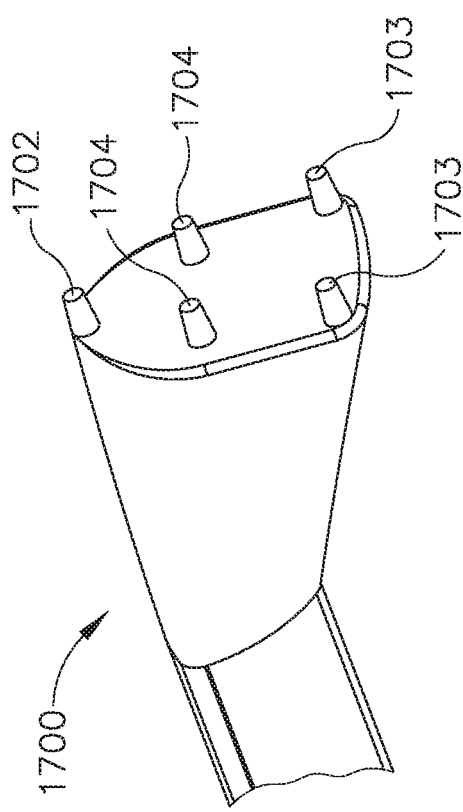

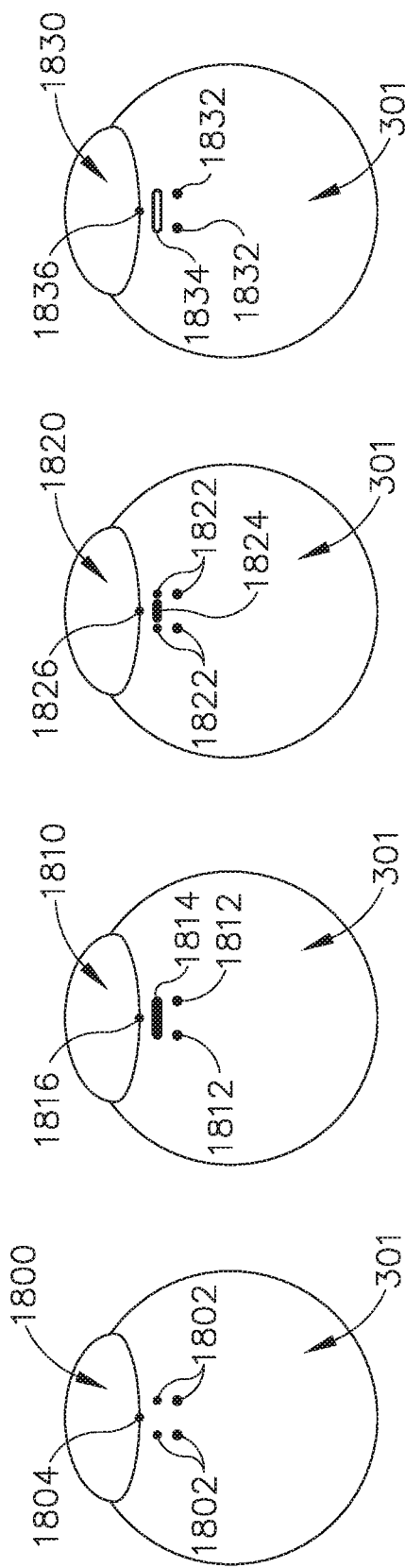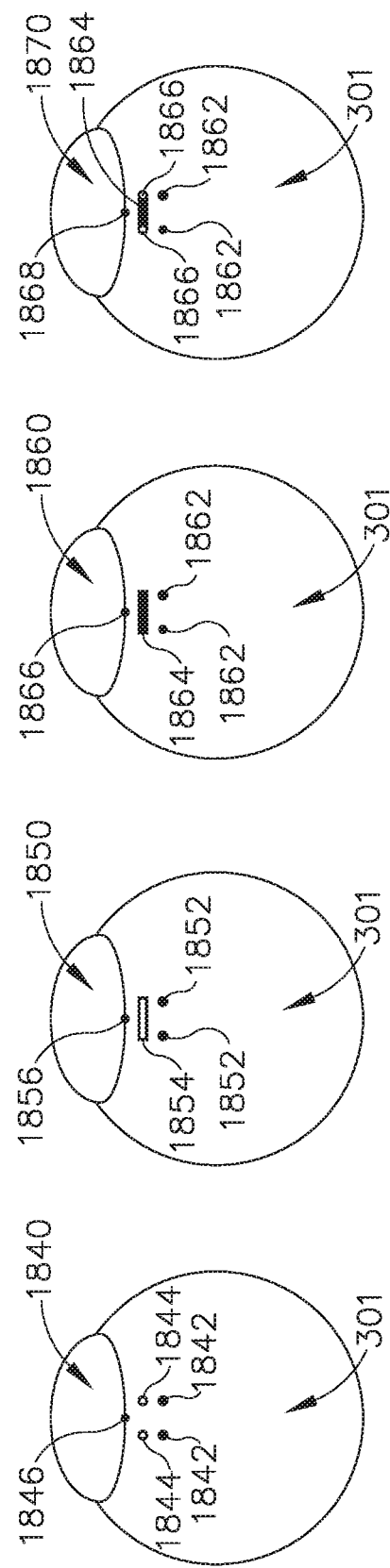

GUIDE APPARATUS FOR TANGENTIAL ENTRY INTO SUPRACHOROIDAL SPACE

PRIORITY

This application claims priority to U.S. Provisional Patent Application No. 62/351,620, entitled "Cannula Guide for Tangential Entry into Suprachoroidal Space," filed Jun. 17, 2016, the disclosure of which is incorporated by reference herein.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 44 depicts a perspective view of the distal end of an exemplary alternative marking instrument;

FIG. 45 depicts a perspective view of the distal end of another exemplary alternative marking instrument;

FIG. 46 depicts a perspective view of the distal end of another exemplary alternative marking instrument;

FIG. 47 depicts a perspective view of the distal end of another exemplary alternative marking instrument;

FIG. 48 depicts a schematic view of an eye of a patient, with an exemplary set of markings thereon;

FIG. 49 depicts a schematic view of an eye of a patient, with another exemplary set of markings thereon;

FIG. 50 depicts a schematic view of an eye of a patient, with another exemplary set of markings thereon;

FIG. 51 depicts a schematic view of an eye of a patient, with another exemplary set of markings thereon;

FIG. 52 depicts a schematic view of an eye of a patient, with another exemplary set of markings thereon;

FIG. 53 depicts a schematic view of an eye of a patient, with another exemplary set of markings thereon;

FIG. 54 depicts a schematic view of an eye of a patient, with another exemplary set of markings thereon; and FIG. 55 depicts a schematic view of an eye of a patient, with another exemplary set of markings thereon.

Figure 1:
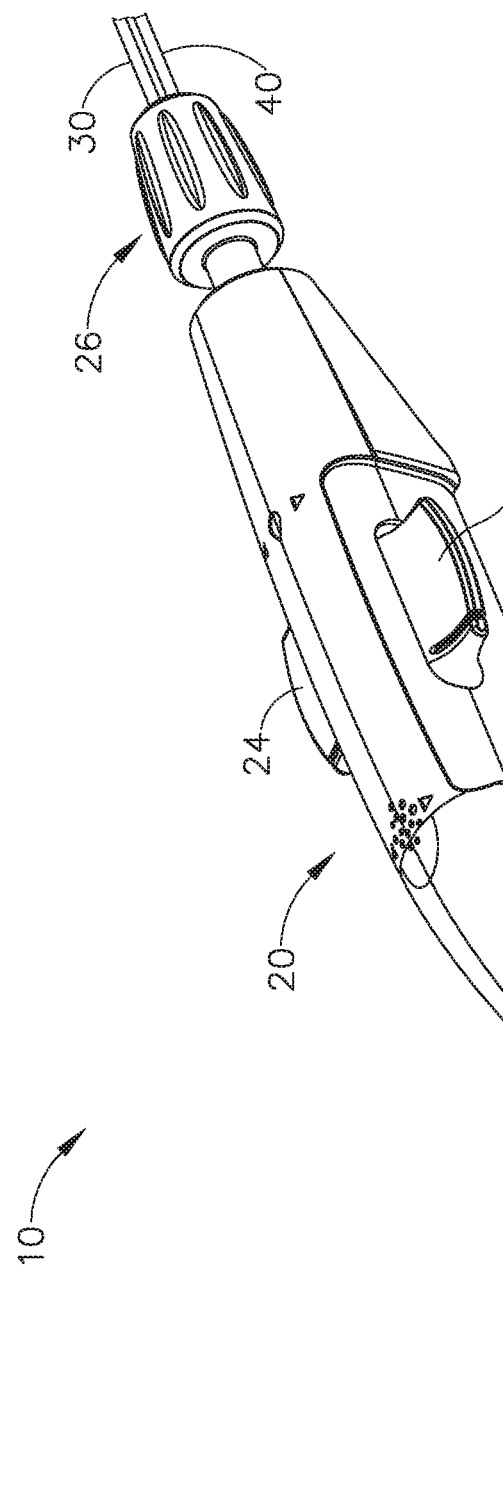
FIG. 1 depicts a perspective view of an exemplary instrument for subretinal administration of a therapeutic agent from a suprachoroidal approach.
Figure 2:
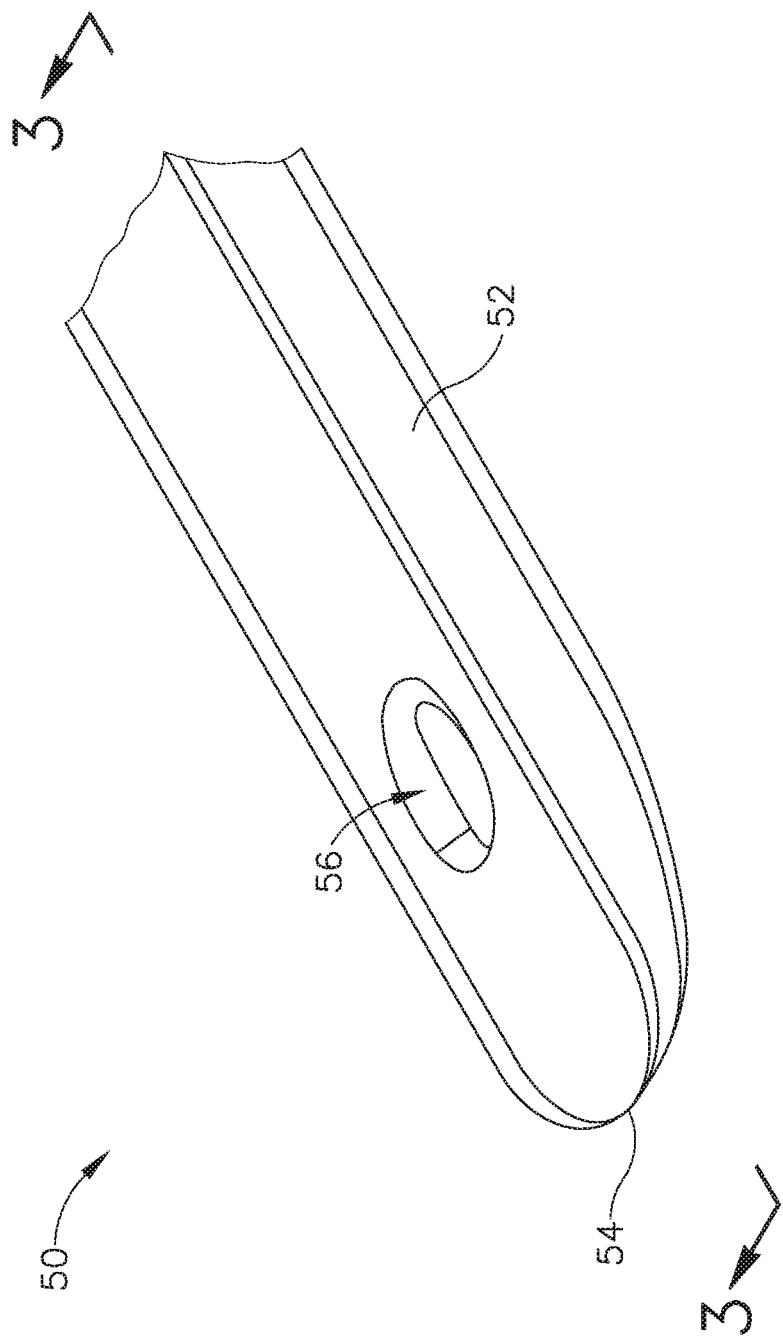
FIG. 2 depicts a perspective view of the distal end of an exemplary cannula that may be incorporated into the instrument of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument for Subretinal Administration of Therapeutic Agent

FIG. 1 shows an exemplary instrument (10) that is configured for use in a procedure for the subretinal administration of a therapeutic agent to an eye of a patient from a suprachoroidal approach. Instrument (10) comprises a body (20) and a flexible cannula (50) extending distally from body (20). Cannula (50) of the present example has a generally rectangular cross section, though any other suitable cross-sectional profile (e.g., elliptical, etc.) may be used. Cannula (50) is generally configured to support a needle (100) that is slidable within cannula (50), as will be described in greater detail below.

In the present example, cannula (50) comprises a flexible material such as Polyether block amide (PEBA), which may be manufactured under the trade name PEBAX. Of course, any other suitable material or combination of materials may be used. Also in the present example, cannula (50) has a cross-sectional profile dimension of approximately 2.0 mm by 0.8 mm, with a length of approximately 80 mm. Alternatively, any other suitable dimensions may be used. As will be described in greater detail below, cannula (50) is flexible enough to conform to specific structures and contours of the patient's eye, yet cannula (50) has sufficient column strength to permit advancement of cannula (50) between the sclera and choroid of patient's eye without buckling. By way of example only, cannula (50) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein.

Figure 3A:
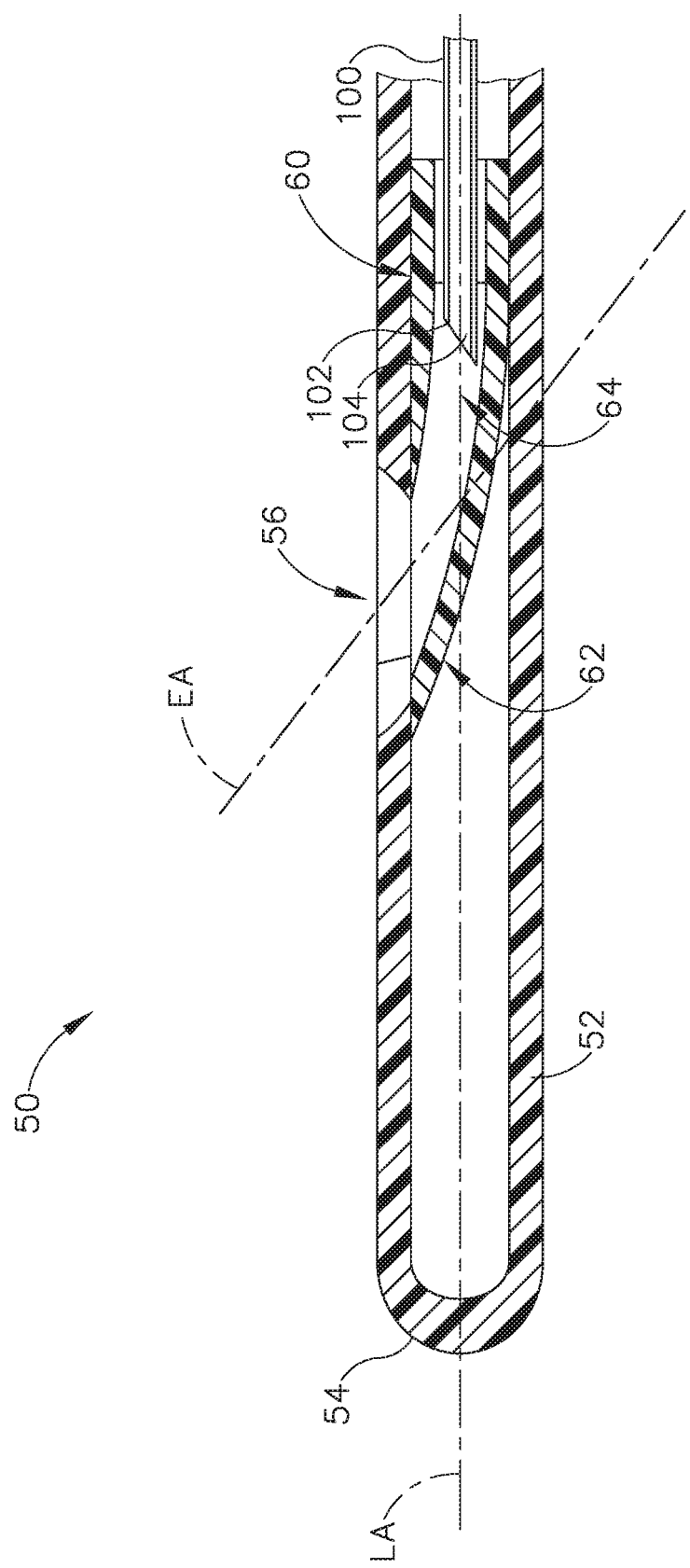
FIG. 3A depicts a cross-sectional side view of the cannula of FIG. 2, with the cross-section taken along line 3-3 of FIG. 2, with a needle in a first longitudinal position.
Figure 3B:
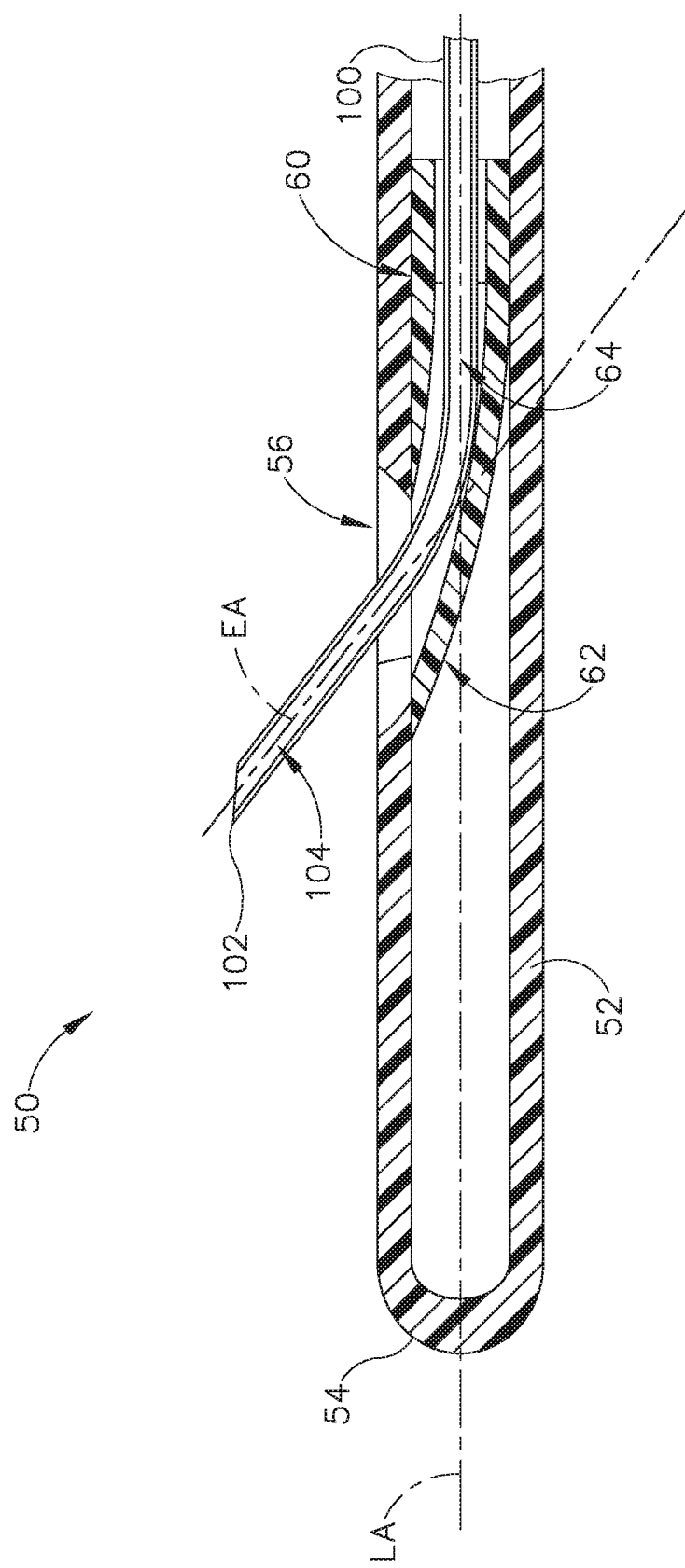
FIG. 3B depicts a cross-sectional side view of the cannula of FIG. 2, with the cross-section taken along line 3-3 of FIG. 2, with the needle in a second longitudinal position.

As can be seen in FIGS. 2-3B and 6, cannula (50) comprises a body (52), a closed distal end (54), and a lateral opening (56) that is located proximal to distal end (54). In the present example, distal end (54) has a rounded configuration. It should be understood that distal end (54) may have any suitable kind of curvature. It should also be understood that distal end (54) may have any other suitable kind of configuration (e.g., beveled, etc.). In the present example, distal end (54) is configured to provide separation between the sclera and choroid layers to enable cannula (50) to be advanced between such layers while not inflicting trauma to the sclera or choroid layers. Also in the present example, the region of body (52) that defines lateral opening (56) is beveled, as best seen in FIGS. 3A-3B. Alternatively, the edge of lateral opening (56) may have any other suitable configuration.

As best seen in FIGS. 3A-3B, a needle guide (60) is disposed within the hollow interior of cannula (50). By way of example only, needle guide (60) may be secured within cannula (50) by a press or interference fit, by adhesives, by mechanical locking mechanisms, and/or in any other suitable fashion. Needle guide (60) includes a curved distal end (62) that leads to lateral opening (56) of cannula (50), such that a lumen (64) of needle guide (60) distally terminates at lateral opening (56). The portion of needle guide (60) that is proximal to distal end (62) is substantially straight. Needle guide (60) may be formed of plastic, stainless steel, and/or any other suitable biocompatible material(s).

Needle (100) of the present example has a sharp distal tip (102) and defines a lumen (104). Distal tip (102) of the present example has a lancet configuration. In some other versions, distal tip (102) has a tri-bevel configuration or any other configuration as described in U.S. Pub. No. 2015/0223977, entitled "Method and Apparatus for Subretinal Administration of Therapeutic Agent," published Aug. 13, 2015, the disclosure of which is incorporated by reference herein. Still other suitable forms that distal tip (102) may take will be apparent to those of ordinary skill in the art in view of the teachings herein. Needle (100) of the present example comprises a stainless steel hypodermic needle that is sized to deliver the therapeutic agent while being small enough to minimize incidental trauma as needle (100) penetrates tissue structures of the patient's eye, as will be described in greater detail below. While stainless steel is used in the present example, it should be understood that any other suitable material(s) may be used, including but not limited to nitinol, etc.

By way of example only, needle (100) may be 35 gauge with a 100 µm inner diameter, although other suitable sizes may be used. For instance, the outer diameter of needle (100) may fall within the range of 27 gauge to 45 gauge; or more particularly within the range of 30 gauge to 42 gauge; or more particularly within the range of 32 gauge to 39 gauge. As another merely illustrative example, the inner diameter of needle (100) may fall within the range of approximately 50 µm to approximately 200 µm; or more particularly within the range of approximately 50 µm to approximately 150 µm; or more particularly within the range of approximately 75 µm to approximately 125 µm.

Needle (100) is slidably disposed within lumen (64) of needle guide (60). Needle guide (60) is generally configured to direct needle (100) upwardly along an exit axis (EA) that is obliquely oriented relative to the longitudinal axis (LA) of cannula (50) through lateral opening (56) of cannula (50).

This is shown in the sequence depicted in FIGS. 3A-3B, in which FIG. 3A shows needle (100) in a proximal position (where distal tip (102) of needle (100) is fully contained in lumen (64) of needle guide (60)); and FIG. 3B shows needle (100) in a distal position (where distal tip (102) of needle (100) is outside of needle guide (60)). While needle (100) is flexible, needle (100) of the present example is resiliently biased to assume a straight configuration. Thus, as shown in FIG. 3B, the portion of needle (100) that extends outside of cannula (50) and needle guide (60) is substantially straight, extending along exit axis (EA). In particular, at least a substantial length of the portion of needle (100) that extends outside of cannula (50) and needle guide (60) is coaxially aligned with exit axis (EA).

It should be understood that the depiction of exit axis (EA) in FIGS. 3A-3B may be somewhat exaggerated, for illustrative purposes only. In some versions, curved distal end (62) is configured to direct needle (100) along an exit axis (EA) that extends distally from cannula (50) at an angle of approximately 7° to approximately 9° relative to the longitudinal axis (LA) of cannula (50). It should be understood that such an angle may be desirable to deflect needle (100) in a direction to ensure penetration of needle into the choroid and to minimize the possibility of needle (100) continuing beneath the choroid through the suprachoroidal space (as opposed to penetrating through the choroid) and the possibility of retinal perforation. By way of further example only, curved distal portion (88) may urge needle (100) to exit cannula (50) along an exit axis (EA) that is oriented at an angle within the range of approximately 5° to approximately 30° relative to the longitudinal axis (LA) of cannula (50); or more particularly within the range of approximately 5° to approximately 20° relative to the longitudinal axis (LA) of cannula (50); or more particularly within the range of approximately 5° to approximately 10° relative to the longitudinal axis (LA) of cannula (50).

As shown in FIG. 1, instrument (10) of the present example further comprises an actuation knob (26) located at the proximal end of body (20). Actuation knob (26) is rotatable relative to body (20) to thereby selectively translate needle (100) longitudinally relative to cannula (50). In particular, actuation knob (26) is rotatable in a first angular direction to drive needle (100) distally relative to cannula (50); and in a second angular direction to drive needle (100) proximally relative to cannula (50). By way of example only, instrument (10) may provide such functionality through knob (26) in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Alternatively, any other suitable kind of actuation feature(s) may be used to drive needle (100) longitudinally relative to cannula (50).

In the present example, knob (26) is rotatable through a complete range of motion that corresponds to advancement of needle (100) to a position relative to cannula (50) to a predetermined amount of penetration within an eye of a patient. In other words, instrument (10) is configured such that an operator rotates knob (26) until knob (26) can no longer rotate, or until knob (26) begins to slip or "freewheel" in a clutch assembly, to properly position needle (100) within an eye of a patient. In some examples, the predetermined amount of advancement of needle (100) relative to cannula (50) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm.

In addition or in the alternative, instrument (10) may be equipped with certain tactile feedback features to indicate to an operator when needle (100) has been advanced to certain predetermined distances relative to cannula (50). Accordingly, an operator may determine the desired depth of penetration of needle (100) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

As also shown in FIG. 1, a pair of supply tubes (30, 40) extend proximally from actuator knob (26). In the present example, first supply tube (30) is configured to couple with a source of bleb fluid (340) (e.g., BSS); while second supply tube (40) is configured to couple with a source of therapeutic agent (341). It should be understood that each fluid supply tube (30, 40) may include a conventional luer feature and/or other structures permitting fluid supply tubes (30, 40) to be coupled with respective fluid sources. Fluid supply tubes (30, 40) lead to a valve assembly that includes actuation arms (24). Actuation arms (24) are pivotable to selectively change the state of the valve assembly. Based on the pivotal position of actuation arms (24), the valve assembly is operable to selectively pinch or otherwise open/close the supply of fluid from fluid supply tubes (30, 40) to lumen (104) of needle (100). Thus, actuation arms (24) are operable to selectively control the delivery of bleb fluid (340) and therapeutic agent (341) via needle (100). By way of example only, the valve assembly may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Other suitable features and configurations that may be used to control fluid delivery via needle (100) will be apparent to those of ordinary skill in the art in view of the teachings herein.

It should be understood that the features and operability of instrument (10) may be varied in numerous ways. By way of example only, needle (100) may be replaced with needle (200) as described in greater detail below. In addition, instrument (10) may be modified in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein. Other suitable modifications will be apparent to those of ordinary skill in the art in view of the teachings herein.

II. Exemplary Procedure for Subretinal Administration of Therapeutic Agent

FIGS. 4A-5C show an exemplary procedure for subretinal delivery of therapeutic agent from a suprachoroidal approach using instrument (10) described above. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 4A:
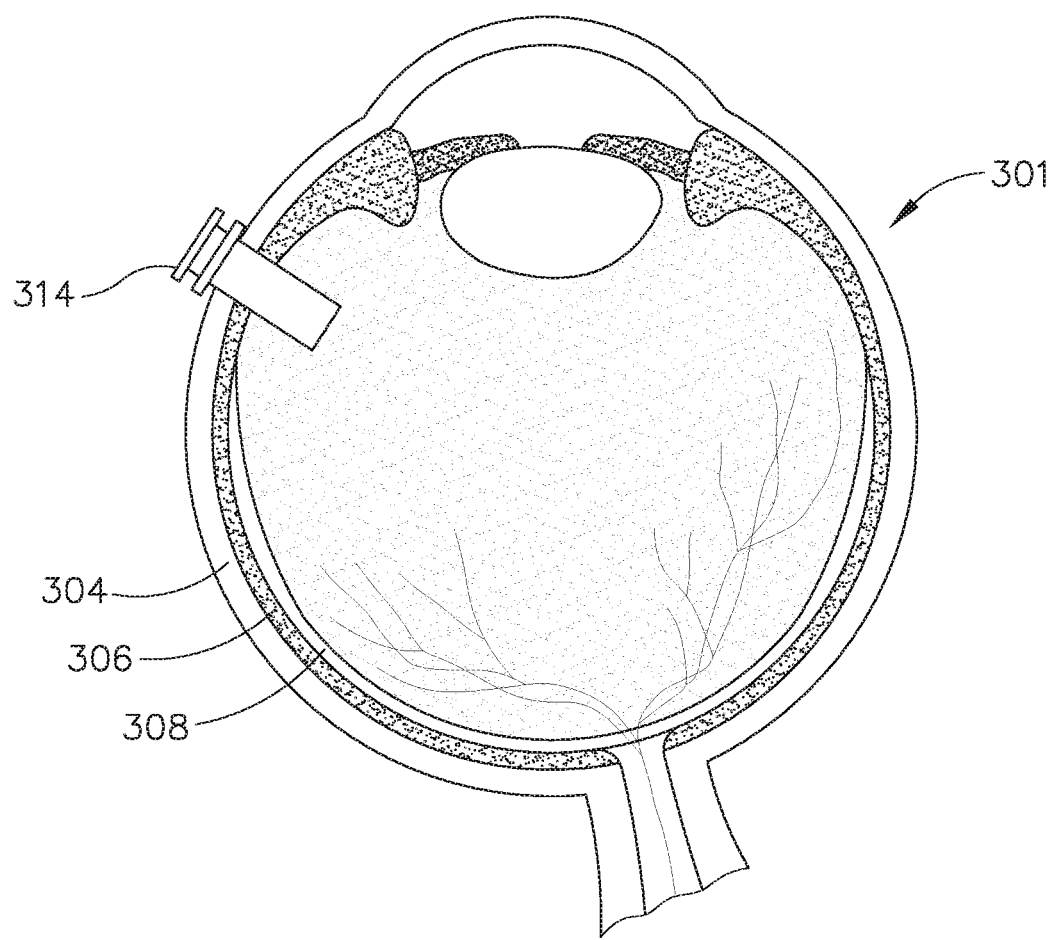
FIG. 4A depicts a cross-sectional view of an eye of a patient, with a chandelier installed in the eye.

In the present example, the procedure begins by an operator immobilizing tissue surrounding a patient's eye (301) (e.g., the eyelids) using a speculum, and/or any other instrument suitable for immobilization. While immobilization described herein with reference to tissue surrounding eye (301), it should be understood that eye (301) itself may remain free to move. Once the tissue surrounding eye (301) has been immobilized, an eye chandelier port (314) is inserted into eye (301), as shown in FIG. 4A, to provide intraocular illumination when the interior of eye (301) is viewed through the pupil. In the present example, eye chandelier port (314) is positioned in the inferior medial quadrant such that a superior temporal quadrant sclerotomy may be preformed. Eye chandelier port (314) is positioned to direct light onto the interior of eye (301) to illuminate at least a portion of the retina (e.g., including at least a portion of the macula). As will be understood, such illumination corresponds to an area of eye (301) that is being targeted for delivery of therapeutic agent.

In the present example, only chandelier port (314) is inserted at the stage shown in FIG. 4A, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. Although FIG. 4A shows a particular positioning of eye chandelier port (314), it should be understood that eye chandelier port (314) may have any other positioning as will be apparent to those of ordinary skill in the art in view of the teachings herein.

Figure 4B:
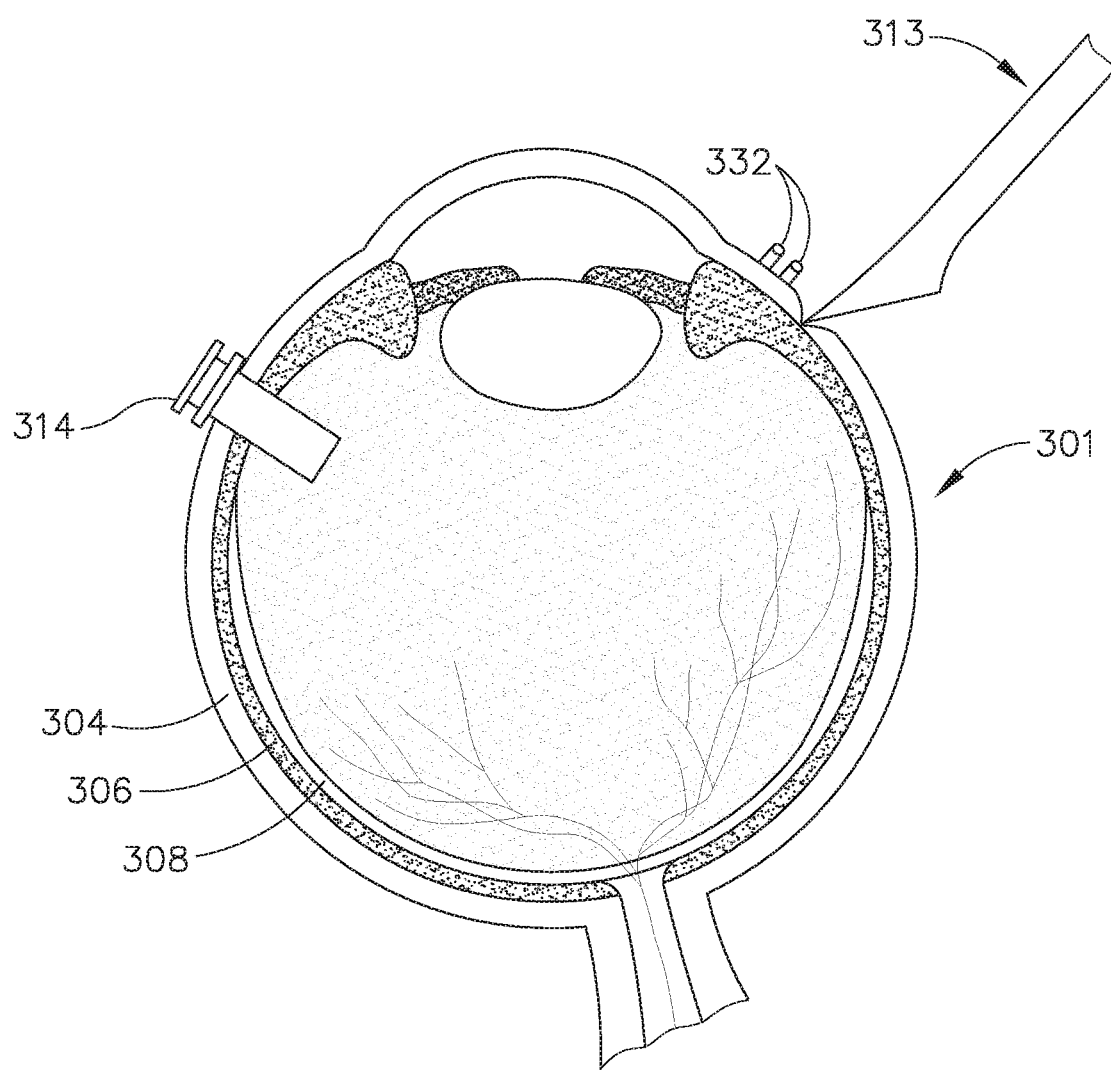
FIG. 4B depicts a cross-sectional view of the eye of FIG. 4A, with a suture loop attached to the eye, and with a sclerotomy being performed.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. A template may then be used to mark eye (301), as described in U.S. Pub. No. 2015/0223977, entitled "Method and Apparatus for Subretinal Administration of Therapeutic Agent," published Aug. 13, 2015, the disclosure of which is incorporated by reference herein. An operator may then use a visual guide created using the template to attach a suture loop assembly (332) and to perform a sclerotomy, as shown in FIG. 4B, using a conventional scalpel (313) or other suitable cutting instrument. The sclerotomy procedure forms a small incision through sclera (304) of eye (301). The sclerotomy is performed with particular care to avoid penetration of the choroid (306). Thus, the sclerotomy procedure provides access to the space between sclera (304) and choroid (306). Once the incision is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 4C:
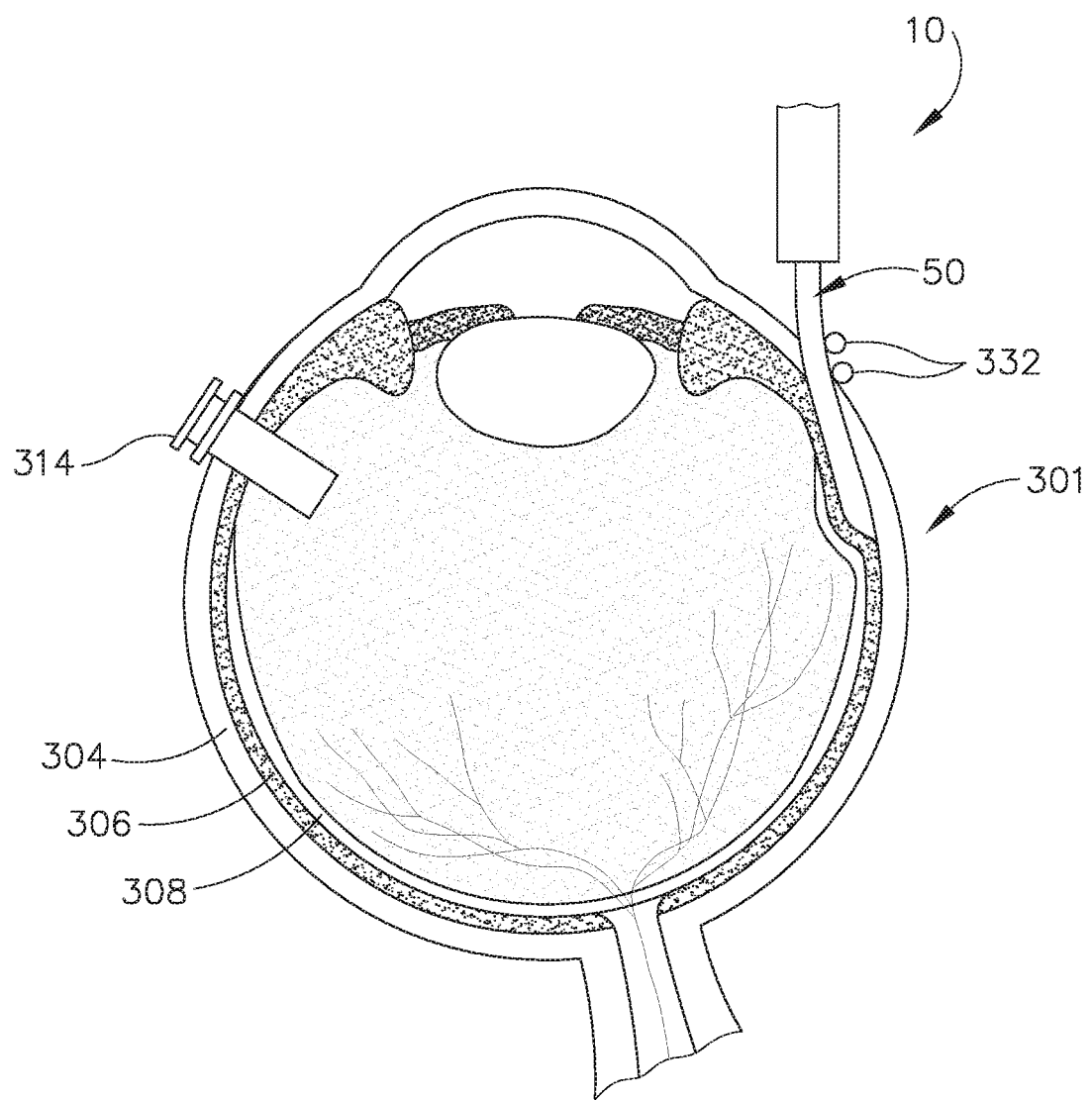
FIG. 4C depicts a cross-sectional view of the eye of FIG. 4A, with the instrument of FIG. 1 being inserted through the sclerotomy opening and in between the sclera and choroid of the eye.

With the sclerotomy procedure performed, an operator may insert cannula (50) of instrument (10) through incision (316) and into the space between sclera (304) and choroid (306). As can be seen in FIG. 4C, cannula (50) is directed through suture loop assembly (332) and into the incision. Suture loop assembly (332) may stabilize cannula (50) during insertion. Additionally, suture loop assembly (332) maintains cannula (50) in a generally tangential orientation relative to the incision. Such tangential orientation may reduce trauma as cannula (50) is guided through the incision. As cannula (50) is inserted into the incision through suture loop assembly (332), an operator may use forceps or other instruments to further guide cannula (50) along an atraumatic path. Of course, use of forceps or other instruments is merely optional, and may be omitted in some examples.

Although not shown, it should be understood that in some examples cannula (50) may include one or more markers on the surface of cannula (50) to indicate various depths of insertion. While merely optional, such markers may be desirable to aid an operator in identifying the proper depth of insertion as cannula (50) is guided along an atraumatic path. For instance, the operator may visually observe the position of such markers in relation to suture loop assembly (332) and/or in relation to the incision in the sclera (304) as an indication of the depth to which cannula (50) is inserted in eye (301). By way of example only, one such marker may correspond to an approximately 6 mm depth of insertion of cannula (50).

Figure 4D:
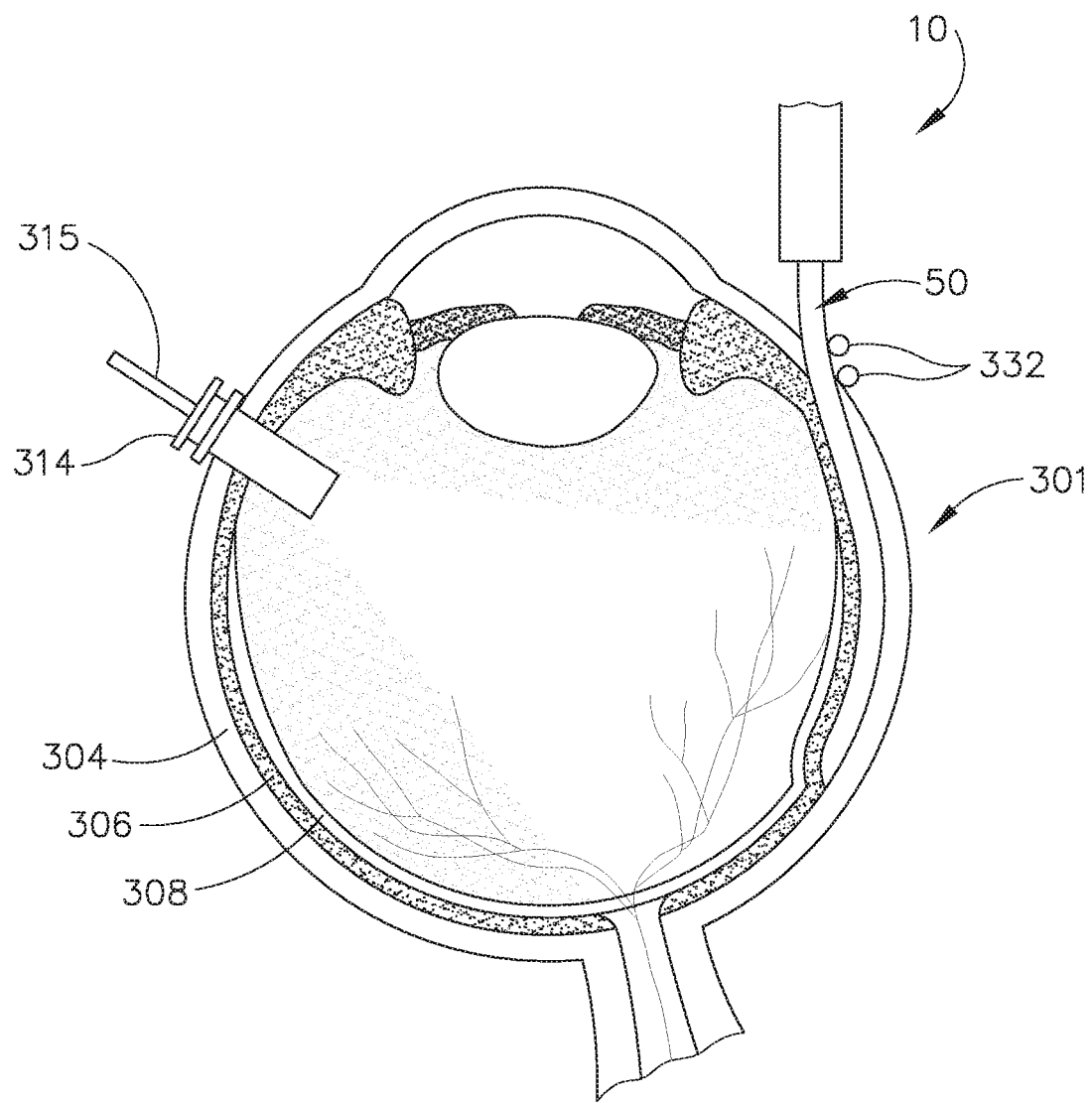
FIG. 4D depicts a cross-sectional view of the eye of FIG. 4A, with the instrument of FIG. 1 under direct visualization at the back of the eye, between the sclera and choroid.

As shown in FIG. 4D, once cannula (50) is at least partially inserted into eye (301), an operator may insert an optical fiber (315) into eye chandelier port (314) if the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (50) may optionally be made at this point to ensure proper positioning relative to the area of geographic atrophy of retina (308). In some instances, the operator may wish to rotate the eye (301), such as by pulling on suture loop assembly (332), to direct the pupil of the eye (301) toward the operator in order to optimize visualization of the interior of the eye (301) via the pupil.

FIGS. 4C-4D show cannula (50) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. By way of example only, the operator may rely on direct visualization through a microscope directed through the pupil of eye (301) as cannula (50) is being advanced through the range of motion shown in FIGS. 4C-4D, with illumination provided through fiber (315) and port (314). Cannula (50) may be at least partially visible through a retina (308) and choroid (306) of eye (301). Visual tracking may be enhanced in versions where an optical fiber is used to emit visible light through the distal end of cannula (50).

Figure 4E:
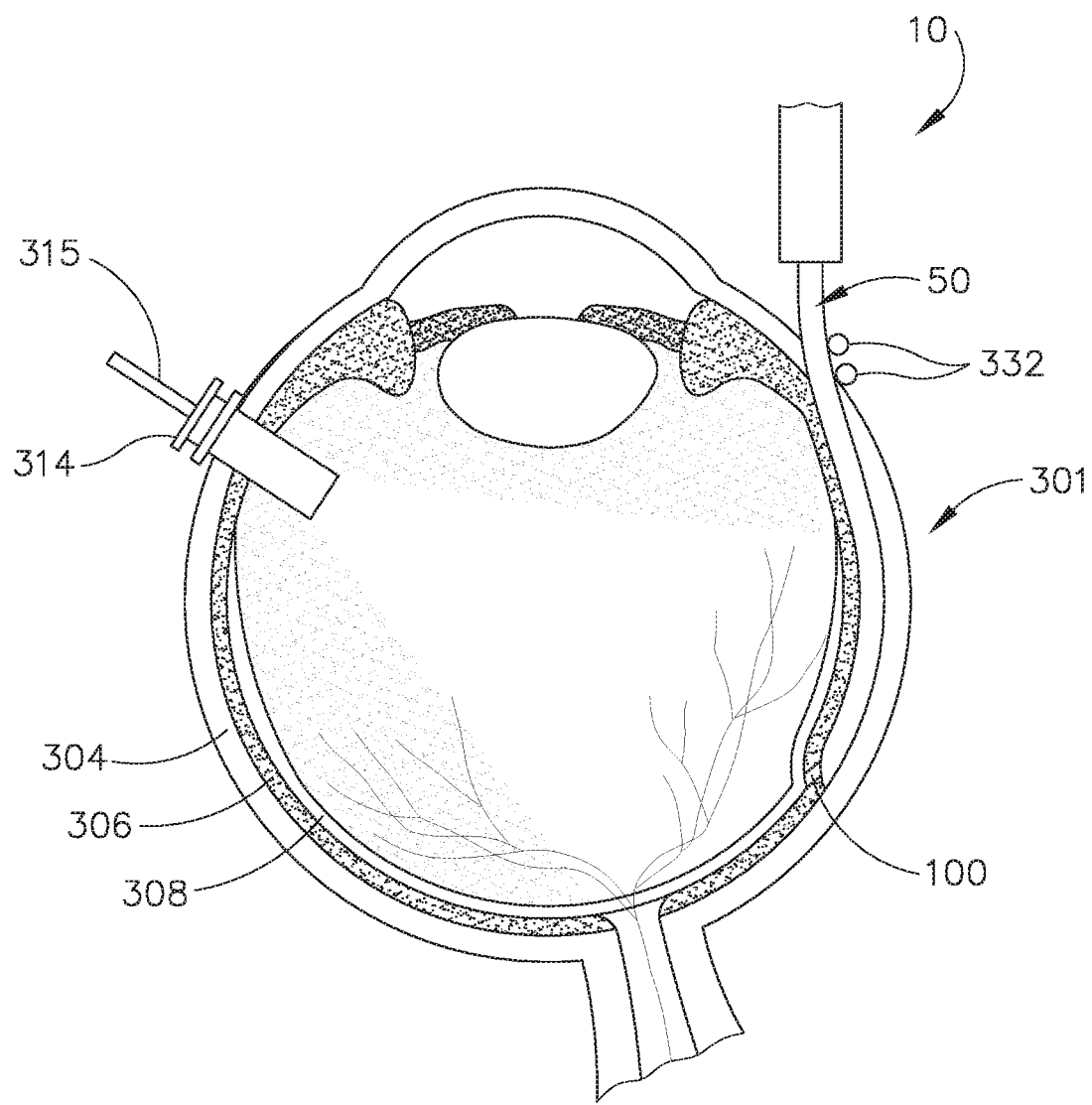
FIG. 4E depicts a cross-sectional view of the eye of FIG. 4A, with the needle of the instrument of FIG. 1 being advanced under direct visualization at the back of the eye, pressing against the outer surface of the choroid causing the choroid to "tent"
Figure 5A:
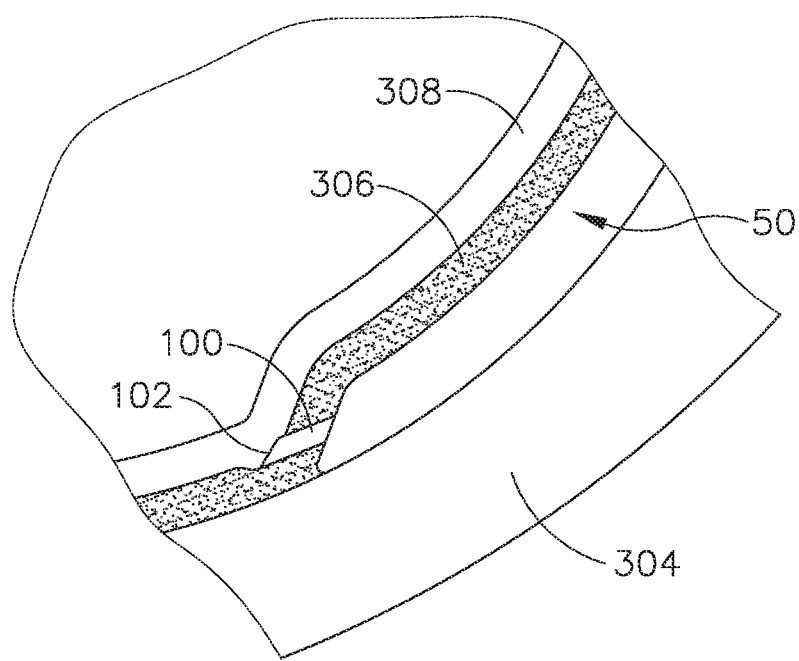
FIG. 5A depicts a detailed cross-sectional view of the eye of FIG. 4A depicted in the state shown in FIG. 4E.

Once cannula (50) has been advanced to the delivery site as shown in FIG. 4D, an operator may advance needle (100) of instrument (10) as described above by actuating knob (26). As can be seen in FIGS. 4E and 5A, needle (100) is advanced relative to cannula (50) such that needle (100) pierces through choroid (306) without penetrating retina (308). Immediately prior to penetrating choroid (306), needle (100) may appear under direct visualization as "tenting" the surface of choroid (306). In other words, needle (100) may deform choroid (306) by pushing upwardly on choroid (306), providing an appearance similar to a tent pole deforming the roof of a tent. Such a visual phenomenon may be used by an operator to identify whether choroid (306) is about to be pierced and the location of any eventual piercing. The particular amount of needle (100) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (100) advancement may be between approximately 0.25 mm and approximately 10 mm; or more particularly between approximately 2 mm and approximately 6 mm.

Figure 4F:
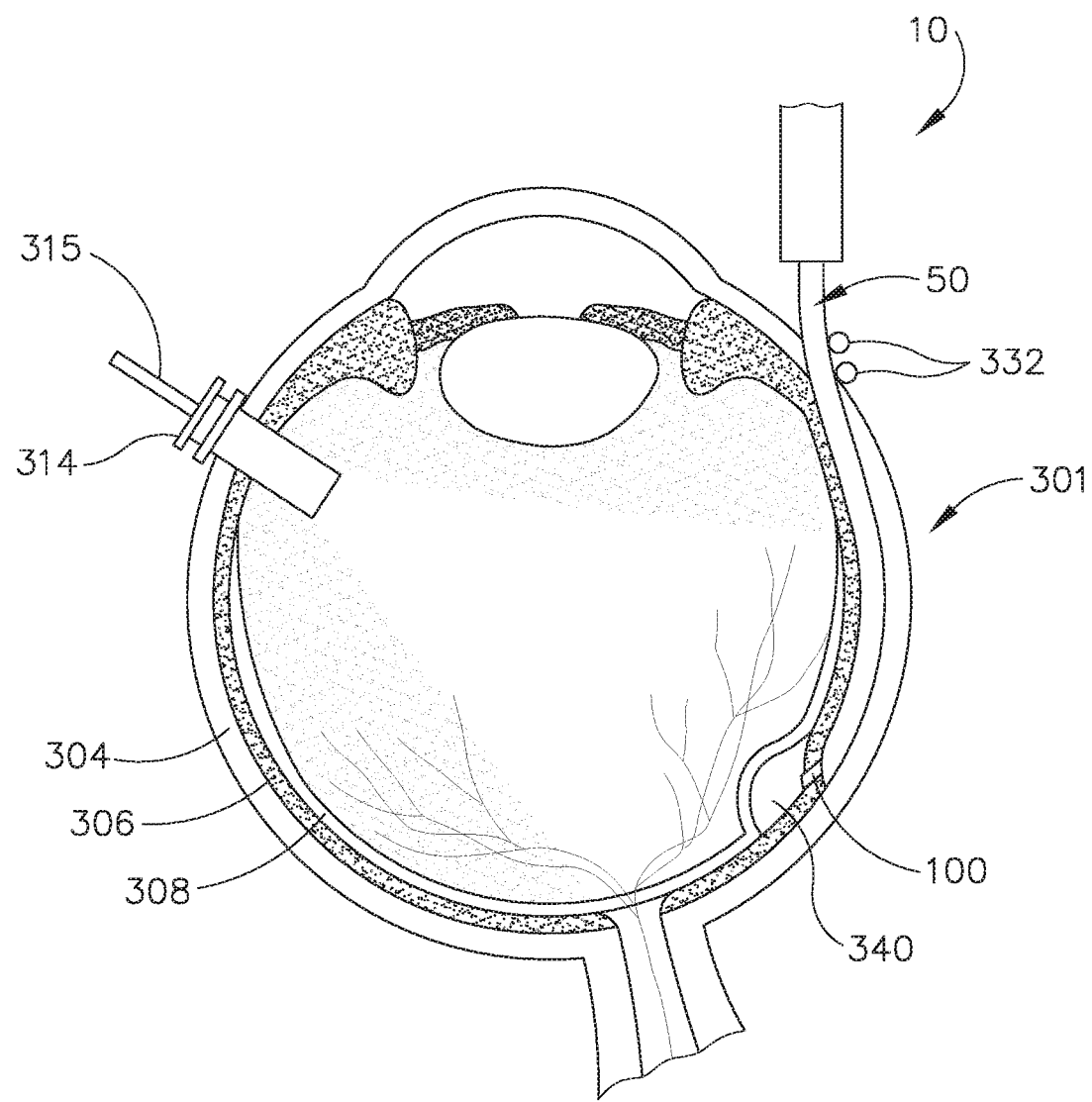
FIG. 4F depicts a cross-sectional view of the eye of FIG. 4A, with the needle dispensing a leading bleb under direct visualization at the back of the eye, the needle between the sclera and choroid, and the leading bleb in the subretinal space between the choroid and a retina.
Figure 5B:
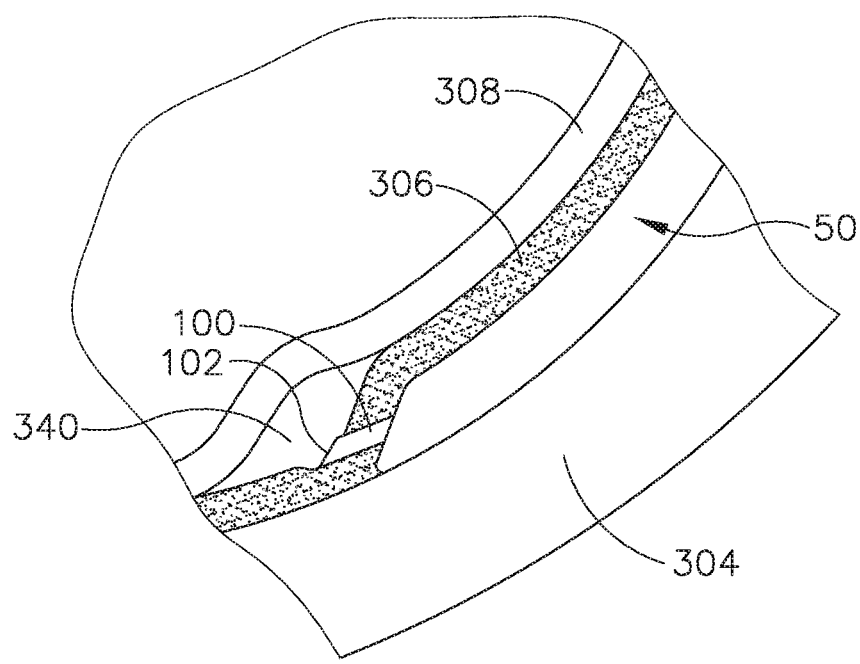
FIG. 5B depicts a detailed cross-sectional view of the eye of FIG. 4A depicted in the state shown in FIG. 4F.

In the present example, after the operator has confirmed that needle (100) has been properly advanced by visualizing the tenting effect described above, the operator infuses a balanced salt solution (BSS) or other similar solution as needle (100) is advanced relative to cannula (50). Such a BSS may form a leading bleb (340) ahead of needle (100) as needle (100) is advanced through choroid (306). Leading bleb (340) may be desirable for two reasons. First, as shown in FIGS. 4F and 5B, leading bleb (340) may provide a further visual indicator to an operator to indicate when needle (100) is properly positioned at the delivery site. Second, leading bleb (340) may provide a barrier between needle (100) and retina (308) once needle (100) has penetrated choroid (306). Such a barrier may push the retinal wall outwardly, thereby minimizing the risk of retinal perforation as needle (100) is advanced to the delivery site. In some versions, a foot pedal is actuated in order to drive leading bleb (340) out from needle (100). Alternatively, other suitable features that may be used to drive leading bleb (340) out from needle (100) will be apparent to those of ordinary skill in the art in view of the teachings herein.

Once the operator visualizes leading bleb (340), the operator may cease infusion of BSS, leaving a pocket of fluid as can be seen in FIGS. 4F and 5B. Next, a therapeutic agent (341) may be infused by actuating a syringe or other fluid delivery device as described in various references cited herein. The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, tissue plasminogen activators, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. In addition to, or as an alternative to, being used to deliver a therapeutic agent (341), instrument (10) and variations thereof may be used to provide drainage and/or perform other operations.

Figure 4G:
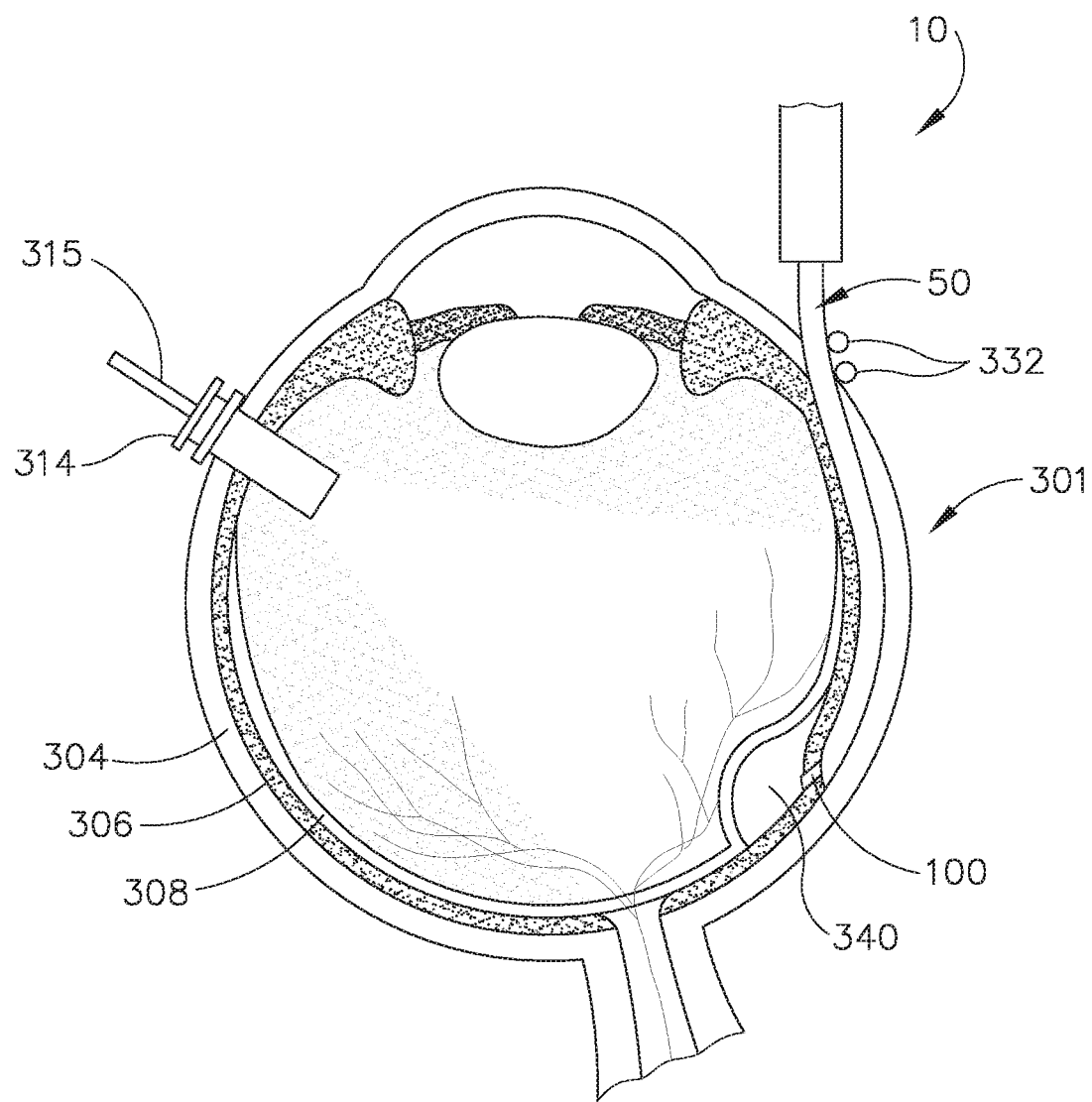
FIG. 4G depicts a cross-sectional view of the eye of FIG. 4A, with the needle dispensing a therapeutic agent to the eye at the back of the eye, between the sclera and choroid.
Figure 5C:
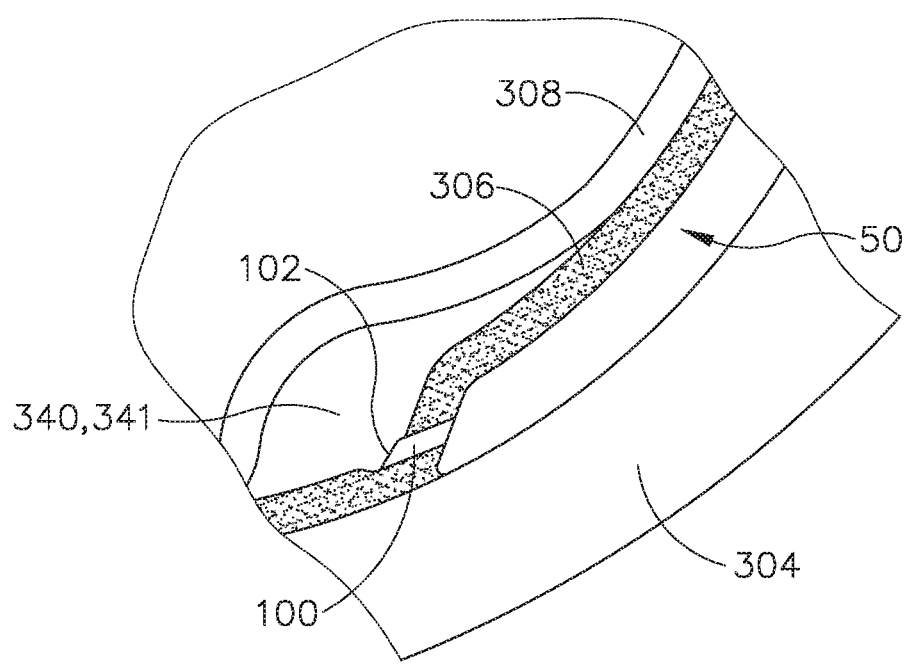
FIG. 5C depicts a detailed cross-sectional view of the eye of FIG. 4A depicted in the state shown in FIG. 4G.

In the present example, the amount of therapeutic agent (341) that is ultimately delivered to the delivery site is approximately 50 μL, although any other suitable amount may be delivered. In some versions, a foot pedal is actuated in order to drive agent (341) out from needle (100). Alternatively, other suitable features that may be used to drive agent (341) out from needle (100) will be apparent to those of ordinary skill in the art in view of the teachings herein. Delivery of therapeutic agent (341) may be visualized by an expansion of the pocket of fluid as can be seen in FIGS. 4G and 5C. As shown, therapeutic agent (341) essentially mixes with the fluid of leading bleb (340) as therapeutic agent (341) is injected into the surprachoroidal, subretinal space.

Once delivery is complete, needle (100) may be retracted by rotating knob (26) in a direction opposite to that used to advance needle (100); and cannula (50) may then be withdrawn from eye (301). It should be understood that because of the size of needle (100), the site where needle (100) penetrated through choroid (306) is self-sealing, such that no further steps need be taken to seal the delivery site through choroid (306). Suture loop assembly (332) and chandelier (314) may be removed, and the incision in the sclera (304) may be closed using any suitable conventional techniques.

As noted above, the foregoing procedure may be carried out to treat a patient having macular degeneration. In some such instances, the therapeutic agent (341) that is delivered by needle (100) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (100) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

It should also be understood that the procedure described above may be carried out in accordance with any of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein.

III. Exemplary Cannula Guides

As noted above, a suture loop assembly (332) may be installed in the eye (301) of a patient in order to stabilize and guide cannula (50) during insertion of cannula (50) into an incision (316) in the eye (301). Those of ordinary skill in the art will recognize that the formation of suture loop assembly (332) may be somewhat time consuming. In addition, it may be difficult to provide consistent spacing between the suture loops of a suture loop assembly (332); and between the suture loops and the eye (301). Such variations in spacing may yield variations in the entry angle and/or variations in the force required to insert cannula (50) through suture loop assembly (332). It may therefore be desirable to provide a device that provides the stabilizing and guiding functionality of suture loop assembly (332); yet that is faster and easier to install in the eye (301) than suture loop assembly (332), yielding more consistent results. Various illustrative examples of such devices are described in greater detail below. These devices described below may provide faster installation times, minimize variability due to surgeon technique, and require a lower level of expertise such that less surgeon training will be necessary. At the end of the procedure, the device may be removed from the eye such that no foreign body will be left in the eye.

A. Overview

Figure 6:
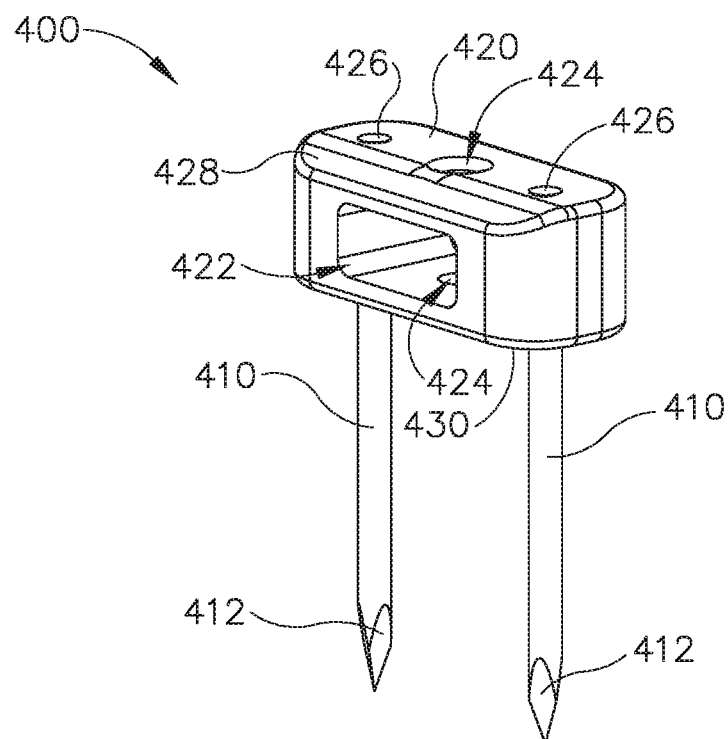
FIG. 6 depicts a perspective view of an exemplary guide tack that may be used to guide the cannula of FIG. 2 during performance of the procedure shown in FIGS. 4A-4G and 5A-5C.
Figure 7:
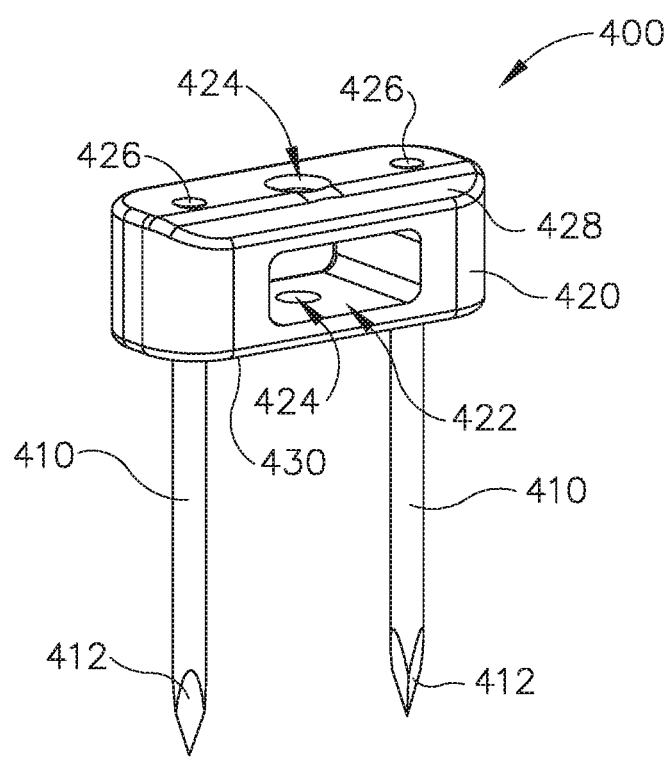
FIG. 7 depicts another perspective view of the guide tack of FIG. 6.

FIGS. 6-7 show an exemplary guide tack (400) that may be used to guide cannula (50) through an incision (316) in the eye (301), instead of using suture loop assembly (332). Guide tack (400) of the present example comprises a head (420) with a pair of legs (410) extending downwardly from head (420). Guide tack (400) thus resembles an unformed staple. Head (420) may be colored or otherwise marked to provide a high degree of contrast between head (420) and the sclera (304). This may promote easy visualization of head (420) when guide tack (400) is installed in the eye (301) as described below.

The free end of each leg (410) includes a sharp tip (412). By way of example only, legs (410) may be configured and operable similar to conventional vitrectomy trocars. By way of further example only, legs (410) may have a size corresponding to between 25 gauge and 30 gauge. In the present example, legs (410) extend from head (420) for a distance of approximately 3 mm. Such a leg (410) length may provide enough length to ensure sufficient retention of legs (410) in the eye (301) while minimizing the risk of contact with interior anatomy within the eye (301).

Sharp tips (412) enable legs (410) to pierce through the eye (301) such that tips (412) reach the vitreous chamber of the eye (301). Once legs (410) are inserted in the eye (310) friction may secure guide tack (400) to eye such that guide tack (400) is substantially anchored to the eye (301); yet enable guide tack (400) to be removed from the eye (301) without causing damage beyond the puncture sites created by legs (410). Moreover, the puncture sites created by legs (410) may be small enough to be self-sealing after removal of guide tack (400) from the eye (301), such that no sutures are needed to seal the puncture sites. An exemplary instrument and procedure that may be employed to install guide tack (400) on the eye (301) will be described in greater detail below.

Head (420) of the present example defines a guide opening (422), a set of retainer pin openings (424), and a chamfer (428). Guide opening (422) is oriented along an axis that is transverse to the plane defined between legs (410). Guide pin opening (424) is dimensioned to slidably yet snugly receive cannula (50) as will be described in greater detail below. Retainer pin openings (424) are oriented along an axis that is parallel to the longitudinal axes of legs (410). Retainer pin openings (424) are dimensioned to receive a retainer pin of a deployment instrument, as will also be described in greater detail below.

Chamfer (428) is configured to facilitate visualization of the site of a sclerotomy adjacent to guide tack (400), as will be described in greater detail below. While only one chamfer (428) is provided in the present example, along only one of the upper edges of head (420), some variations may provide two chamfers (428), along both of the upper edges of head (420). Such dual chamfers may provide a symmetric configuration of head (420) (i.e., symmetry about a lateral axis) and further reduce the risk of head (420) impeding the view of the operator.

In some versions, the inner walls defining guide opening (422) are configured to provide a uniform cross-sectional size of guide opening (422) along the full depth of guide opening (422). In some other versions, the inner walls defining guide opening (422) are configured to provide a tapering profile in guide opening (422). Such a tapering profile may provide a larger guide opening (422) size at the end of guide opening (422) where cannula (50) is inserted; and a smaller guide opening (422) size at the end of guide opening (422) where cannula (50) exits. In such versions, chamfer (428) may be located at the side of head (420) corresponding to the smaller guide opening (422) size. In such versions, the operator may be instructed to orient guide tack (400) (or instrument (500) may be preloaded with guide tack (400)) such that chamfer (428) will be on the side closest to the sclerotomy (514) as described below. This will help ensure that the smaller guide opening (422) size is located on the side of guide tack (400) where cannula (50) will exit guide tack (400).

As also shown in FIGS. 6-7, the upper ends (426) of legs (410) are exposed relative to the top surface of head (420). In the present example, legs (410) are formed of a ferrous material (e.g., stainless steel, etc.), such that the exposed upper ends (426) may engage magnets of a deployment instrument as will be described in greater detail below. By way of example only, guide tack (400) may be formed by molding head (420) out of a plastic material around the upper regions of legs (410). Various suitable materials and techniques that may be used to form guide tack (400) will be apparent to those of ordinary skill in the art in view of the teachings herein.

Figure 8A:
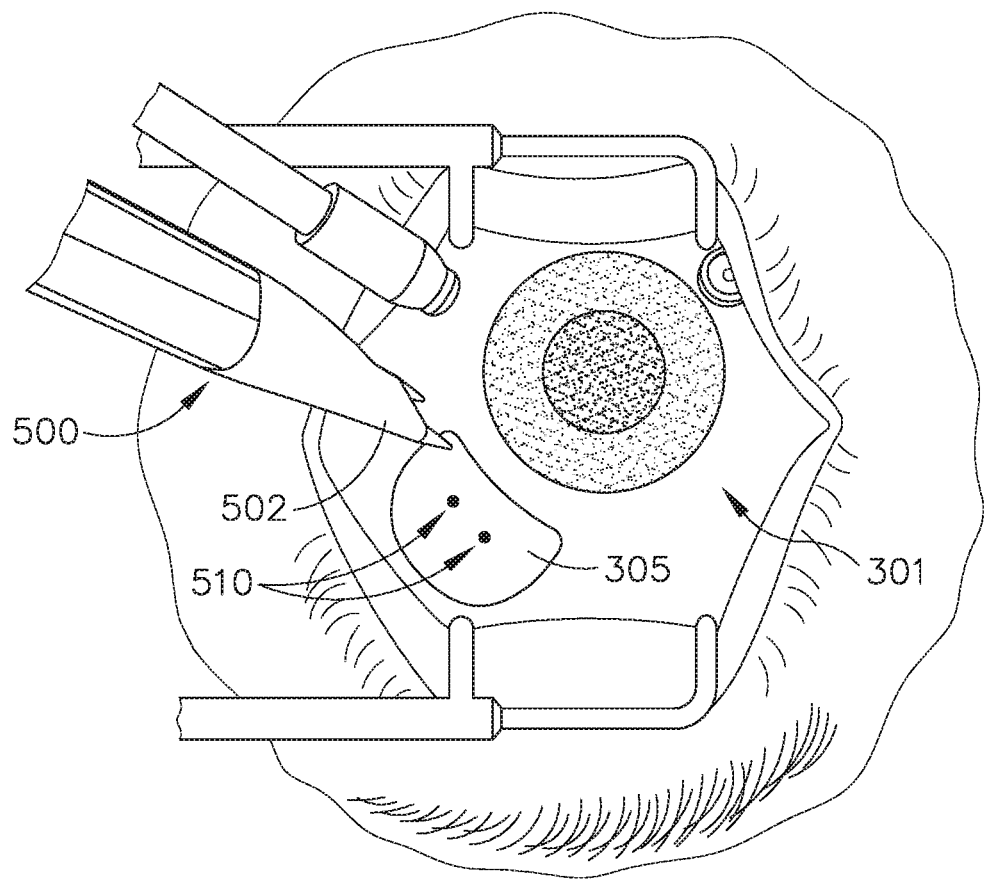
FIG. 8A depicts a top plan view of an eye of a patient, with a first end of a marking and deployment instrument being used to mark a guide tack deployment site on the eye.

FIGS. 8A-8E show an exemplary procedure in which guide tack (400) is used to guide cannula (50) into a patient's eye (301) in order to reach the position shown in FIGS. 4D-4G and 5A-5C, to perform the steps shown in FIGS. 4D-4G and 5A-5C as described above. As shown in FIG. 8A, the sclera of the patient's eye (301) is accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. A first end (502) of a marking and deployment instrument (500) is pressed against exposed surface (305) to apply a pair of marks (510) to exposed surface (305). By way of example only, a pigment material may be first applied to first end (502) (e.g., by pressing first end (502) against an ink pad), such that first end (502) leaves some of the pigment on exposed surface (305) to provide marks (510). Various exemplary configurations that may be used for marking and deployment instrument (500) will be described in greater detail below. In the present example, marks (510) are located on the pars plana region of the eye (301). In some versions, marking features of first end (502) are also configured to facilitate location of the pars plana region, by enabling the operator to identify the appropriate spacing from the limbus of the eye (301) corresponding to the location of the pars plana.

Figure 8B:
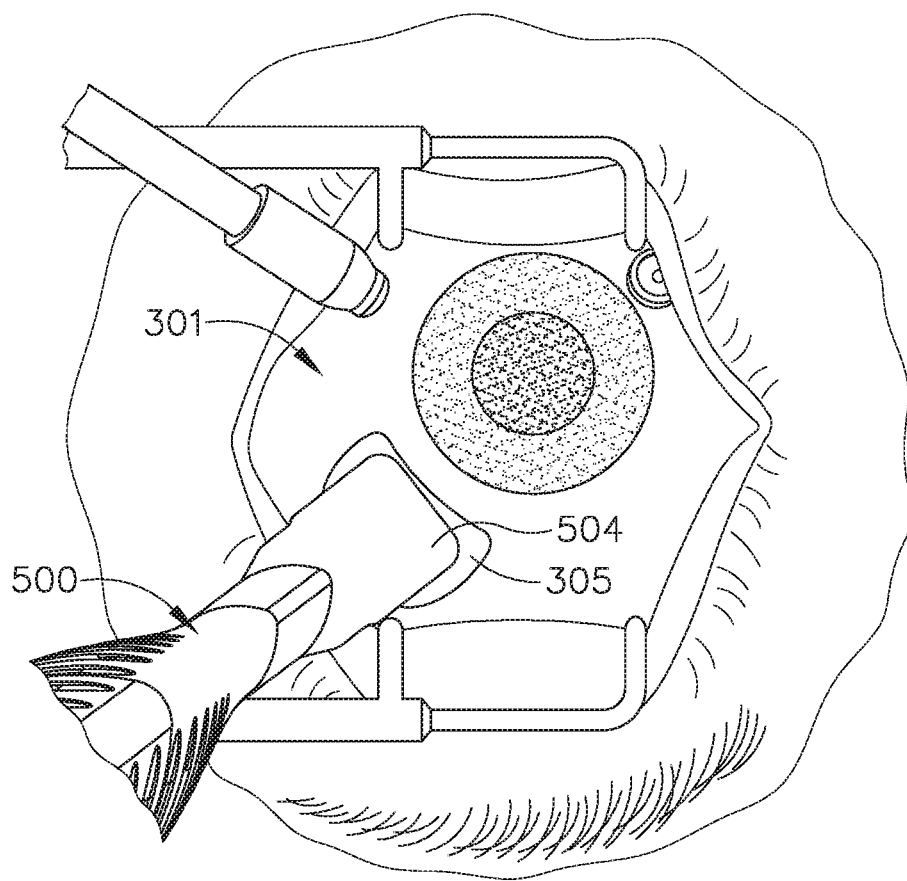
FIG. 8B depicts a top plan view of the eye of FIG. 8A, with a second end of the marking and deployment instrument of FIG. 8A being used to deploy a guide tack in the eye while marking a sclerotomy site on the eye.

As shown in FIG. 8B, the operator may then use a second end (504) of marking and deployment instrument (500) to install guide tack (400) in eye (301). In particular, the operator may align tips (412) with marks (510) and then press guide tack (400) toward eye (301), thereby piercing eye (301) with tips (412). The operator may further urge guide tack (400) toward eye (301) until the underside (430) of head (420) abuts exposed surface (305). The abutment of underside (430) with exposed surface (305) will ensure consistent spacing between guide opening (422) and surface (305), such that the spacing should not vary from procedure to procedure.

Figure 8C:
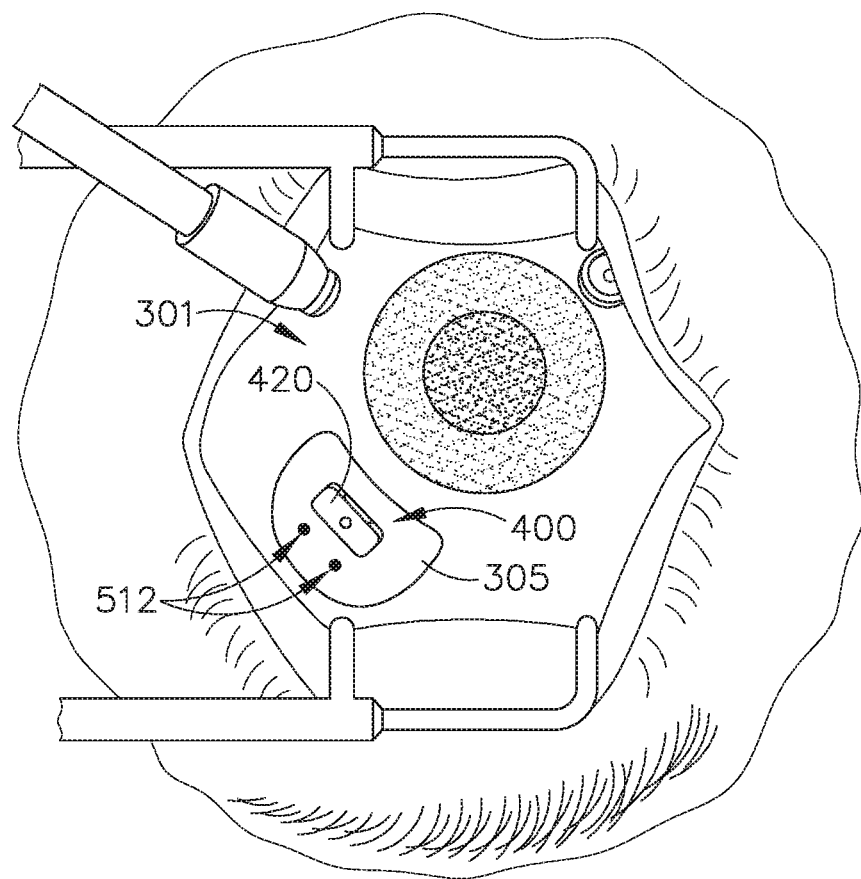
FIG. 8C depicts a top plan view of the eye of FIG. 8A, with the guide tack of FIG. 6 deployed in the eye, and with a sclerotomy site mark on the eye.

As shown in FIG. 8C, when the operator removes marking and deployment instrument (500), guide tack (400) is anchored to the eye (301). Also, a pair of additional marks (512) are left on exposed surface (305). In the present example, and as will be described in greater detail below, second end (504) of marking and deployment instrument (500) includes a pair of marking elements next to the structure on which guide tack (400) is removably mounted, such that second end (504) applies marks (512) to the eye (301) while simultaneously deploying guide tack (400) in the eye (301).

Figure 8D:
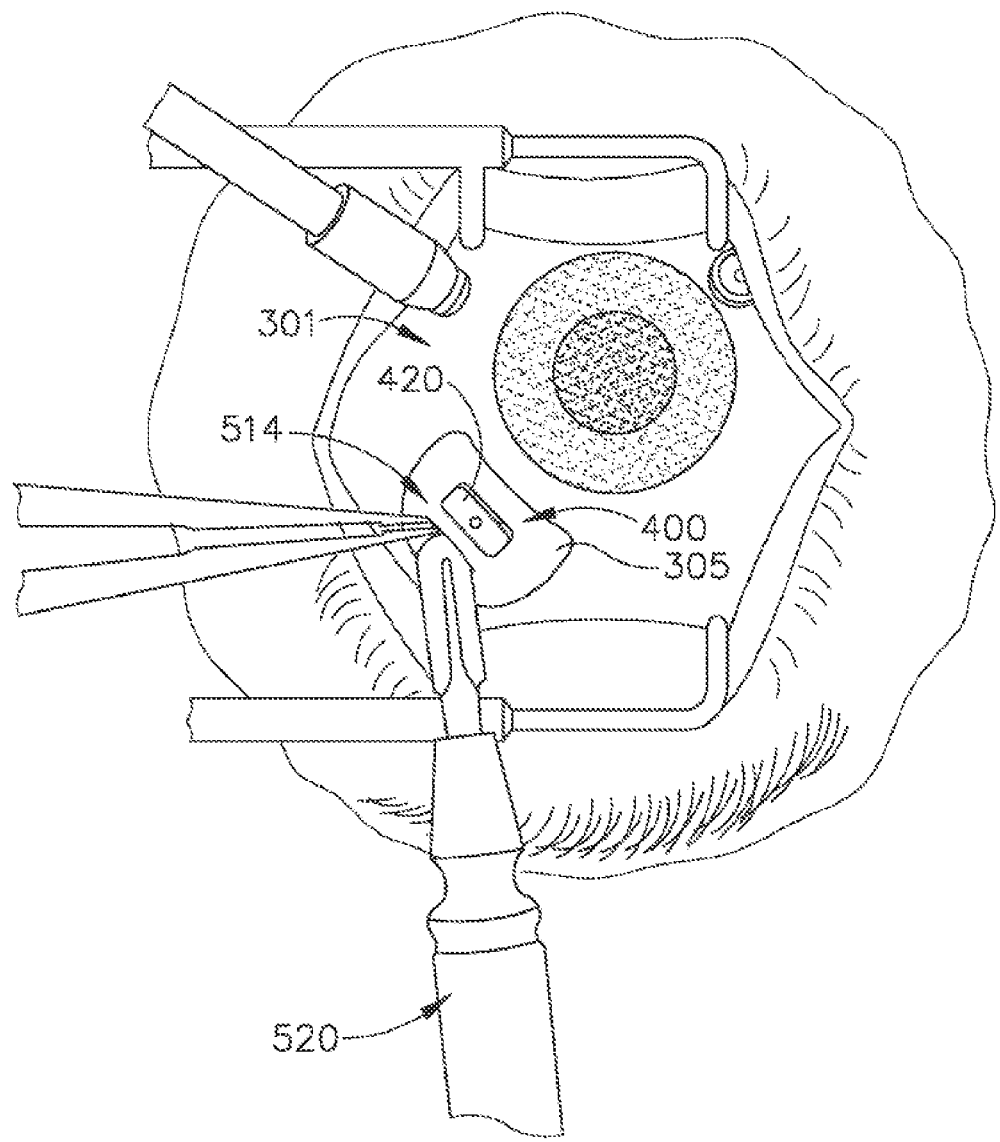
FIG. 8D depicts a top plan view of the eye of FIG. 8A, with a sclerotomy being provided at the sclerotomy site of FIG. 8C.

As shown in FIG. 8D, the operator then uses a conventional scalpel (520) to form a sclerotomy (514). The sclerotomy (514) is formed between marks (512), such that marks (512) are used to identify the ends of the sclerotomy (514). By way of example only, the sclerotomy (514) may be approximately 3 mm long, extending center-to-center between marks (512). The sclerotomy (514) extends through the full scleral thickness, removing all scleral fibers. The sclerotomy (514) is performed with particular care to avoid penetration of the choroid (306). Thus, the sclerotomy procedure provides access to the space between sclera (304) and choroid (306). Once the sclerotomy (514) is made in the eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 8E:
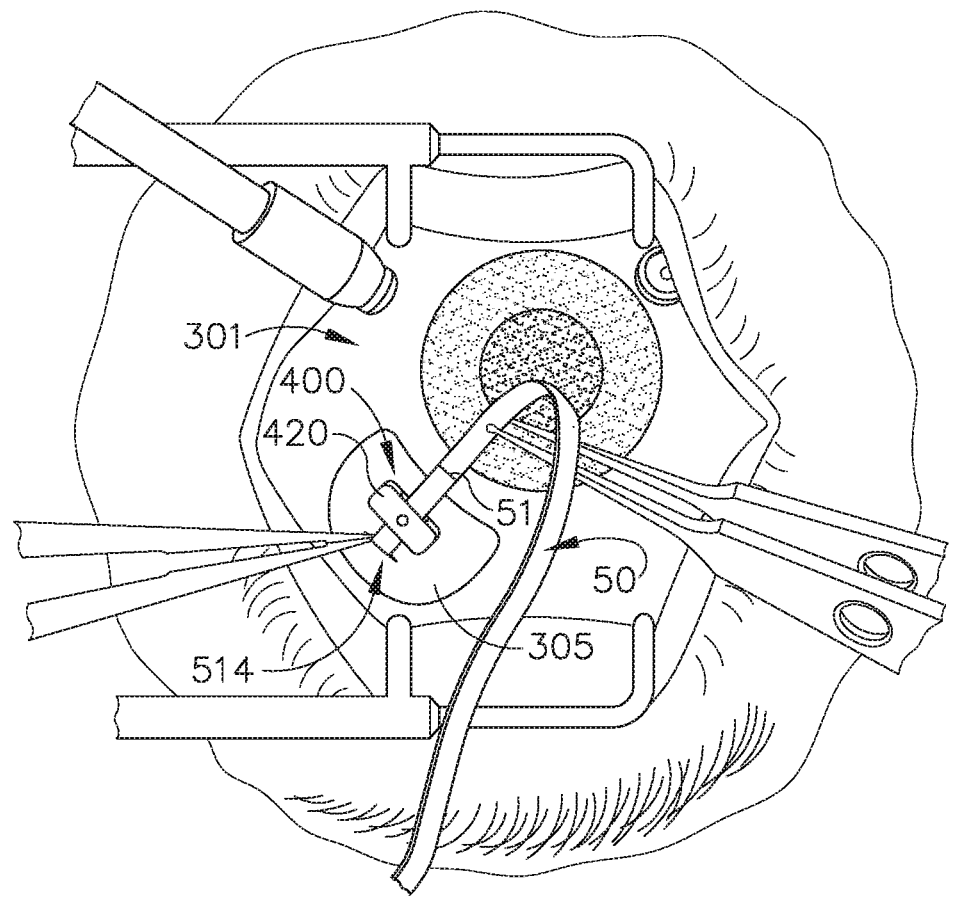
FIG. 8E depicts a top plan view of the eye of FIG. 8A, with the cannula of FIG. 2 being guided into the sclerotomy of FIG. 8D via the guide tack of FIG. 6.
Figure 9:
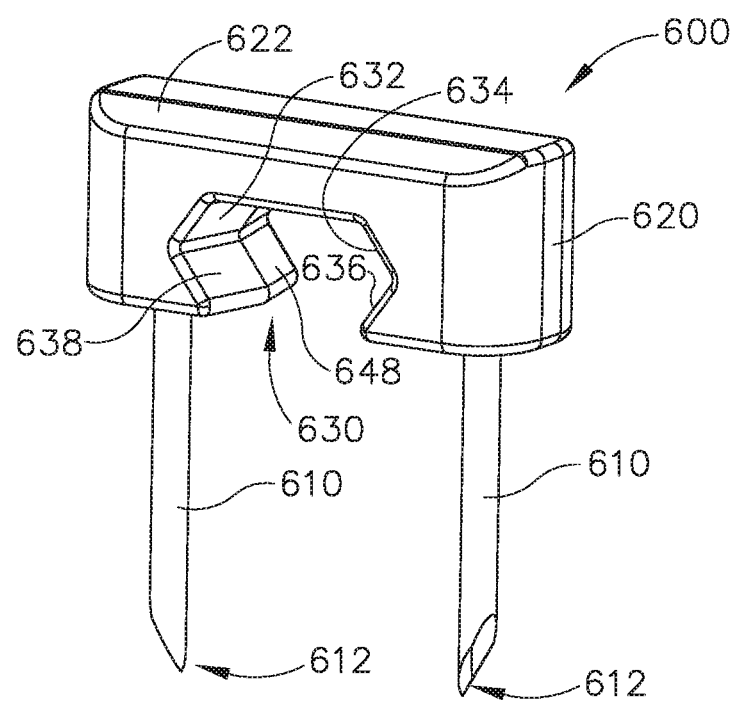
FIG. 9 depicts a perspective view of an exemplary alternative guide tack that may be used to guide the cannula of FIG. 2 during performance of the procedure shown in FIGS. 4A-4G, 5A-5C, and 8A-8E.
Figure 10:
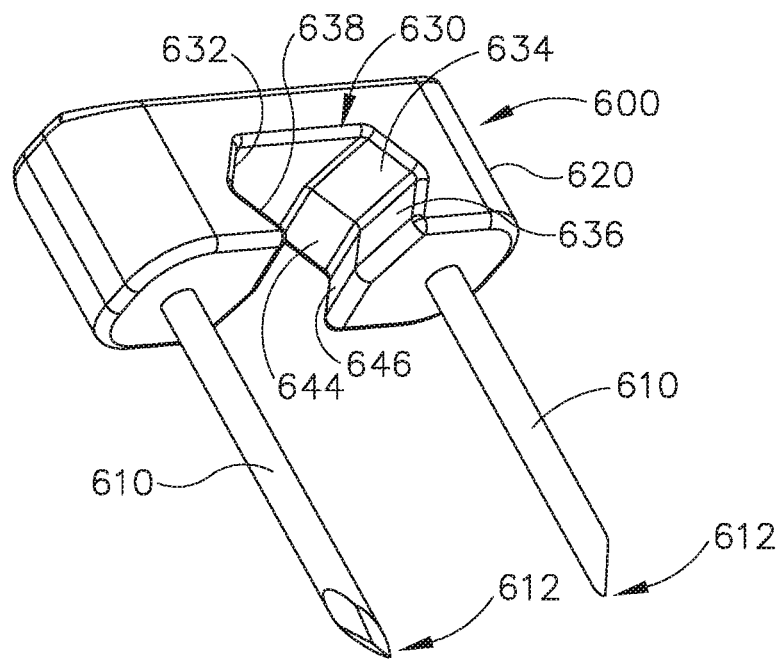
FIG. 10 depicts another perspective view of the guide tack of FIG. 9.

After the sclerotomy (514) is formed, and as shown in FIG. 8E, cannula (50) is passed through guide opening (422) of guide tack (400) and then through the sclerotomy (514). In particular, cannula (50) is inserted into the space between the sclera (304) and the choroid (306). As described above, guide tack (400) may stabilize cannula (50). Additionally, guide tack (400) maintains cannula (50) in a generally tangential orientation relative to sclerotomy (514). Such tangential orientation may reduce trauma as cannula (50) is guided through sclerotomy (514) to stabilize cannula (50) and to prevent damage to surrounding tissue. As cannula (50) is inserted into sclerotomy (514) through guide tack (400), the operator may use forceps or other instruments to further guide cannula (50) along an atraumatic path. Of course, use of forceps or other instruments is merely optional, and may be omitted in some examples.

As also shown in FIG. 8E, cannula (50) of the present example further includes a depth marker (51) on the outer surface of cannula (50). Depth marker (51) is configured such that the operator may visually observe the position of depth marker (51) in relation to guide tack (400) or in relation to the sclerotomy (514) to determine when cannula (50) has been inserted to a predetermined insertion depth. By way of example only, depth marker (510) may be positioned to correspond with an initial cannula (50) insertion depth of approximately 5 mm in relation to the sclerotomy (514). While cannula (50) only has one depth marker (51) in the present example, alternative versions may include more than one depth marker (51).

As yet another merely illustrative variation, cannula (50) may include an outwardly protruding depth stop feature that abuts guide tack (400) to physically restrict the depth of insertion of cannula (50) in the eye (301). In some such versions, the depth stop feature is configured to enable selective positioning of the depth stop feature along the length of cannula (50), such that the operator may select a desired depth of insertion before passing cannula (50) through guide opening (420). Again, one or more depth markers (51) may be used to assist the operator in selecting a position for an adjustable depth stop feature along the length of cannula (50). Various suitable forms that a depth stop feature may take will be apparent to those of ordinary skill in the art in view of the teachings herein.

After reaching the state shown in FIG. 8E, and after cannula (50) has been inserted into the eye (301) to an appropriate depth, the procedure may continue as described above with reference to FIGS. 4D-4G and 5A-5C. After the therapeutic agent (341) is injected into the suprachoroidal, subretinal space, cannula (50) may be withdrawn from the eye (301) and guide tack (400) may also be removed from the eye (301). The sclerotomy (514) may then be closed using any suitable conventional techniques. As noted above, the site where needle (100) penetrated through choroid (306) is self-sealing, such that no further steps need be taken to seal the delivery site through choroid (306). As also noted above, the sites where legs (510) penetrated through the eye (301) are also self-sealing, such that no further steps need be taken to seal the puncture sites where legs (510) were inserted.

B. Guide Tack Variations

FIGS. 9-10 and 13-14 show another exemplary guide tack (600) that may be used in place of guide tack (400) described above. Except as otherwise described below, guide tack (600) of this example may be configured and operable just like guide tack (400). Guide tack (600) of this example includes a head (620) with a pair of legs (610) extending downwardly from head (620).

Figure 11:
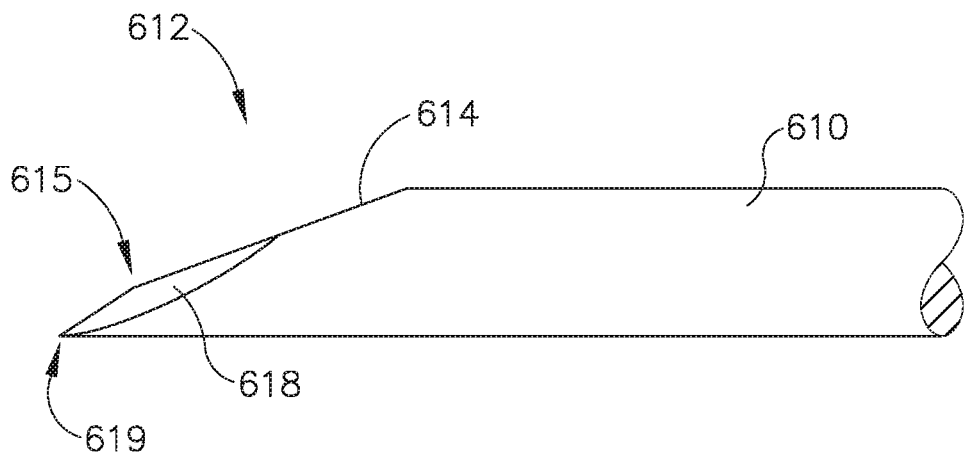
FIG. 11 depicts a front elevational view of a distal portion of a leg of the guide tack of FIG. 9.
Figure 12:
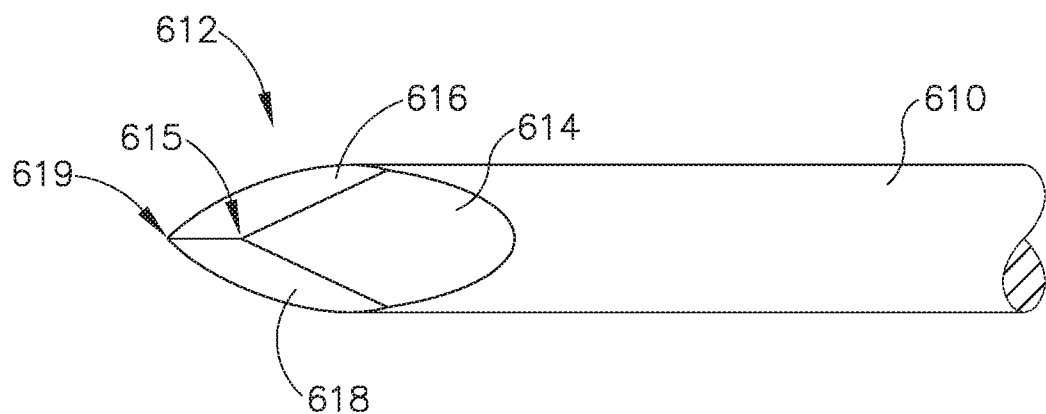
FIG. 12 depicts a side elevational view of a distal portion of a leg of the guide tack of FIG. 9.
Figure 13:
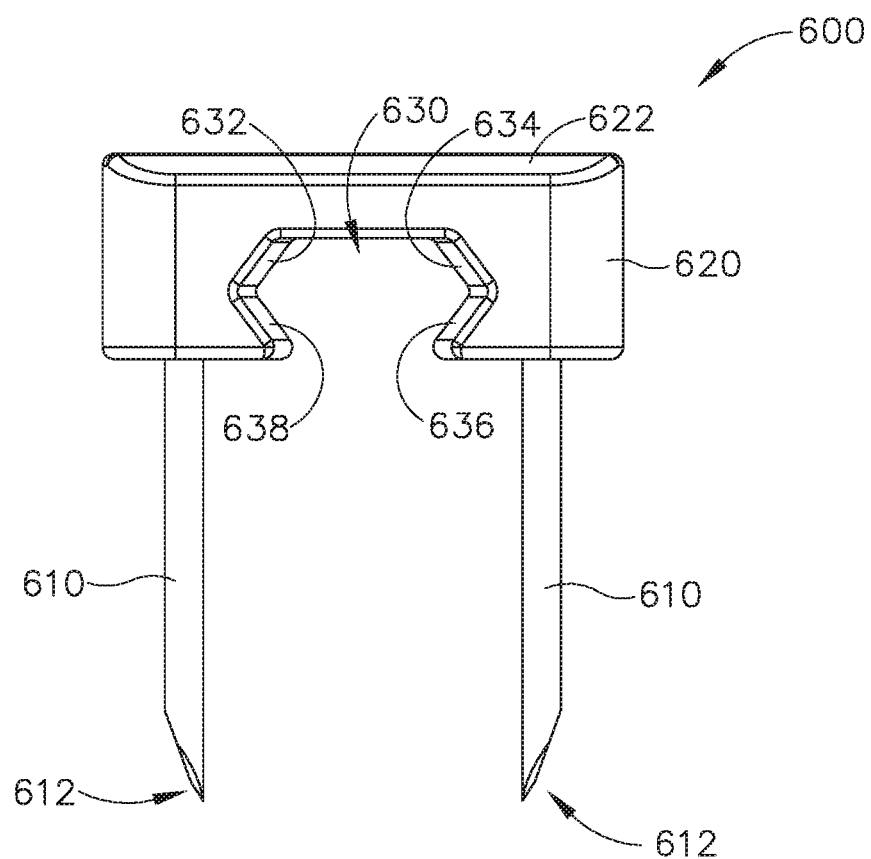
FIG. 13 depicts a front elevational view of the guide tack of FIG. 9.

The free end of each leg (610) includes a sharp tip (612). As best seen in FIGS. 11-12, each sharp tip (612) has a tri-bevel configuration. In particular, sharp tip (612) includes a proximal facet (614) and a pair of distal facets (616, 618). All three facets (614, 616, 618) converge together at a first point (615), while distal facets (616, 618) also converge at a second point (619). This tri-bevel configuration promotes relatively easy piercing of the eye (301) as the operator urges sharp tips (612) into the eye (301). Alternatively, sharp tips (612) may have any other suitable configuration that enables sharp tips (612) to pierce the tissue layers of the eye (301), including but not limited to various eye-piercing tip configurations known in the art. Legs (610) may otherwise be configured just like legs (410) described above. It should also be understood that the sharp tips of the legs of any of the other guide tacks described herein may have the same tri-bevel configuration that sharp tips (612) have.

Head (620) of the present example defines a guide opening (630) and a chamfer (622). While not shown, head (620) may also include a retainer pin opening similar to retainer pin opening (424) described above. In addition, while not shown, the upper ends of legs (610) may be exposed at the top surface of head (620). Moreover, while only one chamfer (622) is shown, head (620) may instead have two chamfers (622) as described herein. Guide opening (630) is sized and configured to slidably receive cannula (50). Guide opening (630) is oriented along an axis that is transverse to the plane defined between legs (610). Unlike guide opening (422) described above, guide opening (630) of the present example is open along the bottom of guide opening (622).

Figure 14:
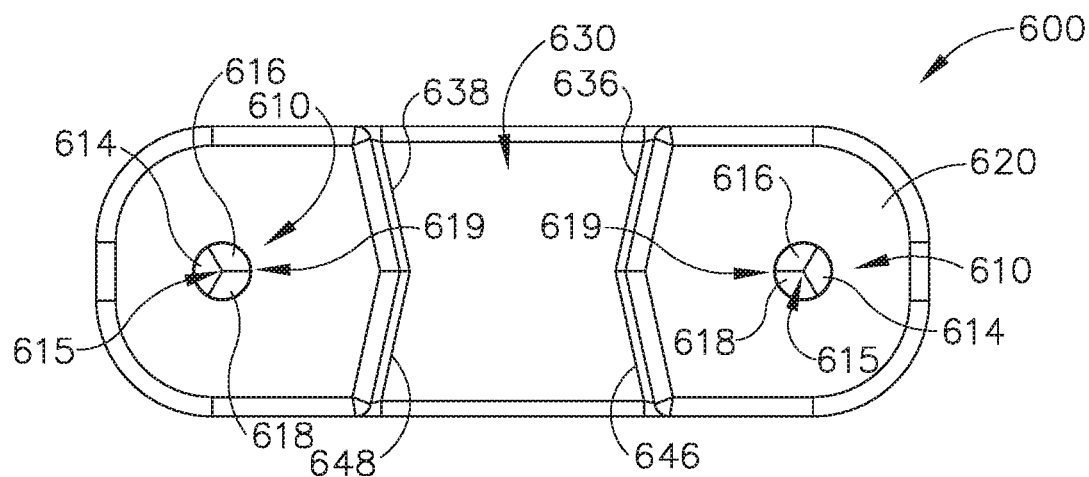
FIG. 14 depicts a bottom plan view of the guide tack of FIG. 9.

As best seen in FIG. 14, guide opening (630) of the present example is formed by several flat surfaces (632, 634, 636, 638, 642, 644, 646, 648). Surfaces (632, 634, 636, 638, 642, 644, 646, 648) are all oriented obliquely relative to the plane defined between legs (610); and relative to planes that are perpendicular to the plane defined between legs (610). When viewed along the direction shown in FIG. 13, surfaces (632, 634, 636, 638, 642, 644, 646, 648) are configured such that guide opening (630) deflects outwardly from the centerline of guide tack (600), at the mid-region of guide opening (630) along the height of guide opening (630), along the plane defined between legs (610). This configuration may promote capture of cannula (50) within guide opening (630), ensuring that cannula (50) remains at an appropriate distance from the surface (305) of the sclera (304).

When viewed along the direction shown in FIG. 14, surfaces (632, 634, 636, 638, 642, 644, 646, 648) are configured such that guide opening (630) deflects inwardly toward the centerline of guide tack (600), at the mid-region of guide opening (630) along the height of guide opening (630), along a plane that is perpendicular to the plane defined between legs (610). This configuration may minimize the amount of contact between cannula (50) and head (620), which may in turn minimize the amount of friction between cannula (50) and head (620) as cannula (50) is slid through guide opening (630). Reducing friction may reduce the risk of cannula (50) inadvertently pulling guide tack (600) from the eye (301) as cannula (50) is slid through guide opening (630). Despite this minimization of contact between cannula (50) and head (620), surfaces (632, 634, 636, 638, 642, 644, 646, 648) may still provide sufficient contact to maintain stability of cannula (50) when cannula (50) is disposed in guide opening (630).

Figure 15:
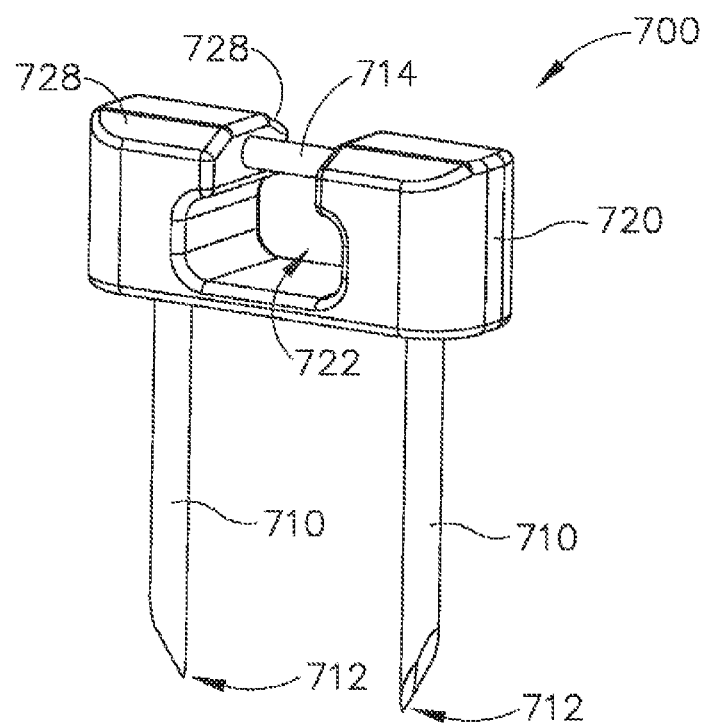
FIG. 15 depicts a perspective view of another exemplary alternative guide tack that may be used to guide the cannula of FIG. 2 during performance of the procedure shown in FIGS. 4A-4G, 5A-5C, and 8A-8E.
Figure 16:
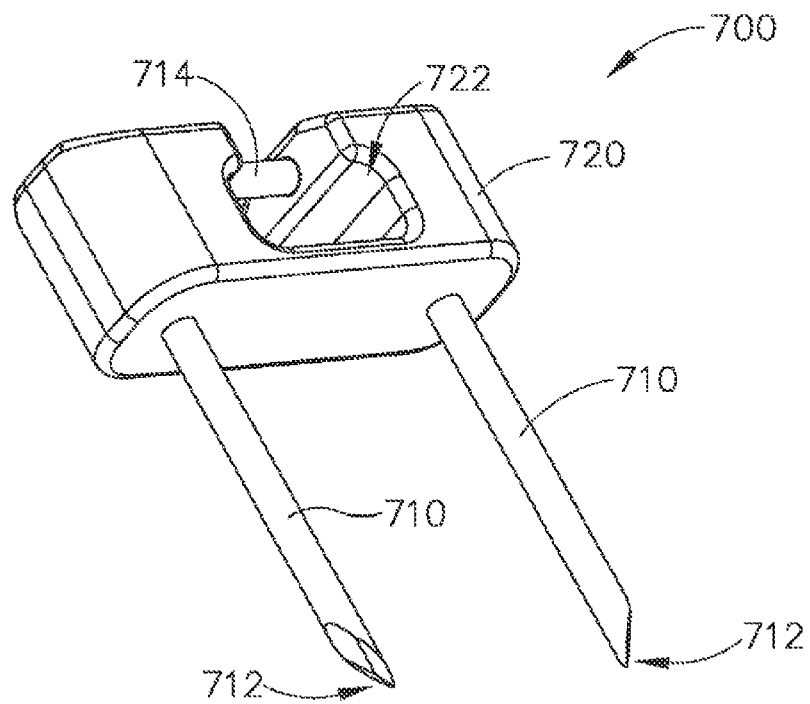
FIG. 16 depicts another perspective view of the guide tack of FIG. 15.
Figure 17:
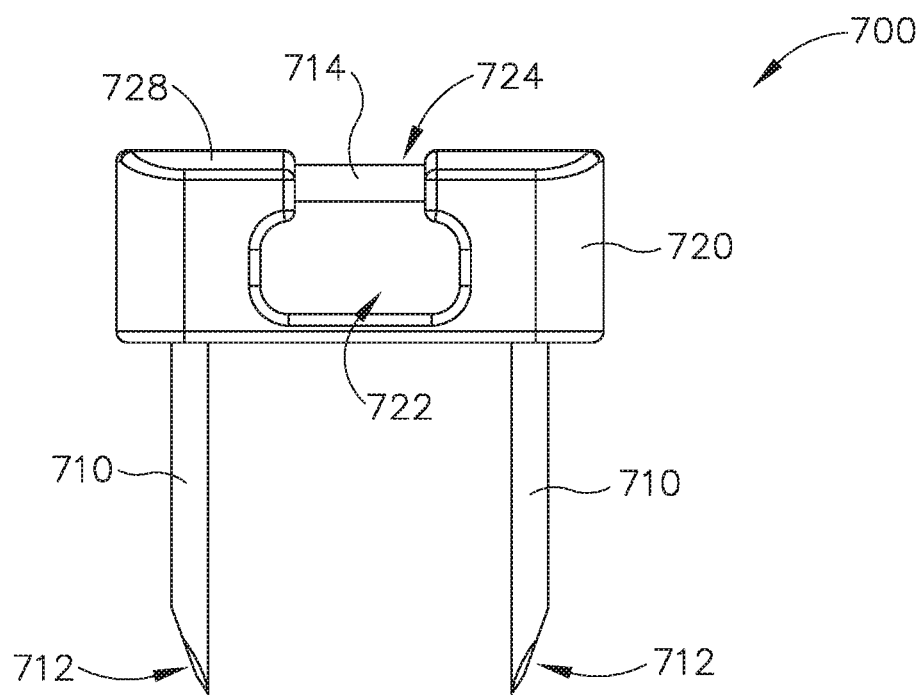
FIG. 17 depicts a front elevational view of the guide tack of FIG. 15.

FIGS. 15-17 show another exemplary guide tack (700) that may be used in place of guide tack (400) described above. Except as otherwise described below, guide tack (700) of this example may be configured and operable just like guide tack (400). Guide tack (700) of this example includes a head (720) with a pair of legs (710) extending downwardly from head (720). The free end of each leg (710) includes a sharp tip (712). Sharp tips (712) may be formed just like sharp tips (612). Alternatively, sharp tips (712) may have any other suitable configuration.

Head (720) of the present example defines a guide opening (722) and a pair of chamfers (728). Guide opening (722) is sized and configured to slidably receive cannula (50). Guide opening (722) is oriented along an axis that is transverse to the plane defined between legs (710). Unlike guide opening (422) described above, guide opening (722) of the present example is open along the top of guide opening (722). However, a crown portion (714) of legs (710) extends through the open top of guide opening (722), effectively closing the top of guide opening (722). In some versions, both legs (710) and crown portion (714) are formed of a single monolithic piece of material. In some other versions, legs (710) and crown portion (714) are formed separately and are simply molded together with head (720). Other suitable configurations and arrangements will be apparent to those of ordinary skill in the art in view of the teachings herein.

Figure 18:
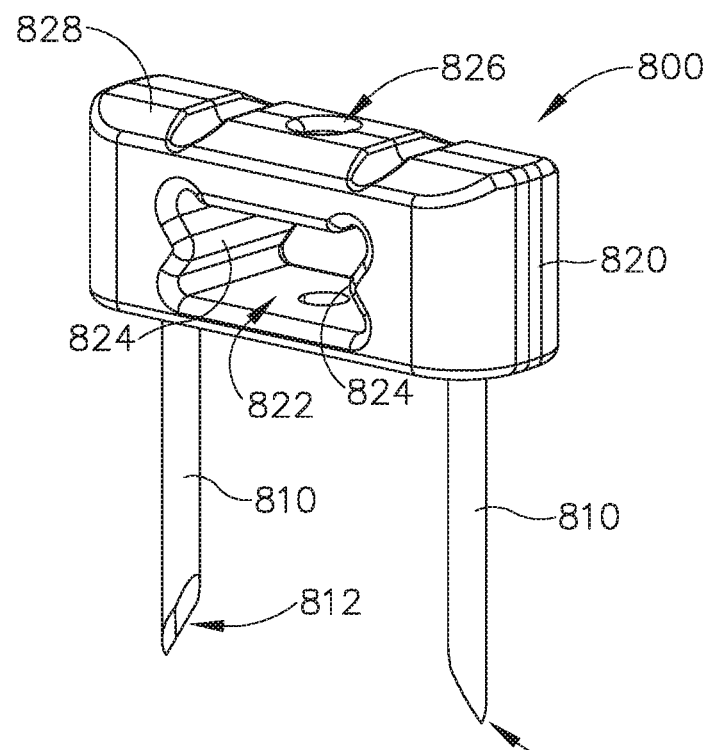
FIG. 18 depicts a perspective view of another exemplary alternative guide tack that may be used to guide the cannula of FIG. 2 during performance of the procedure shown in FIGS. 4A-4G, 5A-5C, and 8A-8E.
Figure 19:
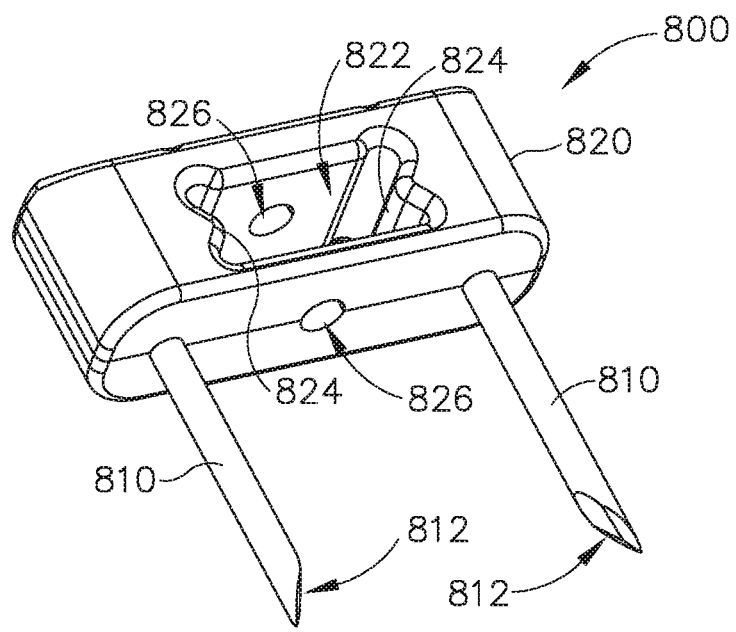
FIG. 19 depicts another perspective view of the guide tack of FIG. 18.
Figure 20:
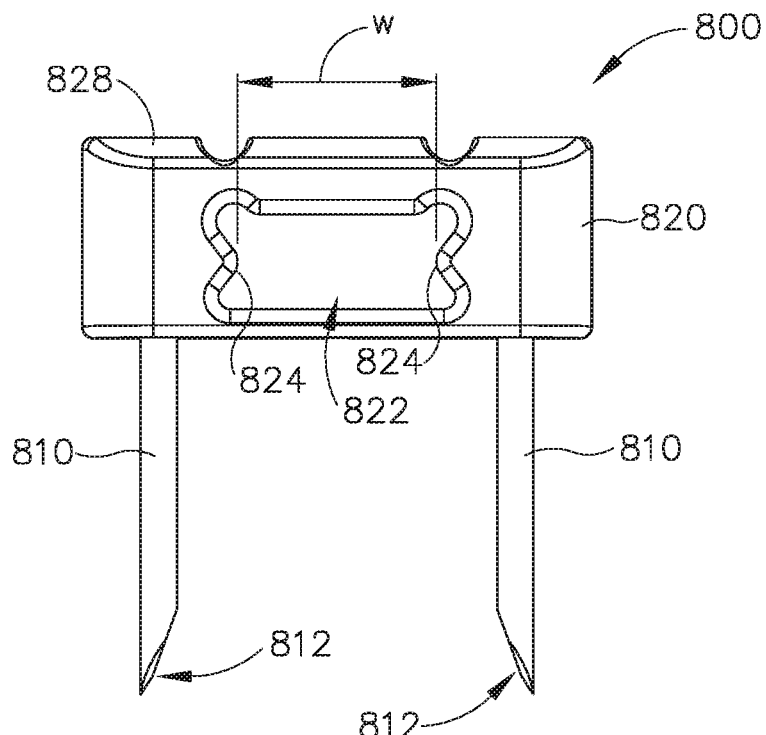
FIG. 20 depicts a front elevational view of the guide tack of FIG. 18.

FIGS. 18-20 show another exemplary guide tack (800) that may be used in place of guide tack (400) described above. Except as otherwise described below, guide tack (800) of this example may be configured and operable just like guide tack (400). Guide tack (800) of this example includes a head (820) with a pair of legs (810) extending downwardly from head (820). The free end of each leg (810) includes a sharp tip (812). Sharp tips (812) may be formed just like sharp tips (612). Alternatively, sharp tips (812) may have any other suitable configuration.

Head (820) of the present example defines a guide opening (822), retainer pin openings (826), and a pair of chamfers (828). Guide opening (822) is sized and configured to slidably receive cannula (50). Guide opening (822) is oriented along an axis that is transverse to the plane defined between legs (810). Retainer pin openings (826) are oriented along an axis that is parallel to the longitudinal axes of legs (810). Retainer pin openings (826) are dimensioned to receive a retainer pin of a deployment instrument, as will also be described in greater detail below.

Head (820) of the present example further includes a pair of ribs (824) extending along the full length of guide opening (822), at the lateral sides of guide opening (822). Ribs (824) together define an effective width (w) of opening (822). This width (w) is sized to closely correspond with the width of catheter (50), such that ribs (824) slidingly contact catheter (50) as catheter (50) is slid through opening (822). This configuration may minimize the amount of contact between cannula (50) and head (820), which may in turn minimize the amount of friction between cannula (50) and head (820) as cannula (50) is slid through guide opening (822). Reducing friction may reduce the risk of cannula (50) inadvertently pulling guide tack (800) from the eye (301) as cannula (50) is slid through guide opening (822). Despite this minimization of contact between cannula (50) and head (820), ribs (824) may still provide sufficient contact to maintain stability of cannula (50) when cannula (50) is disposed in guide opening (822).

Figure 21:
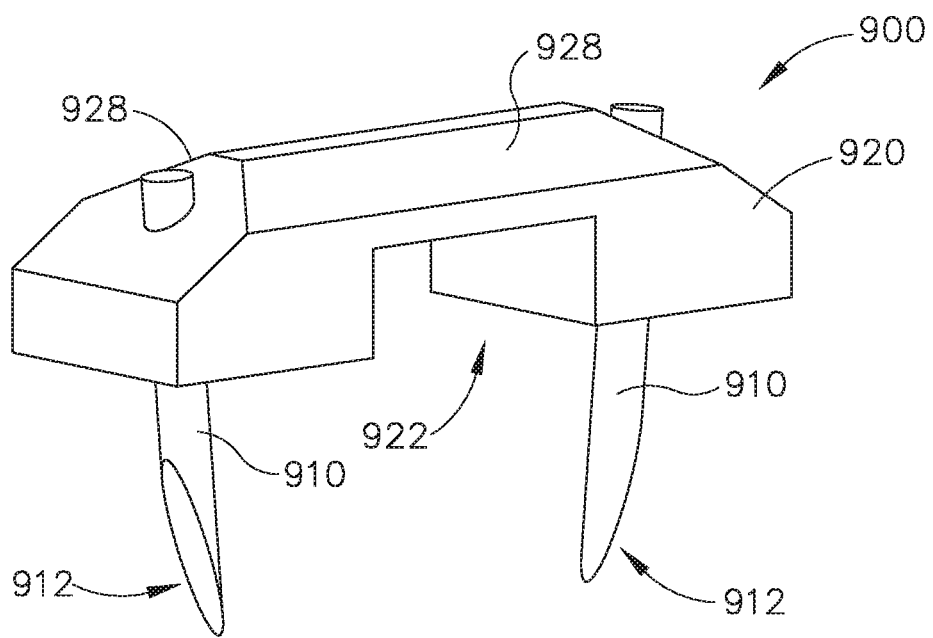
FIG. 21 depicts a perspective view of another exemplary alternative guide tack that may be used to guide the cannula of FIG. 2 during performance of the procedure shown in FIGS. 4A-4G, 5A-5C, and 8A-8E.
Figure 22:
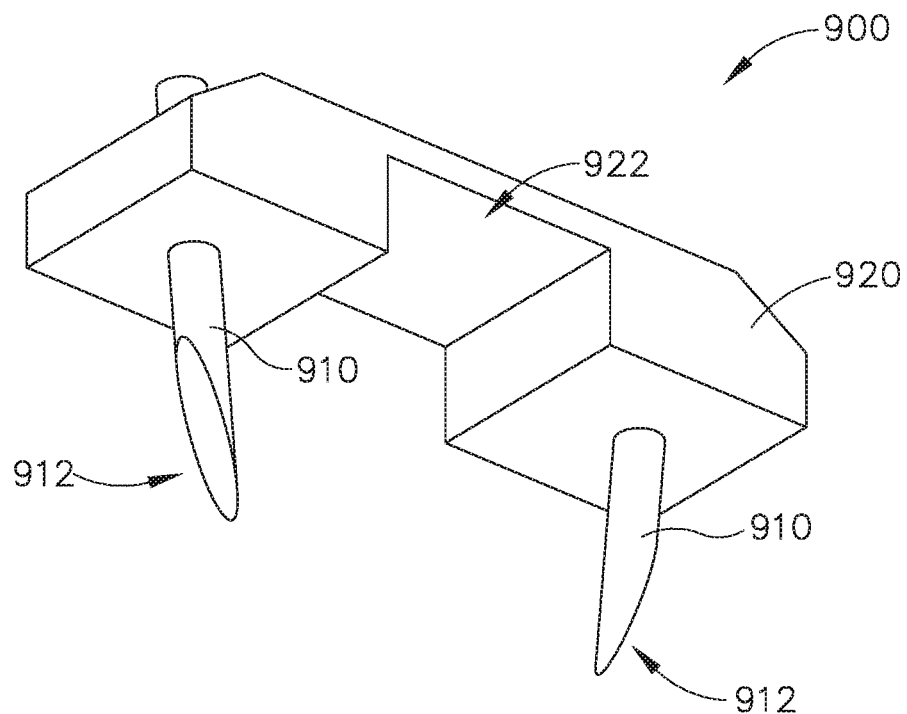
FIG. 22 depicts another perspective view of the guide tack of FIG. 21.

FIGS. 21-22 show another exemplary guide tack (900) that may be used in place of guide tack (400) described above. Except as otherwise described below, guide tack (900) of this example may be configured and operable just like guide tack (400). Guide tack (900) of this example includes a head (920) with a pair of legs (910) extending downwardly from head (920). The free end of each leg (910) includes a sharp tip (912). Sharp tips (912) may be formed just like sharp tips (612). Alternatively, sharp tips (912) may have any other suitable configuration.

Head (820) of the present example defines a guide notch (922) and a pair of chamfers (928). Guide notch (922) is oriented along an axis that is transverse to the plane defined between legs (910). When guide tack (900) is secured to the eye (301), guide notch (922) is configured to cooperate with the surface (305) of the sclera (304) to define a guide opening. The guide opening defined by surface (305) and guide notch (922) is sized and configured to slidably receive cannula (50).

Figure 23:
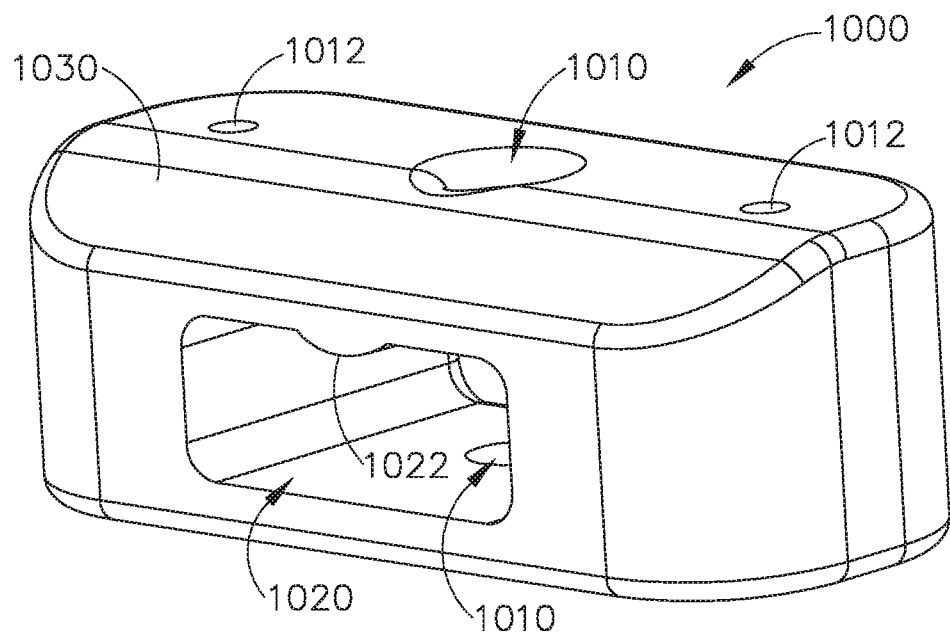
FIG. 23 depicts a perspective view of an exemplary alternative head that may be incorporated into any of the guide tacks described herein.
Figure 24:
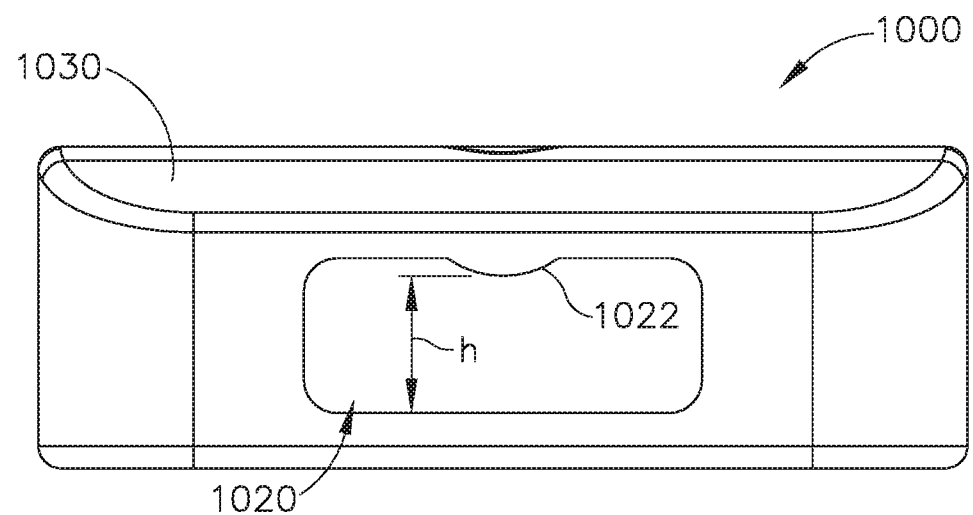
FIG. 24 depicts a front elevational view of the head of FIG. 23.
Figure 25:
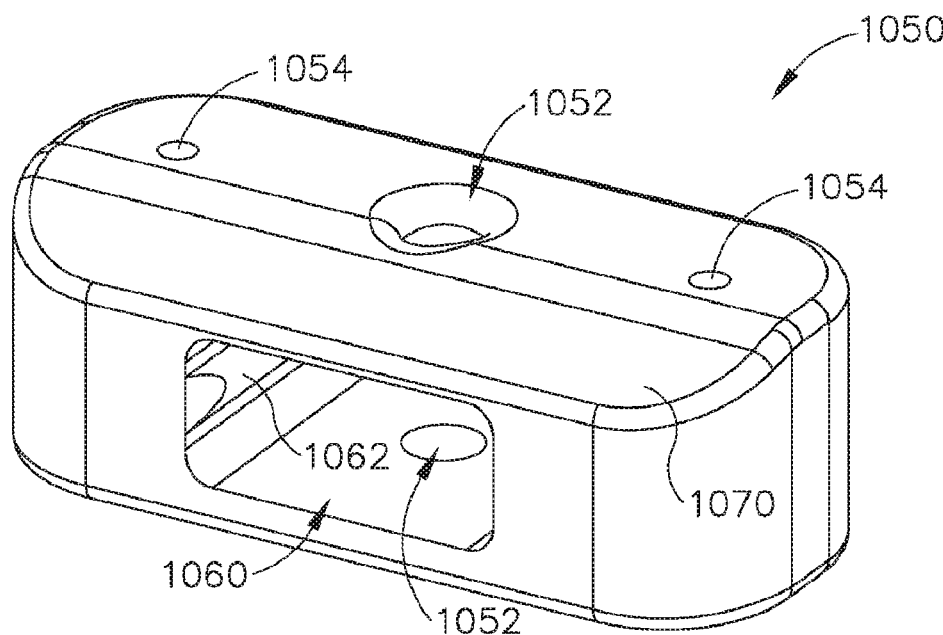
FIG. 25 depicts a perspective view of another exemplary alternative head that may be incorporated into any of the guide tacks described herein.
Figure 26:
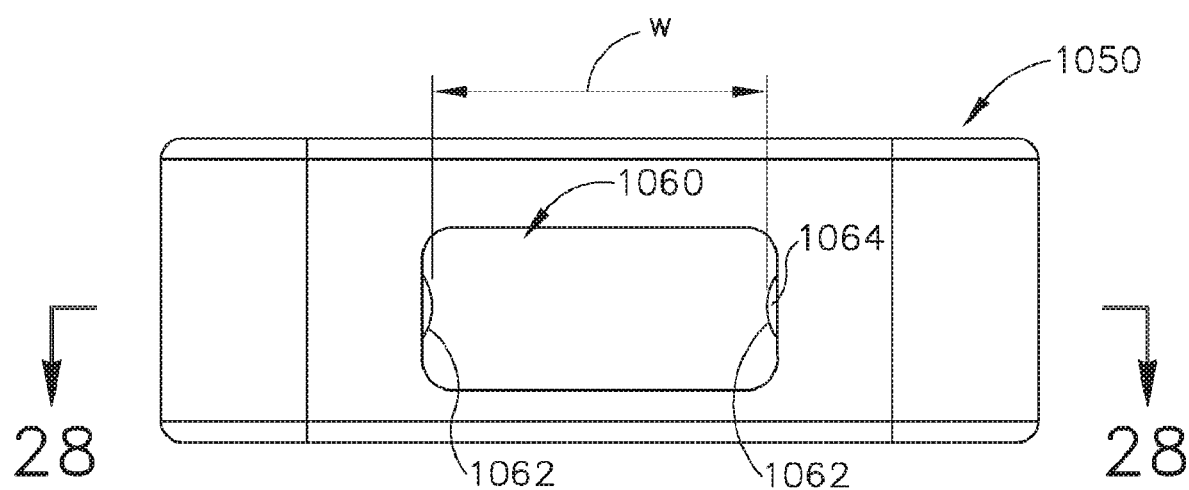
FIG. 26 depicts a front elevational view of the head of FIG. 25.
Figure 27:
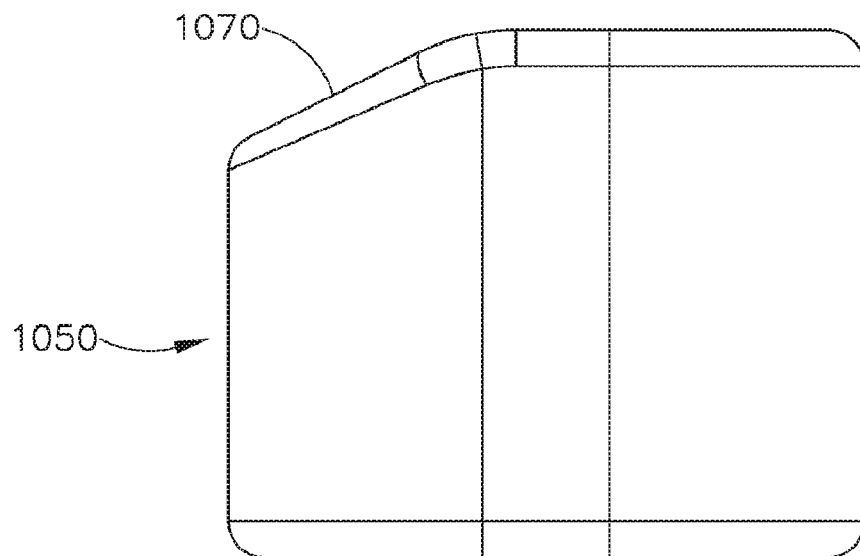
FIG. 27 depicts a side elevational view of the head of FIG. 25.
Figure 28:
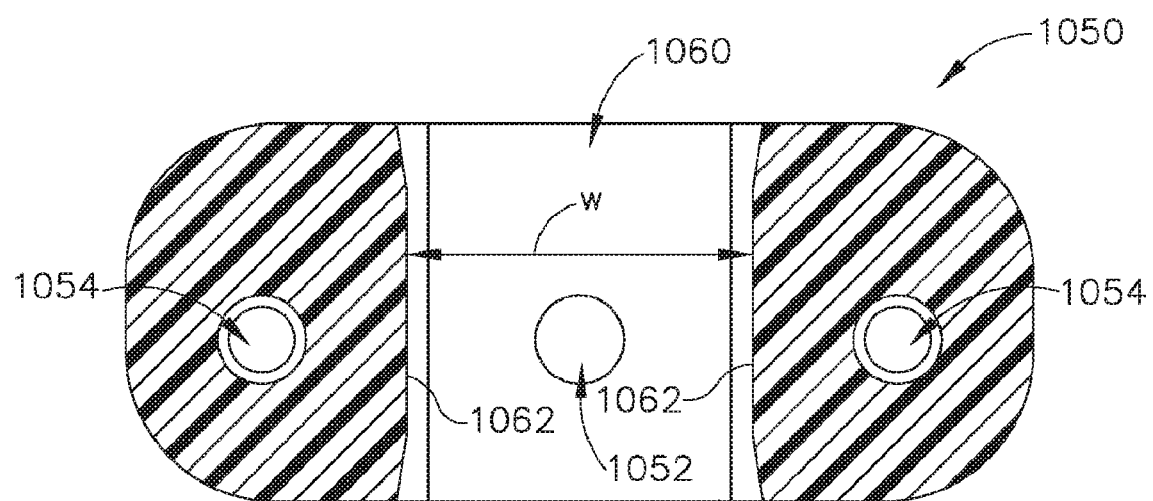
FIG. 28 depicts a cross-sectional view of the head of FIG. 25, taken along line 28-28 of FIG. 26.

FIGS. 23-24 show an exemplary alternative head (1000) that may be readily incorporated into any of the guide tacks (400) described herein. Head (1000) of this example includes retainer pin openings (1010), a pair of leg openings (1012), a guide opening (1020), and a chamfer (1030). Retainer pin openings (1010) are oriented along an axis that is parallel to the longitudinal axes of legs that are disposed in leg openings (1012). Retainer pin openings (1010) are dimensioned to receive a retainer pin of a deployment instrument, as will also be described in greater detail below. Leg openings (1012) are configured to receive respective legs, which may be configured like any of the various guide tack legs described herein. Leg openings (1012) extend to the top surface of head (1000), such that the upper ends of legs disposed in leg openings (1012) may be exposed relative to head (1000).

Guide opening (1020) is sized and configured to slidably receive cannula (50). Guide opening (1020) is oriented along an axis that is transverse to the plane defined between legs that are disposed in leg openings (1012). Head (1000) of the present example further includes a rib (1022) extending along the full length of guide opening (1020), at the upper side of guide opening (1020). Rib (1022) and the bottom surface of guide opening (1020) together define an effective height (h) of opening (1020). This height (h) is sized to closely correspond with the thickness of catheter (50), such that rib (1022) and the bottom surface of guide opening (1020) slidingly contact catheter (50) as catheter (50) is slid through opening (1020). This configuration may reduce the amount of contact between cannula (50) and head (1000), which may in turn reduce the amount of friction between cannula (50) and head (1000) as cannula (50) is slid through guide opening (1020). Reducing friction may reduce the risk of cannula (50) inadvertently pulling a guide tack incorporating head (1000) from the eye (301) as cannula (50) is slid through guide opening (1020). Despite this reduction of contact between cannula (50) and head (1050), rib (1022) and the bottom surface of guide opening (1020) may still provide sufficient contact to maintain stability of cannula (50) when cannula (50) is disposed in guide opening (1020).

FIGS. 25-28 show another exemplary alternative head (1050) that may be readily incorporated into any of the guide tacks (400) described herein. Head (1050) of this example includes retainer pin openings (1052), a pair of leg openings (1054), a guide opening (1060), and a chamfer (1070). Retainer pin openings (1052) are oriented along an axis that is parallel to the longitudinal axes of legs that are disposed in leg openings (1054). Retainer pin openings (1052) are dimensioned to receive a retainer pin of a deployment instrument, as will also be described in greater detail below. Leg openings (1054) are configured to receive respective legs, which may be configured like any of the various guide tack legs described herein. Leg openings (1054) extend to the top surface of head (1050), such that the upper ends of legs disposed in leg openings (1054) may be exposed relative to head (1050).

Guide opening (1060) is sized and configured to slidably receive cannula (50). Guide opening (1060) is oriented along an axis that is transverse to the plane defined between legs that are disposed in leg openings (1054). Head (1050) of the present example further includes a pair of ribs (1062) extending along the full length of guide opening (1060), at the lateral sides of guide opening (1060). Ribs (1062) together define an effective width (w) of opening (1060). This width (w) is sized to closely correspond with the width of catheter (50), such that ribs (1062) slidingly contact catheter (50) as catheter (50) is slid through opening (1062). This configuration may minimize the amount of contact between cannula (50) and head (1050), which may in turn minimize the amount of friction between cannula (50) and head (1050) as cannula (50) is slid through guide opening (1060). Reducing friction may reduce the risk of cannula (50) inadvertently pulling a guide tack incorporating head (1050) from the eye (301) as cannula (50) is slid through guide opening (1060). Despite this minimization of contact between cannula (50) and head (1050), ribs (1062) may still provide sufficient contact to maintain stability of cannula (50) when cannula (50) is disposed in guide opening (1060).

Figure 29:
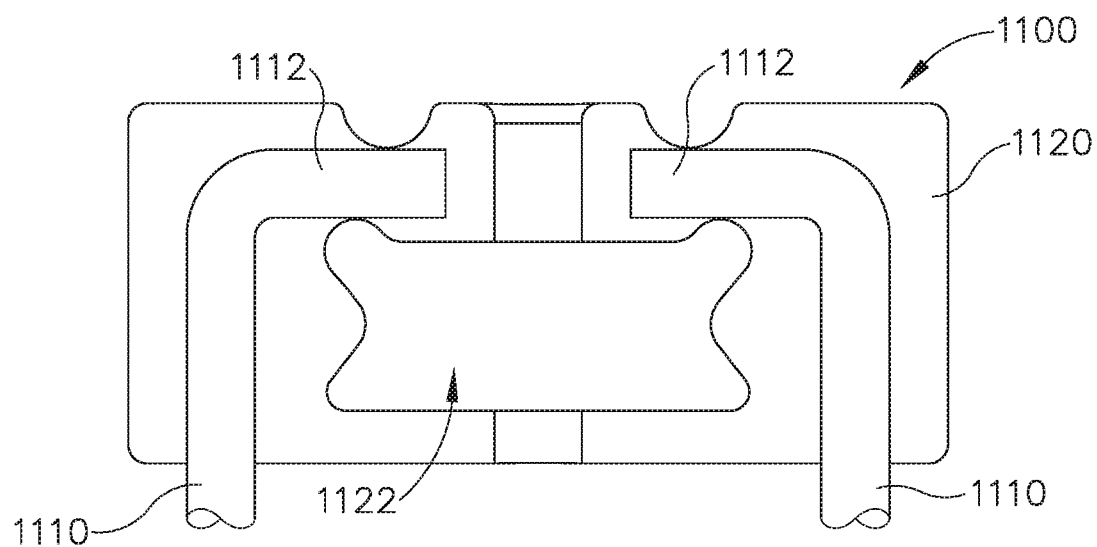
FIG. 29 depicts a partial cross-sectional view of an upper portion of another exemplary alternative guide tack that may be used to guide the cannula of FIG. 2 during performance of the procedure shown in FIGS. 4A-4G, 5A-5C, and 8A-8E.
Figure 30:
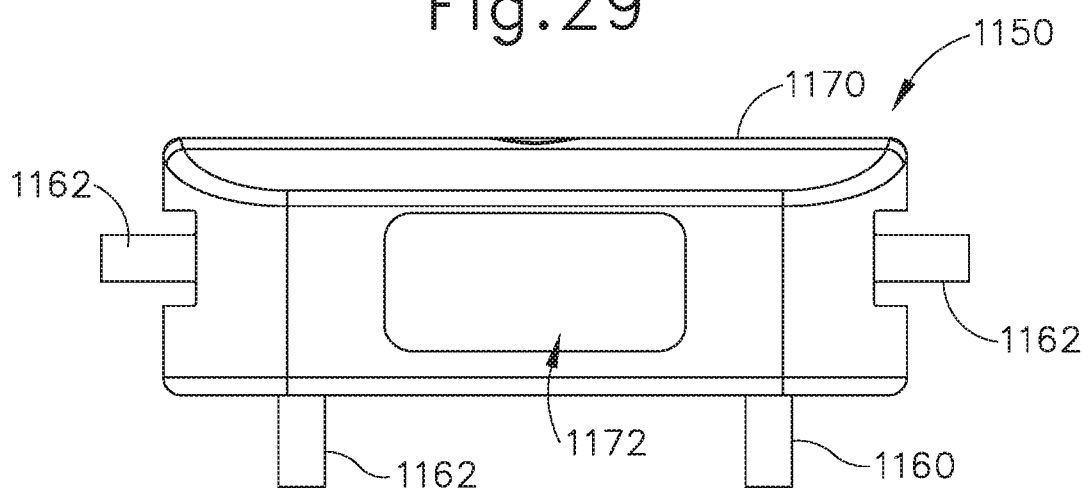
FIG. 30 depicts a partial front elevational view of an upper portion of another exemplary alternative guide tack that may be used to guide the cannula of FIG. 2 during performance of the procedure shown in FIGS. 4A-4G, 5A-5C, and 8A-8E.
Figure 31:
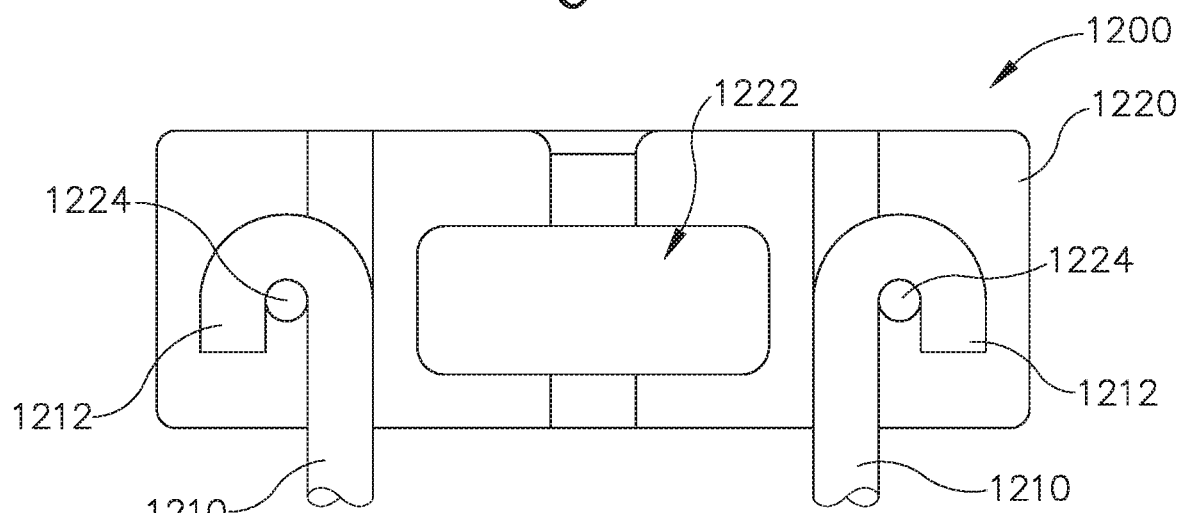
FIG. 31 depicts a partial cross-sectional view of an upper portion of another exemplary alternative guide tack that may be used to guide the cannula of FIG. 2 during performance of the procedure shown in FIGS. 4A-4G, 5A-5C, and 8A-8E.

FIGS. 29-31 show additional exemplary configurations that may be used to secure the legs of a guide tack to the head of a guide tack. In particular, FIG. 29 shows a guide tack (1100) where upper ends (1112) of legs (1110) are bent inwardly toward each other, above a guide opening (1122) in head (1120). Head (1120) may be overmolded about bent upper ends (1112) of legs (1110) to secure legs (1110) to head (1120). FIG. 30 shows a guide tack (1150) where upper ends (1162) of legs (1160) are bent outwardly away from each other, near a guide opening (1172). Head (1170) may be overmolded about bent upper ends (1162) of legs (1160) to secure legs (1160) to head (1170). FIG. 31 shows a guide tack (1200) where upper ends (1212) of legs (1210) are bent around pins (1224) in head (1220), near a guide opening (1222). In this example, pins (1224) are oriented perpendicularly relative to the straight portions of legs (1160). Head (1220) may be overmolded about pins (1224) and bent upper ends (1212) of legs (1212) to secure legs (1160) to head (1170).

It should be understood that any of the relationships between the legs (1110, 1162, 1210) and respective heads (1120, 1170, 1220) of guide tacks (1100, 1150, 1200) shown in FIGS. 29-31 may be readily incorporated into any of the various guide tacks described herein. Other suitable relationships that may be provided between the legs and heads of guide tacks will be apparent to those of ordinary skill in the art in view of the teachings herein.

Figure 32:
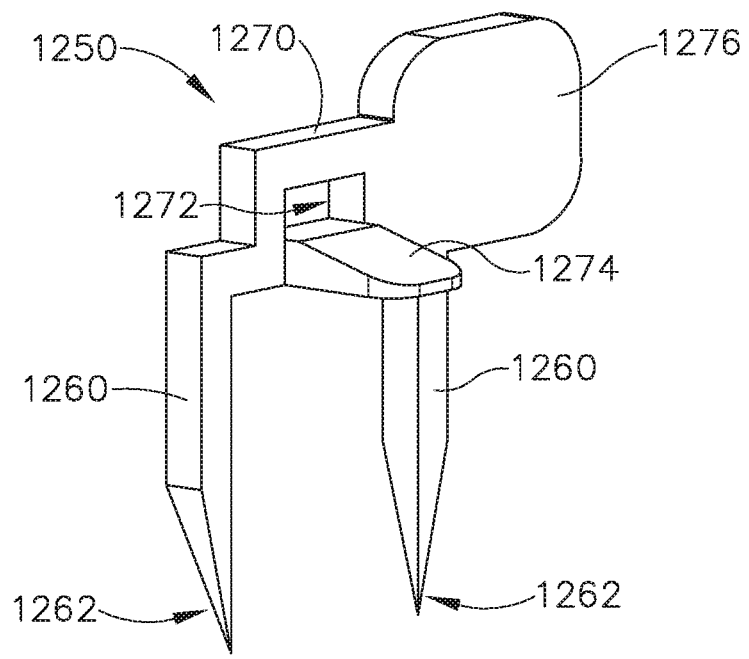
FIG. 32 depicts a perspective view of another exemplary alternative guide tack that may be used to guide the cannula of FIG. 2 during performance of the procedure shown in FIGS. 4A-4G, 5A-5C, and 8A-8E.
Figure 33:
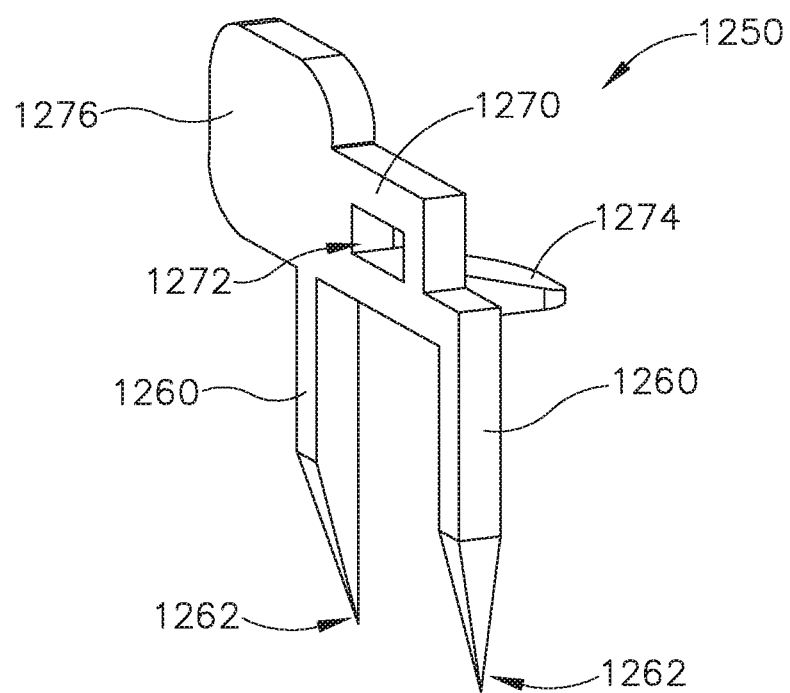
FIG. 33 depicts another perspective view of the guide tack of FIG. 32.

FIGS. 32-33 show another exemplary guide tack (1250) that may be used in place of guide tack (400) described above. Except as otherwise described below, guide tack (1250) of this example may be configured and operable just like guide tack (400). Guide tack (1250) of this example includes a pair of legs (1260) with sharp tips (1262), a head portion (1270) defining a guide opening (1274), a guide ramp (1274), and a grasping tab (1276). Guide opening (1272) is sized and configured to slidably receive cannula (50). Guide opening (1272) is oriented along an axis that is transverse to the plane defined between legs (1260). Guide ramp (1274) is configured to stabilize guide tack (1250) against the surface (305) of the sclera (304) and assist in guiding cannula (50) into guide opening (1272). Grasping tab (1276) is configured to facilitate grasping and manipulation of guide tack (1250) with any suitable grasping instrument. In some versions, guide tack (1250) is formed of milled steel. Alternatively, any other suitable materials and processes may be used to form guide tack (1250).

Figure 34:
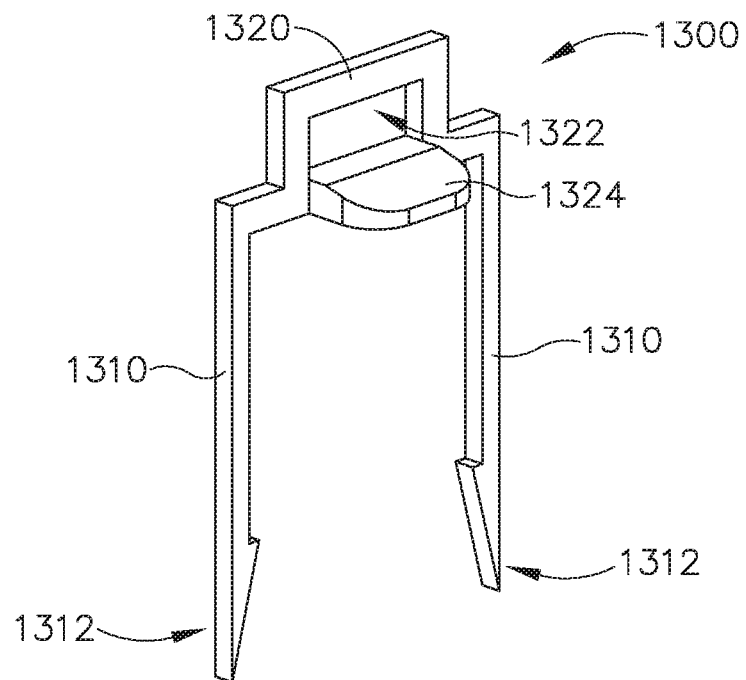
FIG. 34 depicts a perspective view of another exemplary alternative guide tack that may be used to guide the cannula of FIG. 2 during performance of the procedure shown in FIGS. 4A-4G, 5A-5C, and 8A-8E.
Figure 35:
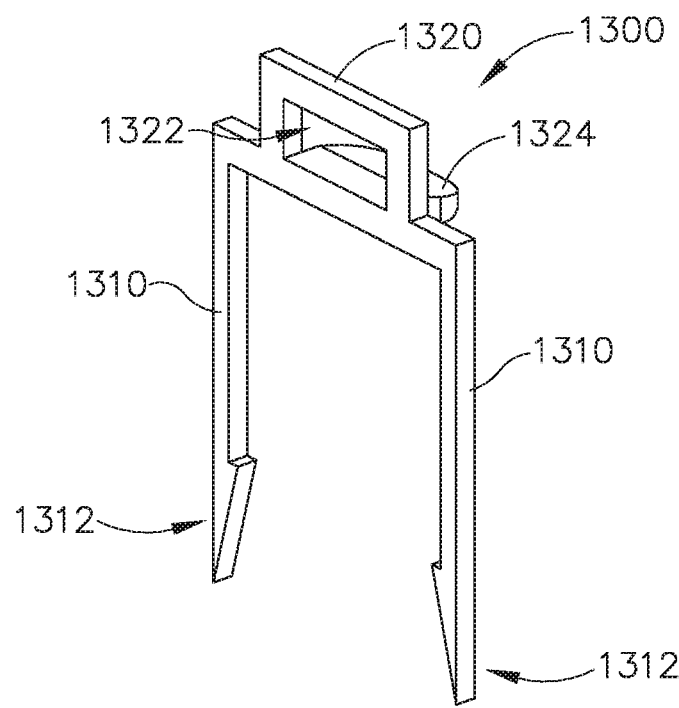
FIG. 35 depicts another perspective view of the guide tack of FIG. 34.

FIGS. 34-35 show another exemplary guide tack (1300) that may be used in place of guide tack (400) described above. Except as otherwise described below, guide tack (1300) of this example may be configured and operable just like guide tack (400). Guide tack (1300) of this example includes a pair of legs (1310) with sharp tips (1312), a head portion (1320) defining a guide opening (1322), and a guide ramp (1324). Sharp tips (1312) are barbed in the present example, though this is merely optional. Guide opening (1322) is sized and configured to slidably receive cannula (50). Guide opening (1322) is oriented along an axis that is transverse to the plane defined between legs (1310). Guide ramp (1324) is configured to stabilize guide tack (1300) against the surface (305) of the sclera (304) and assist in guiding cannula (50) into guide opening (1322). In some versions, guide tack (1300) is formed of milled steel. Alternatively, any other suitable materials and processes may be used to form guide tack (1300).

IV. Exemplary Marking and Deployment Instruments

As noted above, a marking and deployment instrument (500) may be used to provide the following three functions: mark the site where a guide tack (400) is to be installed in the eye (301), install the guide tack (400) at the marked site, and mark the site where a sclerotomy (514) is to be formed. The examples described below provide several forms that such an instrument (500) may take. While the examples provided below provide all three functions through a single instrument, the examples may be readily modified to separate the functions among two instruments. For instance, a first instrument may be used to mark the site where a guide tack (400) is to be installed in the eye (301), while a second instrument may be used to install the guide tack (400) at the marked site and mark the site where a sclerotomy (514) is to be formed. Other variations will be apparent to those of ordinary skill in the art in view of the teachings herein. To the extent that examples described below refer specifically to guide tack (400), the exemplary instruments described below (and variations thereof) may alternatively be used with any of the various guide tacks described herein.

Figure 36:
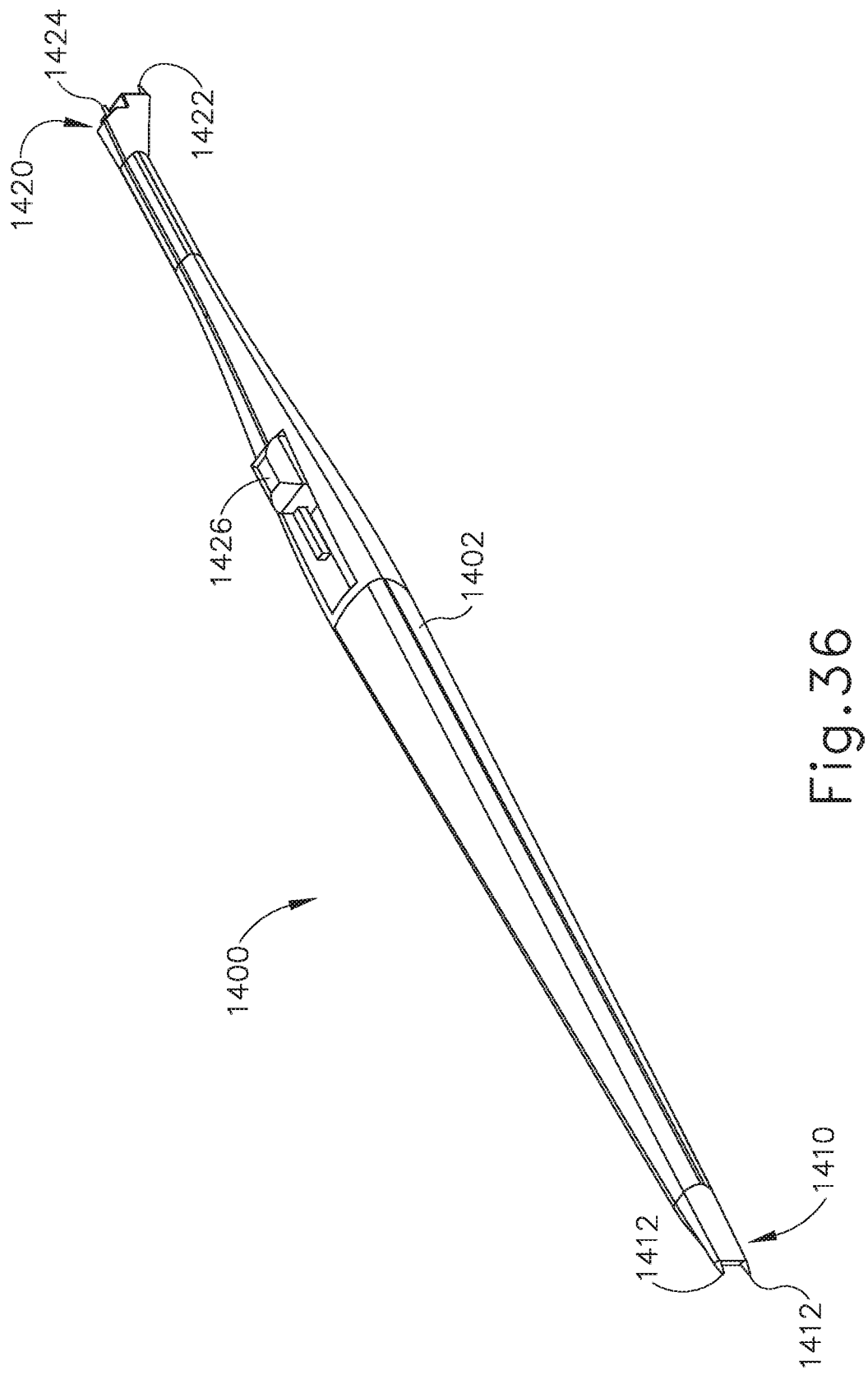
FIG. 36 depicts a perspective view of an exemplary marking and deployment instrument that may be used during performance of the procedure shown in FIGS. 8A-8E.
Figure 37:
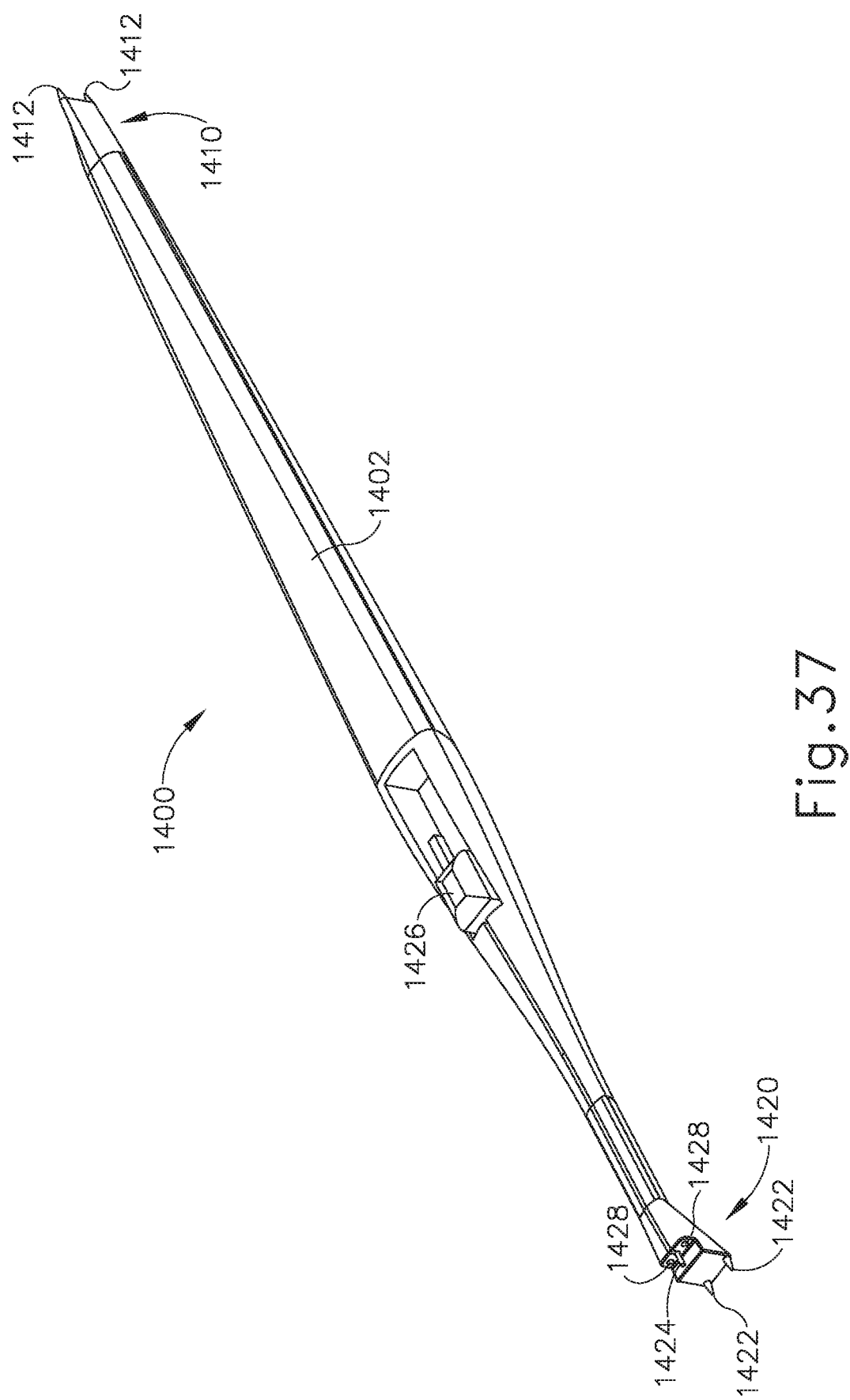
FIG. 37 depicts another perspective view of the marking and deployment instrument of FIG. 36.
Figure 38:
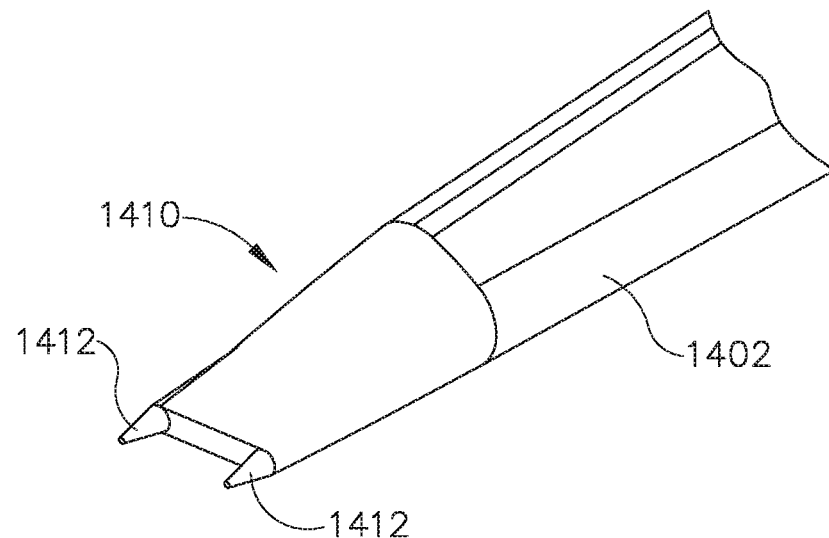
FIG. 38 depicts a partial perspective view of a first end of the marking and deployment instrument of FIG. 36.

FIGS. 36-41B show an exemplary marking and deployment instrument (1400). Instrument (1400) of this example includes a shaft (1402) having a first end (1410) and a second end (1420). Shaft (1402) is sized and configured to be easily grasped and manipulated by an operator's hand (e.g., using a pencil grip), without requiring additional tools to grasp or manipulate instrument (1400). As best seen in FIGS. 36 and 38, first end (1410) of shaft (1402) includes a pair of prongs (1412). While prongs (1412) are pointed in the present example, prongs (1412) are configured to be atraumatic such that prongs (1412) will not pierce the sclera (304) when prongs (1412) are urged against the surface (305) of the sclera (304) to mark the surface (305) as described herein.

In some versions, prongs (1412) are positioned such that the spacing between prongs (1412) corresponds with the spacing between the limbus of the eye (301) and the pars plana of the eye (301). In such versions, as noted above, since the guide tack (400) is to be deployed at the pars plana region, the operator may use first end (1410) to determine the location of the appropriate region to deploy guide tack (400). In addition, or in the alternative, prongs (1412) may be positioned such that the spacing between prongs (1412) corresponds with the spacing between legs (410) of guide tack (400). Thus, prongs (1412) may be used to mark the insertion points for legs (410). In particular, the operator may first press prongs (1412) against an inkpad, and then press prongs (1412) against surface (305) of sclera (304) to leave markings (510) as described above with reference to FIG. 8A.

Figure 39:
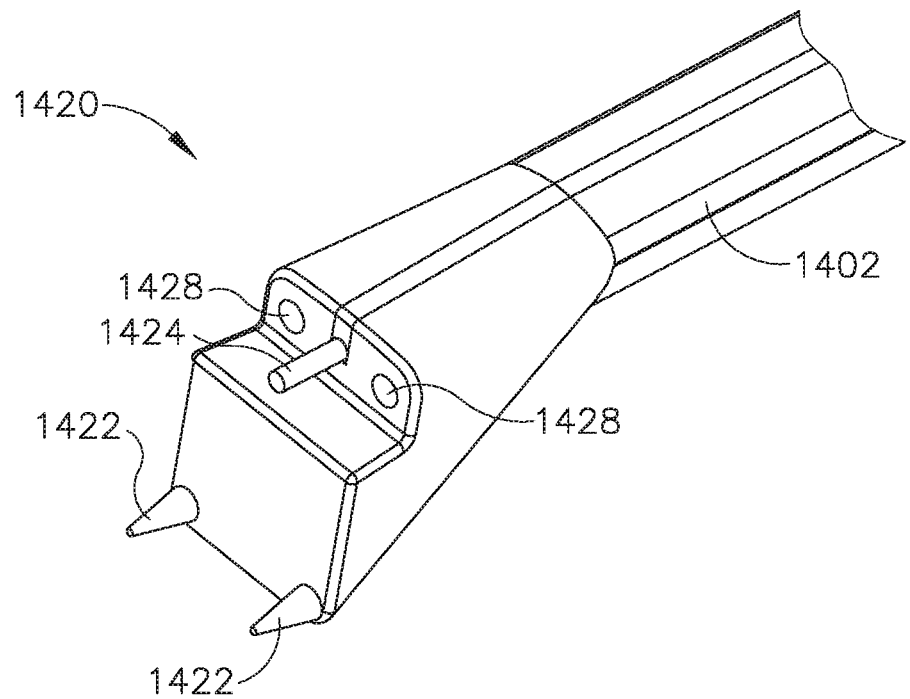
FIG. 39 depicts a partial perspective view of a second end of the marking and deployment instrument of FIG. 36.

As best seen in FIGS. 37 and 39, second end (1420) includes a pair of prongs (1422), a retention pin (1424), and a pair of magnets (1428). While prongs (1422) are pointed in the present example, prongs (1422) are configured to be atraumatic such that prongs (1422) will not pierce the sclera (304) when prongs (1422) are urged against the surface (305) of the sclera (304) to mark the surface (305) as described herein. Prongs (1422) are positioned such that the spacing between prongs (1422) corresponds with an appropriate length of a sclerotomy (514) to receive cannula (50). For instance, prongs (1412) may be positioned such that prongs (1422) are spaced apart by approximately 3 mm, center to center. Thus, prongs (1422) may be used to mark the site of a sclerotomy (514). In particular, the operator may first press prongs (1422) against an inkpad, and then press prongs (1422) against surface (305) of sclera (304) to leave markings (512) as described above with reference to FIG. 8C.

Figure 40:
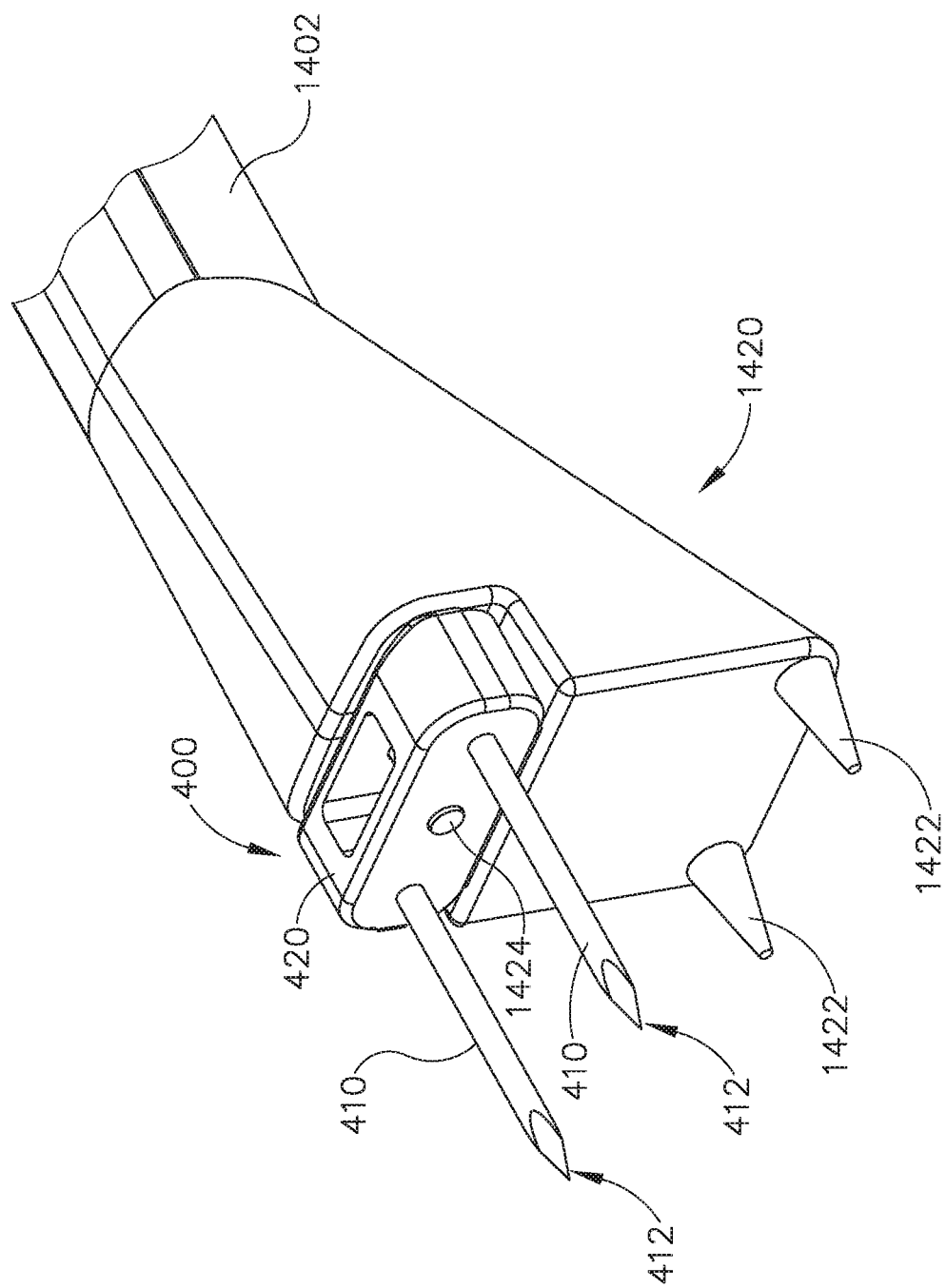
FIG. 40 depicts a partial perspective view of the second end of the marking and deployment instrument of FIG. 36, with the guide tack of FIG. 6 mounted thereon.

Retention pin (1424) is configured to fit in the retention pin openings of a guide tack. In particular, retention pin (1424) is configured to provide friction with the retention pin openings of a guide tack, such that the guide tack is removably secured to second end (1420) via frictional engagement with retention pin (1424). An example of such engagement is shown in FIG. 40, where retention pin (1424) is disposed in both retention pin openings (424). Magnets (1428) are positioned to correspond with the locations of exposed upper ends (426) of legs (410). Since legs (410) are formed of a ferrous material in this example, magnets (1428) thus further removably secure guide tack (400) to second end (1420). In variations where the upper ends of the legs of the guide tack are not exposed, magnets (1428) may still provide sufficient magnetic attraction to releasably retain the guide tack on second end (1420). It should also be understood that some variations of instrument (1400) may lack retention pin (1424) while still having magnets (1428); or lack magnets (1428) while still having retention pin (1424).

Figure 41A:
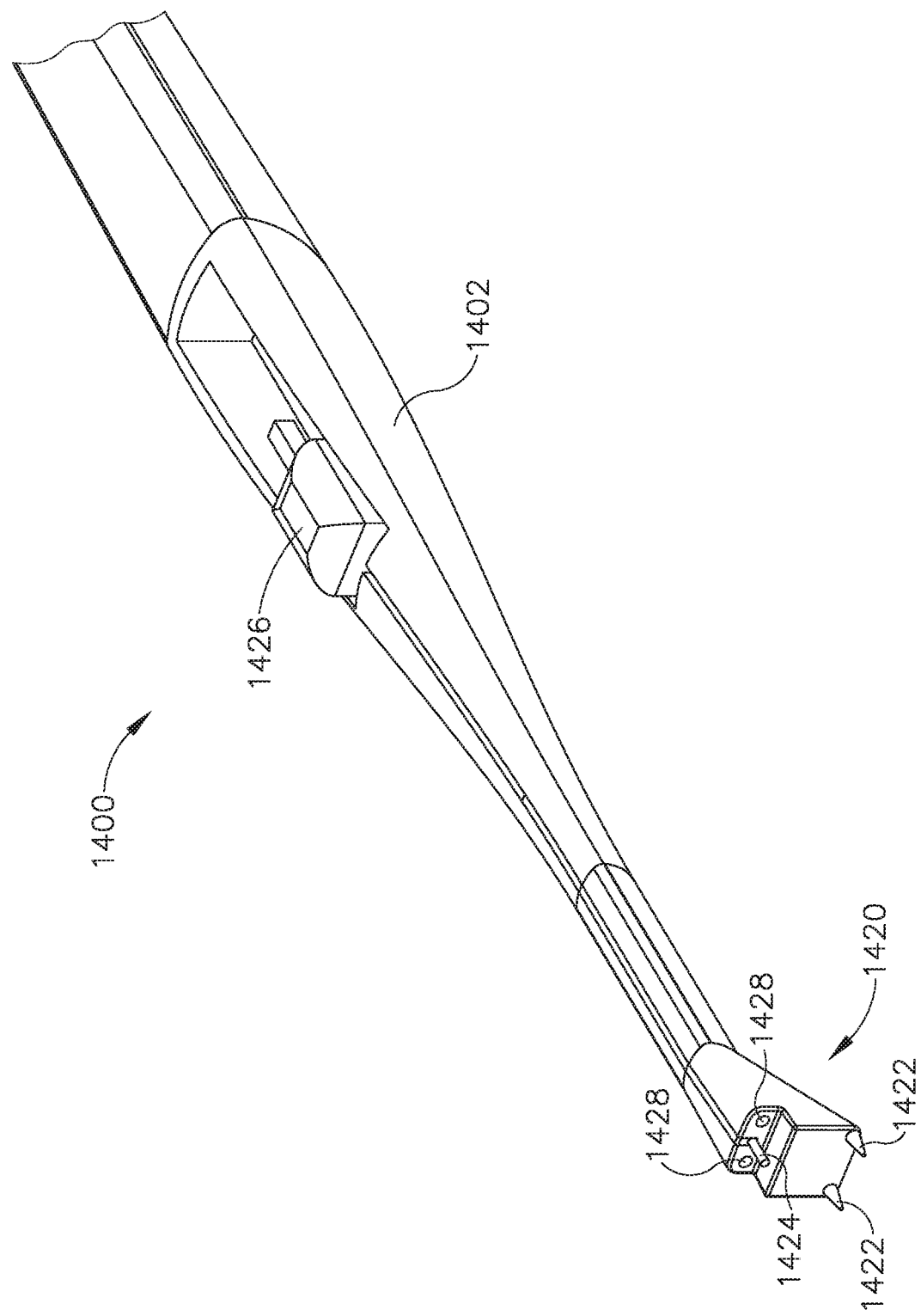
FIG. 41A depicts a partial perspective view of the second end of the marking and deployment instrument of FIG. 36, with a slider and attachment pin in a distal position.
Figure 41B:
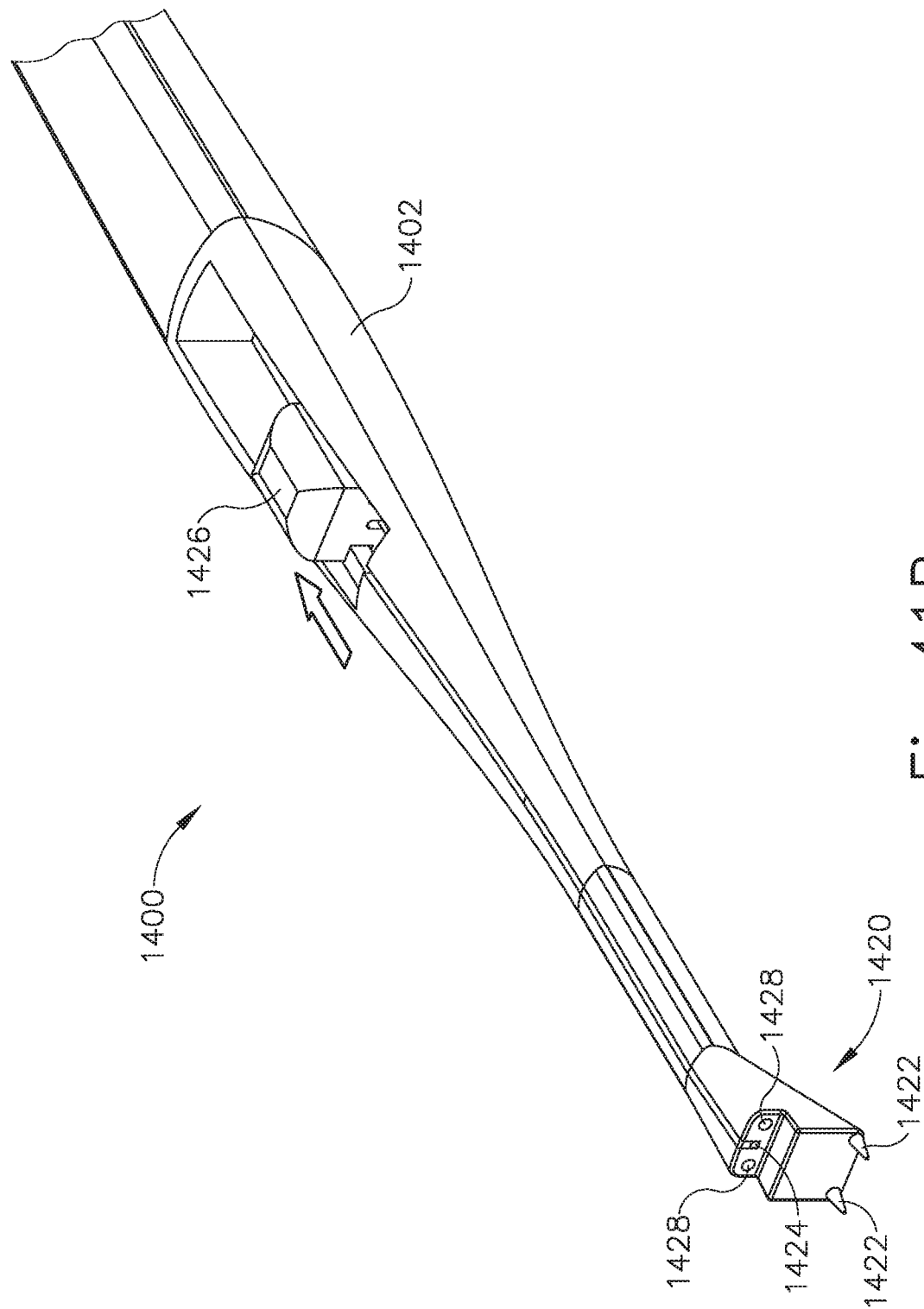
FIG. 41B depicts a partial perspective view of the second end of the marking and deployment instrument of FIG. 36, with the slider and attachment pin in a proximal position.

As shown in FIGS. 41A-41B, retention pin (1424) is secured to a slider (1426) in the present example. Slider (1426) is slidable relative to shaft (1402) between a distal position (FIG. 41A) and a proximal position (FIG. 41B). In versions where the guide tack has retention pin openings, slider (1426) and retention pin (1424) may be distally positioned while the guide tack is secured to second end (1420). When the operator wishes to release the guide tack from second end (1420) (e.g., when the legs of the guide tack are fully inserted into the eye (301) and the head of the guide tack is abutting the surface (305) of the sclera (304)), the operator may retract slider (1426) proximally to retract retention pin (1424) proximally, thereby forcing disengagement between retention pin (1424) and the retention pin openings of the guide tack. Friction between the legs of the guide tack and the sclera (304) will be stronger than the attractive forces between magnets (1428) and the ferrous components of the guide tack (e.g., the upper ends of the legs of the guide tack), such that the guide tack will remain secured to the eye (301) as the operator pulls instrument (1400) away from the guide tack.

In versions where the guide tack lacks retention pin openings, slider (1426) and retention pin (1424) may be proximally positioned while the guide tack is secured to second end (1420) via magnetic attraction between magnets (1428) and ferrous components of the guide tack. When the operator wishes to release the guide tack from second end (1420) (e.g., when the legs of the guide tack are fully inserted into the eye (301) and the head of the guide tack is abutting the surface (305) of the sclera (304)), the operator may advance slider (1426) distally to advance retention pin (1424) distally, while simultaneously pulling instrument (1400) proximally, thereby pushing the guide tack away from magnets (1428). Friction between the legs of the guide tack and the sclera (304) will ensure that the guide tack will remain secured to the eye (301) as the operator pulls instrument (1400) away from the guide tack to disengage the guide tack.

Figure 42:
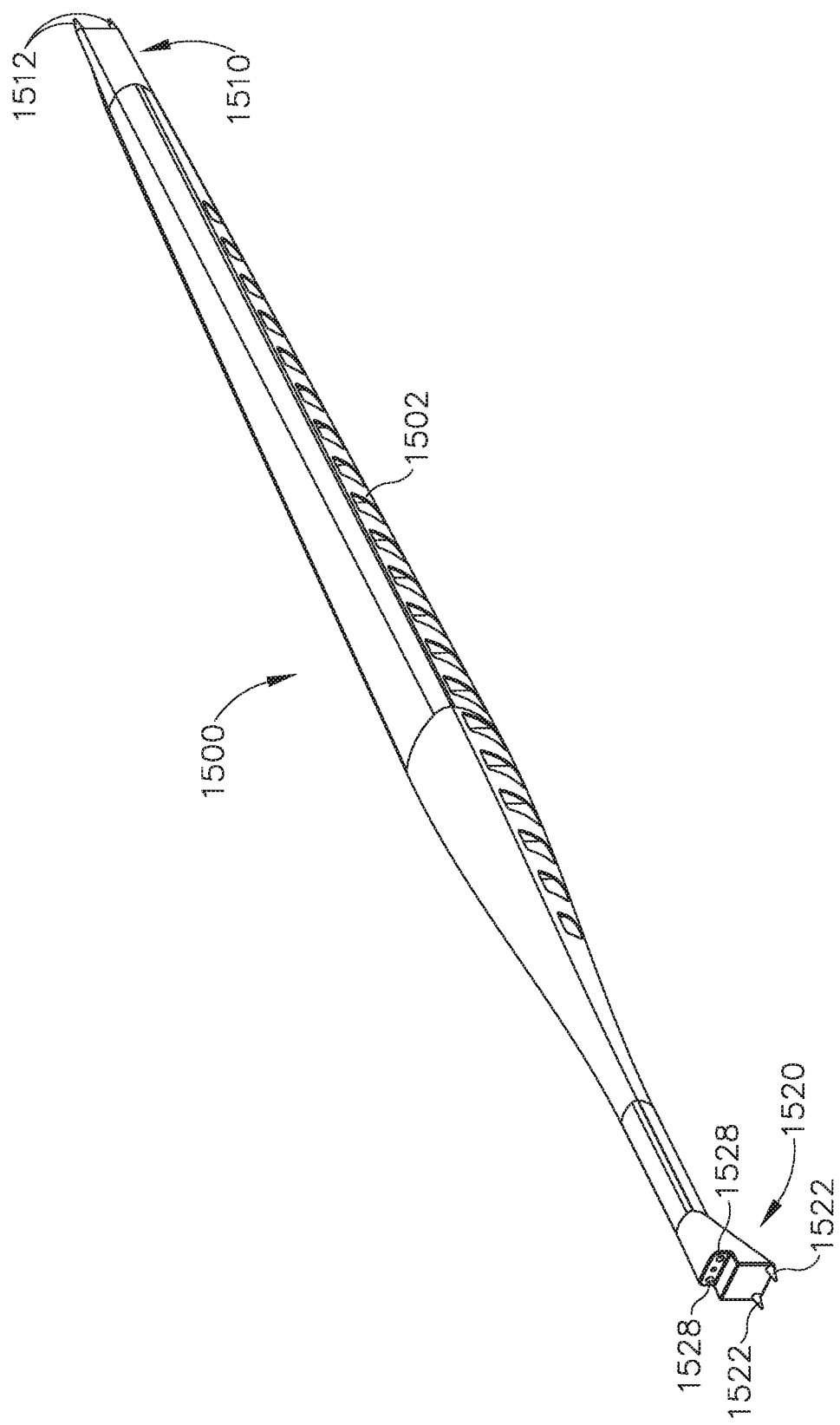
FIG. 42 depicts a perspective view of an exemplary alternative marking and deployment instrument that may be used during performance of the procedure shown in FIGS. 8A-8E.
Figure 43:
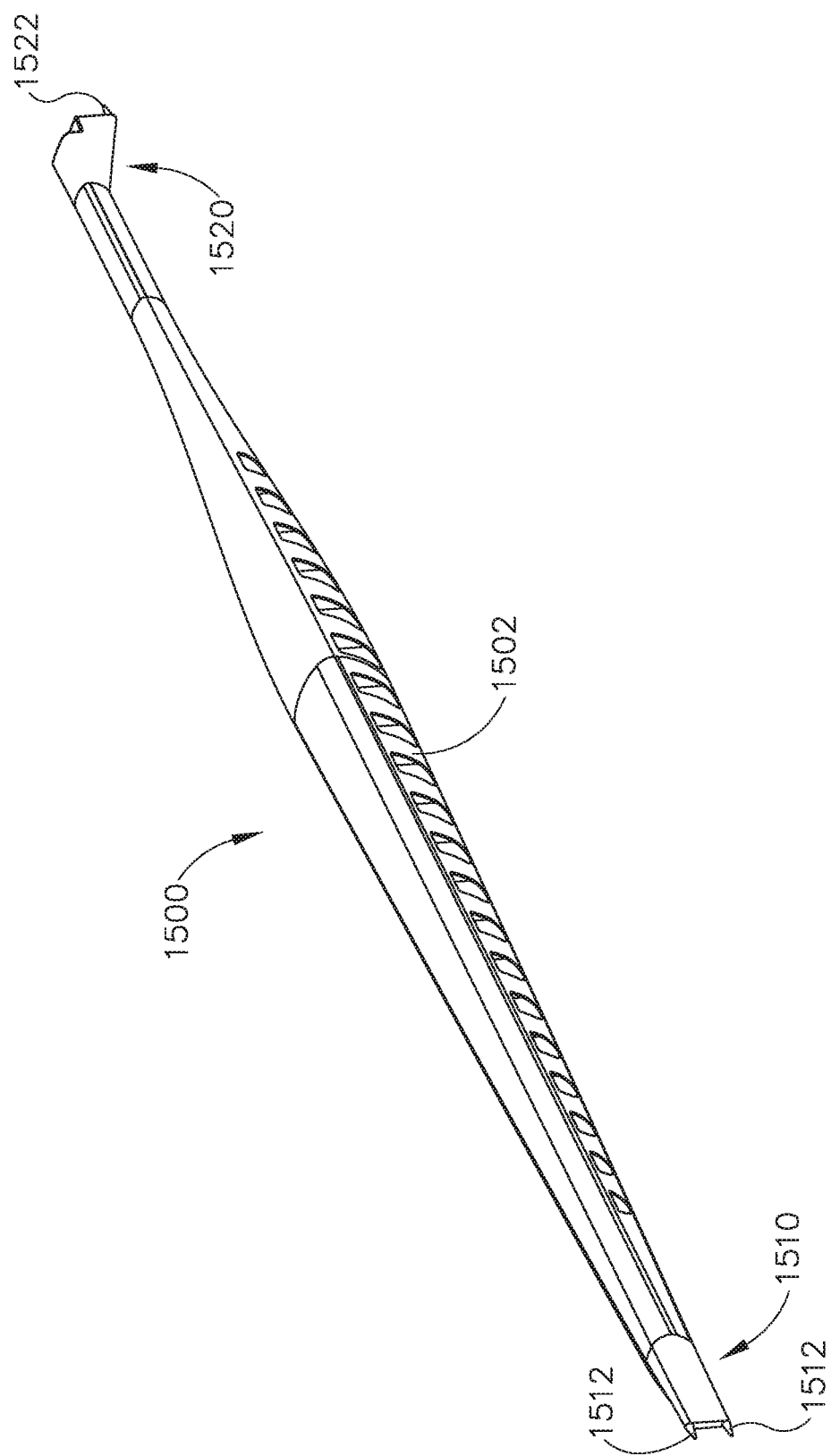
FIG. 43 depicts another perspective view of the marking and deployment instrument of FIG. 42.
Figure 56:
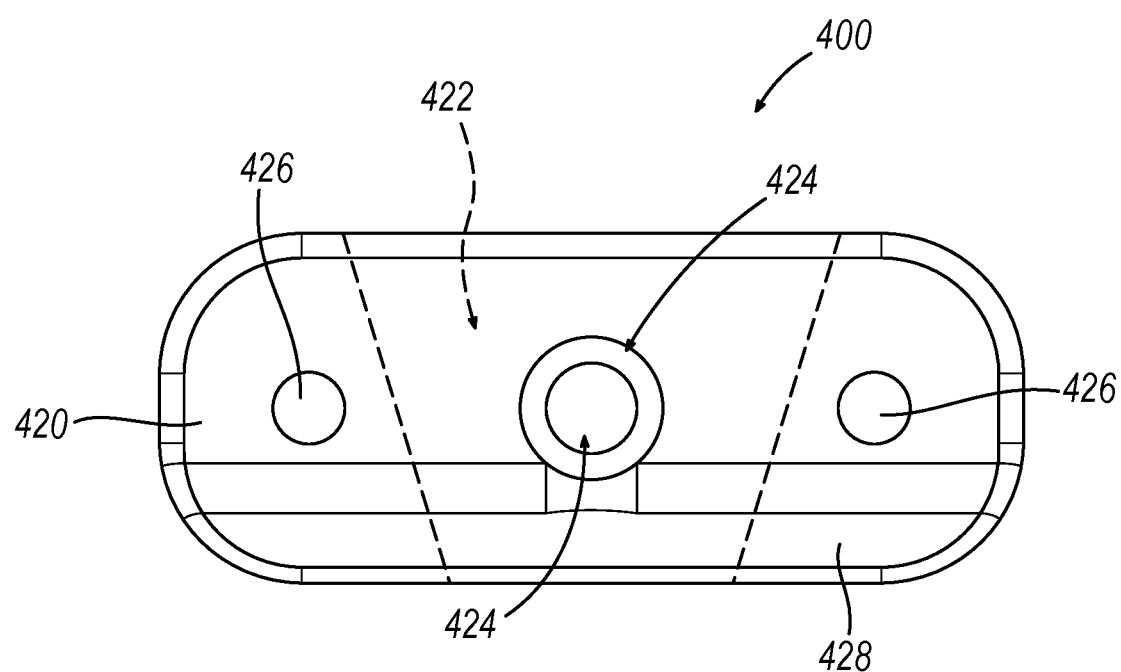

FIGS. 42-43 show another exemplary marking and deployment instrument (1500). Instrument (1500) of this example includes a shaft (1502) having a first end (1510) and a second end (1520). First end (1510) has a set of prongs (1512) that are configured and operable just like prongs (1512) described above. Second end (1520) has a set of prongs (1522) that are configured and operable just like prongs (1422) described above. Second end (1520) also has a pair of magnets (1528) that are configured and operable just like magnets (1428) described above. Unlike instrument (1400), instrument (1500) of this example lacks retention pin (1424) and slider (1426). Instrument (1500) of this example thus relies solely on magnets (1528) to releasably secure a guide tack to second end (1520).

In some variations of instrument (1500), for use with guide tacks that include retention pin openings, second end (1520) includes a stationary retention pin that is not capable of advancing or retracting relative to shaft (1502). In such variations, friction between the legs of the guide tack and the sclera (304) may be stronger than the friction between the retention pin of instrument (1500) and the retention pin openings of the guide tack. In variations of instrument (1500) that have a stationary retention pin, magnets (1528) may still be included or magnets (1528) may be omitted.

FIGS. 44-47 show various examples of marking heads that may be incorporated into any suitable marking instrument. In some versions, these marking heads are provided at one end of a marking and deployment instrument, where the other end of the instrument is configured to removably secure and deploy a guide tack. In some other versions, these marking heads are provided at the end of an instrument that is dedicated solely to marking, such that the instrument lacks features that are configured to removably secure and deploy a guide tack.

In the example shown in FIG. 44, a marking head (1600) includes a first prong (1602), a pair of second prongs (1603), an oblong marking feature (1604), and a pair of third prongs (1606). First prong (1602) is configured to be positioned at the limbus of the eye (301) and thereby serve as a positional reference for the other prongs (1603, 1606) and marking feature (1604) of marking head (1600). Second prongs (1603) are positioned and spaced to correspond with the location and length of the sclerotomy (514). Third prongs (1606) are positioned and spaced to correspond with the location and spacing of the legs of the guide tack. Third prongs (1606) are thus positioned to correspond with the location of the pars plana when first prong (1602) is positioned on the limbus. Oblong marking feature (1604) is sized and configured to correspond with the configuration of the head of the guide tack. Oblong marking feature (1604) surrounds third prongs (1606).

In use, the operator may press marking head (1600) against an inkpad, then position first prong (1602) at the limbus of the eye (301) and press marking head (1600) against the surface (305) of the sclera (304). The operator may then observe the positions of the markings left by third prongs (1606) and insert the legs of the guide tack at the locations of those markings. When the guide tack is fully seated against the surface (305) of the sclera (304), the operator may verify proper positioning by observing correspondence between the marking left by oblong marking feature (1604) and the head of the guide tack. The operator may then form the sclerotomy (314) by using a scalpel to cut between the markings left by second prongs (1603).

In the example shown in FIG. 45, a marking head (1650) includes a first prong (1652), a pair of second prongs (1653), a pair of third prongs (1654), and an oblong marking feature (1656). First prong (1652) is configured to be positioned at the limbus of the eye (301) and thereby serve as a positional reference for the other prongs (1653, 1654) and marking feature (1656) of marking head (1650). Second prongs (1653) are positioned and spaced to correspond with the location and length of the sclerotomy (514). Third prongs (1654) are positioned and spaced to correspond with the location and spacing of the legs of the guide tack. Third prongs (1654) are thus positioned to correspond with the location of the pars plana when first prong (1652) is positioned on the limbus. Oblong marking feature (1656) extends between third prongs (1654).

In use, the operator may press marking head (1650) against an inkpad, then position first prong (1652) at the limbus of the eye (301) and press marking head (1650) against the surface (305) of the sclera (304). The operator may then observe the positions of the markings left by third prongs (1654) and insert the legs of the guide tack at the locations of those markings. The marking left by oblong marking feature (1656) may assist in emphasizing the positions of the markings left by third prongs (1654). When the guide tack is fully seated against the surface (305) of the sclera (304), the operator may then form the sclerotomy (314) by using a scalpel to cut between the markings left by second prongs (1653).

In the example shown in FIG. 46, a marking head (1700) includes a first prong (1702), a pair of second prongs (1703), and a pair of third prongs (1704). First prong (1702) is configured to be positioned at the limbus of the eye (301) and thereby serve as a positional reference for the other prongs (1703, 1704) of marking head (1600). Second prongs (1703) are positioned and spaced to correspond with the location and length of the sclerotomy (514). Third prongs (1704) are positioned and spaced to correspond with the location and spacing of the legs of the guide tack. Third prongs (1704) are thus positioned to correspond with the location of the pars plana when first prong (1702) is positioned on the limbus.

In use, the operator may press marking head (1700) against an inkpad, then position first prong (1702) at the limbus of the eye (301) and press marking head (1700) against the surface (305) of the sclera (304). The operator may then observe the positions of the markings left by third prongs (1704) and insert the legs of the guide tack at the locations of those markings. When the guide tack is fully seated against the surface (305) of the sclera (304), the operator may then form the sclerotomy (314) by using a scalpel to cut between the markings left by second prongs (1703).

In the example shown in FIG. 47, a marking head (1750) includes a first prong (1752), a pair of second prongs (1754), an oblong marking feature (1756), and a pair of third prongs (1758). First prong (1752) is configured to be positioned at the limbus of the eye (301) and thereby serve as a positional reference for the other prongs (1754, 1758) and marking feature (1756) of marking head (1750). Second prongs (1754) are positioned and spaced to correspond with the location and length of the sclerotomy (514). Third prongs (1758) are positioned and spaced to correspond with the location and spacing of the legs of the guide tack. Third prongs (1758) are thus positioned to correspond with the location of the pars plana when first prong (1752) is positioned on the limbus. Oblong marking feature (1756) is sized and configured to correspond with the configuration of the head of the guide tack. Oblong marking feature (1756) surrounds third prongs (1758).

Marking head (1750) is configured and operable just like marking head (1600), except that prongs (1603) have a circular cross-sectional profile while prongs (1754) have a triangular cross-sectional profile. The triangular cross-sectional profiles of prongs (1754) are oriented such that edges of prongs (1754) are pointed toward each other. This configuration and orientation of prongs (1754) may provide a more easily discernible visual indication of where sclerotomy (514) should be formed.

FIGS. 48-55 show various exemplary marking patterns that may be applied to a patient's eye (301) using a marking instrument. By way of example only, such marking patterns may be applied using an instrument that has one end dedicated to marking the patient's eye (301) and another end dedicated to deploying a guide tack in the patient's eye (301). As another merely illustrative example, such marking patterns may be applied using an instrument that is dedicated solely to marking, such that the instrument lacks features that are configured to removably secure and deploy a guide tack.

FIG. 48 shows a marking pattern (1800) that includes a top dot (1804) and additional dots (1802). Top dot (804) is located at the limbus, the lower pair of dots (1802) are located at positions corresponding to the ends of a sclerotomy site, and the upper pair of dots (1802) are located at positions corresponding to insertion points for legs of a guide tack.

FIG. 49 shows a marking pattern (1810) that includes a top dot (1816), additional dots (1812), and a line (1814). Top dot (1816) is located at the limbus, dots (1812) are located at positions corresponding to the ends of a sclerotomy site, and line (1814) is located at positions corresponding to insertion points for legs of a guide tack.

FIG. 50 shows a marking pattern (1820) that includes a top dot (1826), additional dots (1822), and a line (1824). Top dot (1826) is located at the limbus, the lower pair of dots (1822) are located at positions corresponding to the ends of a sclerotomy site, and the upper pair of dots (1822) are located at positions corresponding to insertion points for legs of a guide tack. Line (1824) is positioned between the upper pair of dots (1822) thereby visually emphasizing the position of upper pair of dots (1822).

FIG. 51 shows a marking pattern (1830) that includes a top dot (1836), additional dots (1832), and a hollow oblong mark (1834). Top dot (1836) is located at the limbus, dots (1832) are located at positions corresponding to the ends of a sclerotomy site, and oblong mark (1834) is located at positions corresponding to insertion points for legs of a guide tack.

FIG. 52 shows a marking pattern (1840) that includes several dots (1842, 1844, 1846). Pattern (1840) is identical to pattern (1840) except that dots (1844) are hollow (i.e., circles); whereas the upper pair of dots (1802) are solid.

FIG. 53 shows a marking pattern (1850) that includes several dots (1852, 1856) and an oblong mark (1854). Pattern (1850) is identical to pattern (1830), except that oblong mark (1854) is rectangular; whereas oblong mark (1834) is shaped like an oval or flattened ellipse.

FIG. 54 shows a marking pattern (1860) that includes several dots (1862, 1866) and an oblong mark (1864). Pattern (1860) is identical to pattern (1810), except that oblong mark (1864) is rectangular; whereas oblong mark (1814) is shaped like an oval or flattened ellipse.

FIG. 55 shows a marking pattern (1870) that includes several dots (1862, 1866, 1868) and a line (1864). Pattern (1870) is identical to pattern (1820) except that dots (1866) are hollow (i.e., circles); whereas the upper pair of dots (1822) are solid.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body, wherein the body includes an engagement feature configured to engage a deployment instrument; and (b) a pair of rigid legs extending from the body, wherein the legs are parallel with each other, wherein each leg has a sharp tip, wherein the legs both extend along a plane; wherein the body defines a guide opening, wherein the guide opening is oriented transversely relative to the plane associated with the legs, wherein the guide opening is sized to receive a cannula having a generally flat profile.

Example 2

The apparatus of Example 1, wherein the engage feature comprises a first retaining pin opening, wherein the first retaining pin opening is configured to receive a retaining pin of a deployment instrument.

Example 3

The apparatus of Example 2, wherein the engage feature further comprises a second retaining pin opening, wherein the second retaining pin opening is further configured to receive a retaining pin of a deployment instrument.

Example 4

The apparatus of Example 3, wherein the first and second retaining pin openings are coaxially aligned with each other.

Example 5

The apparatus of any one or more of Examples 3 through 4, wherein the first retaining pin opening is located at an upper side of the guide opening, wherein the second retaining pin opening is located at a bottom side of the guide opening.

Example 6

The apparatus of any one or more of Examples 1 through 5, wherein the body has an upper surface and a lower surface, wherein the legs extend from the lower surface, wherein each leg has an upper end that is exposed relative to the upper surface.

Example 7

The apparatus of Example 6, wherein the legs comprise a ferrous material.

Example 8

The apparatus of any one or more of Examples 1 through 7, wherein the body further includes at least one chamfer.

Example 9

The apparatus of any one or more of Examples 1 through 8, wherein the body further includes at least one rib in the guide opening, wherein the at least one rib is configured to reduce contact between the guide and a cannula disposed in the guide opening.

Example 10

The apparatus of Example 9, wherein the at least one rib is positioned on an upper side of the guide opening.

Example 11

The apparatus of Example 9, wherein the at least one rib comprises a pair of ribs positioned on opposite lateral sides of the guide opening.

Example 12

The apparatus of any one or more of Examples 1 through 11, wherein the body further includes at least one chamfered surface leading into the guide opening.

Example 13

The apparatus of any one or more of Examples 1 through 12, wherein the legs have straight lower portions and bent upper portions, wherein the straight lower portions include the sharp tips, wherein the bent upper portions are located in the body.

Example 14

The apparatus of Example 13, wherein the bent upper portions are bent outwardly relative to a centerline of the body.

Example 15

The apparatus of any one or more of Examples 1 through 14, further comprising an applier instrument, wherein the applier instrument comprises: (i) a shaft, and (ii) a head portion located at an end of the shaft, wherein the head portion comprises: (A) an engagement feature configured to releasably engage the engagement feature of the body, and (B) a marking feature configured to mark a sclerotomy site on an eye.

Example 16

The apparatus of Example 15, wherein the engagement feature comprises a retaining pin.

Example 17

The apparatus of any one or more of Examples 15 through 16, wherein the engagement feature comprises one or more magnets.

Example 18

An apparatus, comprising: (a) a shaft having a first end and a second end; (b) a first marking element at the first end, wherein the first marking element includes prongs configured to define a spacing corresponding to either or both of: (i) a distance between a limbus and a pars plana, or (ii) legs of a guide tack; (c) a second marking element at the second end, wherein the second marking element includes prongs configured to define ends of a sclerotomy site; and (d) a guide tack retaining feature at the second end, wherein the guide tack retaining feature is configured to releasably retain a guide tack.

Example 19

A method of inserting a cannula into an eye of a patient, the method comprising: (a) inserting legs of a guide tack into a pars plana region of the eye, wherein the guide tack further includes a head secured to upper ends of the legs, wherein the head defines a guide opening oriented transversely relative to a plane defined between the legs; (b) forming a sclerotomy near the guide tack; (c) inserting a cannula through the guide opening; and (d) inserting the cannula through the sclerotomy, wherein the guide tack is configured to guide the cannula through the scelrotomy at a substantially tangential orientation.

Example 20

The method of Example 19, further comprising marking the sclerotomy site with a marking and deployment instrument, wherein the act of inserting the legs of the guide tack into the pars plana region of the eye is also performed with the marking and deployment instrument simultaneously with the act of marking the sclerotomy site, wherein the act of forming the sclerotomy is performed using marks formed by the act of marking the sclerotomy site.

VI. Miscellaneous

In the examples described above, the legs of the guide tacks are parallel with each other; and perpendicular relative to the head of the tack. In some variations, the legs of the guide tacks may be splayed inwardly or outwardly, such that the legs are not parallel with each other; and such that the legs are obliquely oriented relative to the head of the tack. In such variations, the legs may be resiliently biased to assume such splayed configurations; yet be deformable to assume a parallel configuration (e.g., during insertion of the legs into the eye (301)). Such splaying of the legs may further promote retention of the guide tack in the eye (301).

The guide tacks described herein may be used with devices and in procedures as described in U.S. patent application Ser. No. 15/609,386, entitled "Apparatus and Method to Form Entry Bleb for Subretinal Delivery of Therapeutic Agent," filed on even date herewith, issued as U.S. Pat. No. 10,646,374 on May 12, 2020, the disclosure of which is incorporated by reference herein; and/or of U.S. patent application Ser. No. 15/609,457, entitled "Injection Device for Subretinal Delivery of Therapeutic Agent," filed on even date herewith, issued as U.S. Pat. No. 10,806,629 on Oct. 20, 2020, the disclosure of which is incorporated by reference herein. Alternatively, the guide tacks described herein may be used with any other suitable devices and or in any other suitable procedures.

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for guiding a cannula through an incision in an eye, wherein the cannula has a generally rectangular or elliptical cross-section, comprising:
    (a) a body, wherein the body includes an engagement feature configured to engage a deployment instrument; and
    (b) a pair of rigid legs extending from the body, wherein the rigid legs are parallel with each other, wherein each rigid leg has a sharp tip dimensioned for insertion through a surface of the eye, wherein the rigid legs both extend along a plane;
    wherein the body has inner walls defining a guide opening, wherein the guide opening is oriented transversely relative to the plane associated with the pair of rigid legs, wherein the guide opening is sized to receive the cannula having the generally rectangular or elliptical cross-section such that the guide opening is configured to maintain the cannula in a substantially tangential orientation relative to the incision when the pair of rigid legs are inserted through the surface of the eye, wherein the guide opening is tapered such that a cannula entry region of the guide opening is wider than a cannula exit region of the guide opening.

2. The apparatus of claim 1, wherein the engagement feature comprises a first retaining pin opening, wherein the first retaining pin opening is configured to receive a retaining pin of the deployment instrument.

3. The apparatus of claim 2, wherein the engagement feature further comprises a second retaining pin opening, wherein the second retaining pin opening is further configured to receive the retaining pin of the deployment instrument.

4. The apparatus of claim 3, wherein the first and second retaining pin openings are coaxially aligned with each other.

5. The apparatus of claim 3, wherein the first retaining pin opening is located at an upper side of the guide opening, wherein the second retaining pin opening is located at a bottom side of the guide opening.

6. The apparatus of claim 1, wherein the pair of rigid legs comprise a ferrous material.

7. The apparatus of claim 1, wherein the body further includes at least one chamfer.

8. The apparatus of claim 1, wherein the body further includes at least one rib in the guide opening, wherein the at least one rib is configured to reduce contact between the guide opening and the cannula disposed in the guide opening.

9. The apparatus of claim 8, wherein the at least one rib is positioned on an upper side of the guide opening.

10. The apparatus of claim 8, wherein the at least one rib comprises a pair of ribs positioned on opposite lateral sides of the guide opening.

11. The apparatus of claim 1, wherein the body further includes at least one chamfered surface leading into the guide opening.

12. The apparatus of claim 1, wherein the pair of rigid legs have straight lower portions and bent upper portions, wherein the straight lower portions include the sharp tips, wherein the bent upper portions are located in the body.

13. The apparatus of claim 12, wherein the bent upper portions are bent outwardly relative to a centerline of the body.

14. The apparatus of claim 1, further comprising the deployment instrument, wherein the deployment instrument comprises:
 (i) a shaft, and
 (ii) a head portion located at an end of the shaft, wherein the head portion comprises:
  (A) an engagement component configured to releasably engage the engagement feature of the body, and
  (B) a marking feature configured to mark a sclerotomy site on the eye.

15. The apparatus of claim 14, wherein the engagement component of the deployment instrument comprises a retaining pin.

16. The apparatus of claim 14, wherein the engagement component of the deployment instrument comprises one or more magnets.

17. A method of using the apparatus of claim 1, the method comprising:
 (a) inserting the rigid legs into an eye of a patient, the rigid legs being inserted adjacent to an incision formed in the eye;
 (b) inserting a cannula through the body via the cannula entry region of the guide opening such that the cannula exits the body via the cannula exit region of the guide opening; and
 (c) further inserting the cannula into the incision formed in the eye.

18. An apparatus, comprising:
 (a) a unitary body; and
 (b) a pair of rigid legs, the pair of rigid legs extend from the unitary body in parallel with each other along a plane, the pair of rigid legs proximally terminating in the unitary body and being unitarily fixed to the unitary body;
 wherein the unitary body defines a guide opening such that the guide opening passes through the unitary body, wherein the guide opening is oriented transversely relative to the plane associated with the pair of rigid legs, wherein the guide opening is sized to receive a cannula having a substantially flat profile, wherein the guide opening comprises inner walls within the unitary body, wherein the inner walls are all obliquely oriented relative to the plane.

19. The apparatus of claim 18, wherein the inner walls are oriented obliquely relative to a plane perpendicular to the plane associated with the pair of rigid legs.

20. An apparatus, comprising:
 (a) a cannula having a generally rectangular or elliptical cross-section; and
 (b) a cannula guide configured to guide the cannula through an incision in an eye, the cannula guide comprising:
  (i) a body, wherein the body includes an engagement feature configured to engage a deployment instrument, wherein the body further includes inner walls defining a guide opening, wherein the guide opening is sized to receive the cannula having the generally rectangular or elliptical cross-section, and
  (ii) a pair of rigid legs extending from the body, wherein the rigid legs are parallel with each other, wherein each rigid leg has a sharp tip dimensioned for insertion through a surface of the eye, wherein the rigid legs both extend along a plane, wherein the guide opening is oriented transversely relative to the plane associated with the pair of rigid legs,
 wherein the guide opening is configured to maintain the cannula in a substantially tangential orientation relative to the incision when the pair of rigid legs are inserted through the surface of the eye.

* * * * *